United States Patent
Paul

(10) Patent No.: US 9,080,179 B2
(45) Date of Patent: *Jul. 14, 2015

(54) ENHANCED PYRUVATE TO 2,3-BUTANEDIOL CONVERSION IN LACTIC ACID BACTERIA

(71) Applicant: BUTAMAX ADVANCED BIOFUELS LLC, Wilmington, DE (US)

(72) Inventor: Brian James Paul, Wilmington, DE (US)

(73) Assignee: BUTAMAX ADVANCED BIOFUELS LLC DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/872,873

(22) Filed: Apr. 29, 2013

(65) Prior Publication Data

US 2013/0316414 A1 Nov. 28, 2013

Related U.S. Application Data

(63) Continuation of application No. 12/569,136, filed on Sep. 29, 2009, now Pat. No. 8,455,224.

(60) Provisional application No. 61/100,786, filed on Sep. 29, 2008.

(51) Int. Cl.
| | | |
|---|---|---|
| C12N 15/74 | (2006.01) | |
| C12N 9/04 | (2006.01) | |
| C12P 7/16 | (2006.01) | |
| C12P 7/18 | (2006.01) | |
| C12P 7/26 | (2006.01) | |

(52) U.S. Cl.
CPC ............ *C12N 15/746* (2013.01); *C12N 9/0006* (2013.01); *C12P 7/16* (2013.01); *C12P 7/18* (2013.01); *C12P 7/26* (2013.01); *C12Y 101/02004* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 6,514,733 | B1 | 2/2003 | Emptage et al. |
| 7,067,300 | B2 | 6/2006 | Emptage et al. |
| 7,504,250 | B2 | 3/2009 | Emptage et al. |
| 8,206,970 | B2 | 6/2012 | Eliot et al. |
| 8,455,224 | B2 * | 6/2013 | Paul .............................. 435/160 |
| 2004/0157305 | A1 | 8/2004 | Stampfer et al. |
| 2007/0031918 | A1 | 2/2007 | Dunson, Jr. et al. |
| 2007/0092957 | A1 | 4/2007 | Donaldson et al. |
| 2007/0292927 | A1 | 12/2007 | Donaldson et al. |
| 2009/0081746 | A1 | 3/2009 | Liao et al. |
| 2009/0155870 | A1 | 6/2009 | Donaldson et al. |
| 2009/0239275 | A1 | 9/2009 | Donaldson et al. |
| 2009/0269823 | A1 | 10/2009 | Bramucci et al. |
| 2009/0305363 | A1 | 12/2009 | Anthony et al. |
| 2009/0305369 | A1 | 12/2009 | Donaldson et al. |
| 2010/0081154 | A1 | 4/2010 | Flint et al. |
| 2010/0081179 | A1 | 4/2010 | Anthony et al. |
| 2010/0081182 | A1 | 4/2010 | Paul et al. |
| 2010/0081183 | A1 | 4/2010 | Paul et al. |
| 2012/0196341 | A1 | 8/2012 | Donaldson et al. |

FOREIGN PATENT DOCUMENTS

| | | |
|---|---|---|
| WO | WO99/54453 | 10/1999 |
| WO | WO2007/130518 | 11/2007 |
| WO | WO2008/098227 | 8/2008 |

OTHER PUBLICATIONS

Neves et al. Eur J Biochem. Jun. 2000;267(12):3859-68.*
Ui et al. Lett Appl Microbiol. 2004;39(6):533-7.*
Karlin et al. Proc Natl Acad Sci U S A. Apr. 20, 2004;101(16):6182-7. Epub Apr. 6, 2004.*
Henriksen et al. Appl Microbiol Biotechnol. Sep. 2001;56(5-6):767-75.*
International Search Report and Written Opinion in corresponding PCT/US2009/058834 mailed Jan. 20, 2010.
Henriksen et al., "Redirection of pyruvate catabolism in *Lactococcus lactis* by selection of mutants with additional growth requirements", Appl. Microbiol. Biotechnol. (2001) 56:767-775.
Speranza et al., "Conversion of meso-2,3-Butanedio into 2-Butanol by Lactobacilli. Stereochemical and Enzymatic Aspects", J. Agric. Food Chem. (1997) 45, 3476-3480.
Celinska et al., "Biotechnological production of 2,3-butanediol-Current state and prospects", Biotechnology Advances 27 (2009) 715-725.
Crow, "Properties of 2,3-Butanediol Dehydrogenases from *Lactococcus lactis* subsp. *lactis* in Relation to Citrate Fermentation", Appl. Environ. Microbiol., (1990) 1656-1665.
Cruz-Rodz et al., "High efficiency introduction of plasmid DNA into glycine treated *Enterococcus faecalis* by electroporation", Molecular Genetics and Genomics, 224:152-154 (1990).
Genbank NC_004567.1 accessed on Mar. 4, 2010.
Voloch et al. Fermentation Derived 2,3-Butanediol, in Comprehensive Biotechnology, Pergamon Press Ltd, England vol. 2, Section 3:933-947 (1986).
Advanced Bacterial Genetics (Davis, Roth and Botstein) Cold Spring Harbor Laboratory, 1980.
T. J. Silhavy, M. L. Bennan, and L. W. Enquist, Experiments with Gene Fusions, Cold Spring Harbor Laboratory, Cold Spring Harbor, N.Y., 1984.
Thein and Wallace, "The use of oligonucleotides as specific hybridization probes in the Diagnosis of Genetic Disorders", in Human Genetic Diseases: A Practical Approach, K. E. Davis Ed., (1986) pp. 33-50, IRL: Herndon, VA.
Alegre et al., "Transformation of *Lactobacillus plantarum* by electroporation with in vitro modified plasmid DNA" FEMS Microbiology letters 241:73-77 (2004).
Altschul, S. F., et al., "Basic Local Alignment Search Tool", J. Mol. Biol., 215:403 410 (1990).
Arthur et al., "Contribution of VanY D,D-Carboxypeptidase to Glycopeptide Resistance in *Enterococcus faecalis* by Hydrolysis of Peptidoglycan Precursors", Antimicrob. Agents Chemother. 38:1899-1903 (1994).

(Continued)

*Primary Examiner* — Christian Fronda

(57) ABSTRACT

A high flux of metabolites from pyruvate to 2,3-butanediol in *Lactobacillus plantarum* was achieved through genetic engineering. Substantial elimination of lactate dehydrogenase activity in the presence of heterologously expressed butanediol dehydrogenase activity led to 2,3 butanediol production that was at least 49% of the total of major pyruvate-derived products.

17 Claims, 4 Drawing Sheets

(56) References Cited

OTHER PUBLICATIONS

Bringel, et al. "Optimized transformation by electroporation of *Lactobacillus plantarum* strains with plasmid vectors", Appl. Microbiol. Biotechnol. 33: 664-670 (1990).
Deshpande, Mukund V., "Ethanol Production from Cellulose by Coupled Saccharification/Fermentation using *Saccharomyces cerevisiae* and Cellulase Complex from *Sclerotium rolfsii* UV-8 Mutant", Appl. Biochem. Biotechnol., 36:227, (1992).
Durre, "New insights and novel developments in clostridial acetone/butanol/isopropanol fermenation", Appl. Microbiol. Biotechnol. 49:639-648 (1998).
Eichenbaum et al. "Use of the Lactococcal nisA Promoter to Regulate Gene Expression in Gram-Positive Bacteria: Comparison of Induction Level and Promoter Strength", Appl. Environ. Microbiol. 64(8):2763-2769 (1998).
Ferain et al."*Lactobacillus plantarum* ldhL gene: Overexpression and Deletion", J. Bact. 176:596 (1994).
Frohman et al."Rapid production of full-length cDNAs from rare transcripts: Amplification using a single gene-specific oligonucleotide primer", PNAS USA 85:8998 (1988).
Fujimoto et al. "pAM401-Based Shuttle Vectors That Enable Overexpression of Promoterless Genes and one-Step Purification of Tag Fusion Proteins Directly from *Enterococcus faecalis*", Appl. Environ. Microbiol. 67:1262-1267 (2001).
Gollop et al. "Physiological Implications of the Substrate Specificities of Acetohydroxy Acid Synthases from Varied Organisms", J. Bacteriol. 172(6):3444-3449 (1990).
Groot et al., "Technologies for Butanol Recovery Integrated with Fermentations", Process. Biochem. 27:61-75 (1992).
Higgins and Sharp, "Fast and sensitive multiple sequence alignments on a microcomputer", CABIOS. 5:151-153 (1989).
Higgins, D.G. et al., "CLUSTAL V: improved software for multiple sequence alignment", Comput. Appl. Biosci., 8:189-191 (1992).
Hols et al. "Use of Homologous Expression-Secretion Signals and Vector-Free Stable Chromosomal Integration in Engineering of *Lactobacillus plantarum* for a-Amylase and Levanase Expression", Nature Biotech. 17:588-592 (1999).
Hols et al., "Conversion of *Lactococcus lactis* from homolactic to homoalanine fermentation through metabolic engineering", Appl. Environ. Microbiol. 60:1401-1413 (1994).
Holtzclaw et al., "Degradative Acetolactate Synthase of *Bacillus subtilis*: Purification and Properties", J. Bacteriol. 121(3):917-922 (1 975).
Horinouchi and Weisblum, "Nucleotide Sequence and Functional Map of pE194, a Plasmid That Specifies Inducible Resistance to Macrolide, Lincosamide, and Streptogramin Type B Antibiotics", J. Bacteriol. (1982) 150(2):804-814.
Jang et al.,"New integration vector using a cellulase gene as a screening marker for *Lactobacillus*", Micro. Lett. 24:191-195 (2003).
Kleerebezem et al., "Controlled Gene Expression Systems for Lactic Acid Bacteria: Transferable Nisin-Inducible Expression Cassettes for *Lactococcus, Leuconostoc,* and *Lactobacillus* spp.", Appl. Environ. Microbiol. 63:4581-4584 (1997).
Liu et al., "Metabolic engineering of a *Lactobacillus plantarum* double ldh knockout strain for enhanced ethanol production", J. Ind. Micro. Biotech. 33:1-7 (2006).
Loh et al., "Polymerase Chain Reaction with Single-Sided Specificity: Analysis of T Cell Receptor d Chain", Science 243:217 (1989).
Nystrom, R. F. and Brown, W. G., "Reduction of Organic Compounds by Lithium Aluminum Hydride. I. Aldehydes, Ketones, Esters, Acid Chlorides, and Acid Anhydrides", J. Am. Chem. Soc. (1947) 69:1198.
Ohara et al., "One-sided polymerase chain reaction: The amplification of cDNA", PNAS USA 86:5673 (1989).
O'Sullivan et al., "High- and low-copy-number *Lactococcus* shuttle cloning vectors with features for clone screening", Gene 137:227-231 (1993).
Renault et al., "Plasmid vectors for Gram-positive bacteria switching from high to low copy number", Gene 183:175-182 (1996).
Rud et al., "A synthetic promoter library for constitutive gene expression in *Lactobacillus plantarum*", Microbiology 152:1011-1019 (2006).
Shrago et al.,"Conjugal Plasmid Transfer (pAMb1) in *Lactobacillus plantarum*", Appl. Environ. Microbiol. 52:574-576 (1986).
Tabor, S. et al., "A bacteriophage T7 RNA polymerase/promoter system for controlled exclusive expression of specific genes", Proc. Acad. Sci. USA 82:1074 (1985).
Tanimoto et al., "Analysis of the Conjugal Transfer System of the Pheromone-Independent Highly Transferable *Enterococcus* Plasmid pMG1: Identification of a tra Gene (traA) Up-Regulated during Conjugation", J. Bacteriol. 184:5800-5804 (2002).
Thompson, J. D., Higgins, D. G., and Gibson T. J., "CLUSTAL W: improving the sensitivity of progressive multiple sequence alignment through sequence weighting, position-specific gap penalties and weight matrix choice", Nuc. Acid Res. 22: 4673 4680 (1994).
Van Ness and Chen, "The use of oligodeoxynucleotide probes in chaotrope-based hybridization solutions", Nucl. Acids Res. 19:5143 5151 (1991).
van Kranenburg et al., "Functional Analysis of Three Plasmids from *Lactobacillus plantarum*", Appl. Environ. Microbiol. Mar. 2005; 71(3): 1223-1230.
Walker, et al., "Isothermal in vitro amplification of DNA by a restriction enzyme/DNA polymerase system", Proc. Natl. Acad. Sci. U.S. A., 89:392 (1992).
Wyckoff et al., "Characterization and Sequence Analysis of a Stable Cryptic Plasmid from *Enterococcus faecium* 2226 and Development of a Stable Cloning Vector", Appl. Environ. Microbiol. 62:1481-1486 (1996).
Ausubel, F. M. et al., Current Protocols in Molecular Biology, Greene Publishing Assoc. and Wiley-Interscience, N.Y., 1987.
Biocomputing: Informatics and Genome Projects (Smith, D. W., Ed.) Academic: NY (1993).
Thomas D. Brock in Biotechnology: A Textbook of Industrial Microbiology, Second Edition (1989) Sinauer Associates, Inc., Sunderland, MA.
Computational Molecular Biology (Lesk, A. M., Ed.) Oxford University: NY (1988).
Computer Analysis of Sequence Data, Part I (Griffin, A. M., and Griffin, H. G., Eds.) Humania: NJ (1994).
Experiments in Molecular Genetics (Miller) Cold Spring Harbor Laboratory, 1972.
Experimental Techniques in Bacterial Genetics (Maloy, in Jones and Bartlett) 1990.
W. R. Pearson, Comput. Methods Genome Res., [Proc. Int. Symp.] (1994), Meeting Date 1992, 111 20. Editor(s): Suhai, Sandor. Plenum: New York, NY.
Rychlik, W., In Methods in Molecular Biology, White, B. A. Ed., (1993) vol. 15, pp. 31 39, PCR Protocols: Current Methods and Applications. Humania: Totowa, NJ.
Sambrook, J., Fritsch, E. F. and Maniatis, T. Molecular Cloning: A Laboratory Manual, 2nd ed., Cold Spring Harbor Laboratory: Cold Spring Harbor, NY (1989).
Sequence Analysis in Molecular Biology (von Heinje, G., Ed.) Academic (1987).
Sequence Analysis Primer (Gribskov, M. and Devereux, J., Eds.) Stockton: NY (1991).
Krogh A. et al., (1994) Journal of Molecular Biology, vol. 235, No. 5, 1501-1531.
International Search Report and Written Opinion From PCT Application No. PCT/US2009/058815, mailed Jan. 13, 2010.
Stewart, "A Chemist's Perspective on the Use of Genetically Engineered Microbes as Reagents for Organic Synthesis" biotechnology and Genetic Engineering Reviews, vol. 14, Apr. 1997, pp. 67-143.
O'Brien et al. "Insight into the Mechanism of the B12-Independent Glycerol Dehydratase from *Clostridium butyricum*: Preliminary Biochemical and Structural Characterization", Biochemistry. 43(16) 4635-4645 (2004).
Scott et al. "Whole-Genome Transcription Profiling Reveals Genes Up-Regulated by Growth on Fucose in the Human Gut Bacterium "Roseburia inulinivorans"", Journal of Bacteriology, 188(12) 4340-4349 (2006).

(56) References Cited

OTHER PUBLICATIONS

Seyfried, et al. "Cloning, sequencing, and overexpression of the genes encoding coenzyme B12-dependent glycerol dehydratase of *Citrobacter freundii*", Journal of Bacteriology, 178(19): 5793-5796 (1996).

Tobimatsu, et al. "Molecular Cloning, Sequencing, and Expression of the Genes Encoding Adenosylcobalamin-dependent Diol Dehydrase of *Klebsiella oxytoca*", Journal of Biological Chemistry, 270(13): 7142-7148 (1995).

Voloch, et al. "Reduction of Acetoin to 2,3-Butanediol in *Klebsiella pneumoniae*: A New Model" Biotechnology and Bioengineering, vol. XXV: 173-183 (1983).

Bell, et al. Genbank Accession No. Q6D510, NCBI database (2004), Putative class-III aminotransferase; last modified date Oct. 31, 2006; accessed Jun. 17, 2008.

Branden et al., Introduction to Protein Structure, Garland Publishing Inc., p. 247 New York, United States, (1991).

Scott, et al. GenBank Accession No. ABC25539.1, NCBI database (2006), Glycerol dehydratase [*Roseburia inulinivorans*]; last modified date: Jun. 5, 2006; accessed Sep. 16, 2009.

Brenda Database EC 4.2.1.30—glycerol dehydratase, accessed on Sep. 23, 2009.

Brenda Database EC 4.2.1.30—glycerol dehydratase, accessed on Apr. 15, 2010.

Guo, H. et al. (2004) Protein tolerance to random amino acid change. PNAS 101(25):9205-9210.

Neves et al., Eur J Biochem., Jun. 2000, 267(12), 3859-68.

Ui et al., Lett Appl Microbiol., 2004, 39(6), 533-7.

Karlin et al., Proc Natl Acad Sci U S A, Apr. 20, 2004 101(16), 6182-7. Epub Apr. 6, 2004.

Notice of Allowance mailed Mar. 2, 2012, in U.S. Appl. No. 11/741,892, filed Apr. 30, 2007.

Notice of Allowance mailed Nov. 14, 2011, in U.S. Appl. No. 11/741,892, filed Apr. 30, 2007.

Notice of Allowance mailed Jul. 27, 2011, in U.S. Appl. No. 11/741,892, filed Apr. 30, 2007.

Notice of Allowance mailed Mar. 28, 2011, in U.S. Appl. No. 11/741,892, filed Apr. 30, 2007.

Office Action mailed Nov. 17, 2009, in U.S. Appl. No. 11/741,892, filed Apr. 30, 2007.

Office Action mailed Jun. 24, 2008, in U.S. Appl. No. 11/741,892, filed Apr. 30, 2007.

Office Action mailed Aug. 5, 2010, in U.S. Appl. No. 11/741,892, filed Apr. 30, 2007.

Office Action mailed Dec. 15, 2008, in U.S. Appl. No. 11/741,916, filed Apr. 30, 2007.

Office Action mailed Apr. 7, 2009, in U.S. Appl. No. 11/741,892, filed Apr. 30, 2007.

Office Action mailed Sep. 16, 2010, in U.S. Appl. No. 11/741,916, filed Apr. 30, 2007.

Office Action mailed Apr. 28, 2011, in U.S. Appl. No. 11/741,916, filed Apr. 30, 2007.

Office Action mailed Dec. 23, 2011, in U.S. Appl. No. 11/741,916, filed Apr. 30, 2007.

Office Action mailed Oct. 7, 2009, in U.S. Appl. No. 11/741,916, filed Apr. 30, 2007.

Office Action mailed Oct. 2, 2009, in U.S. Appl. No. 12/111,359, filed Apr. 29, 2008.

Office Action mailed Apr. 1, 2011, in U.S. Appl. No. 12/111,359, filed Apr. 29, 2008.

Office Action mailed Dec. 6, 2011, in U.S. Appl. No. 12/111,359, filed Apr. 29, 2008.

Office Action mailed Jun. 24, 2010, in U.S. Appl. No. 12/111,359, filed Apr. 29, 2008.

Office Action mailed Apr. 27, 2010, in U.S. Appl. No. 12/472,765, filed May 27, 2009.

Office Action mailed Jan. 7, 2011, in U.S. Appl. No. 12/472,765, filed May 27, 2009.

\* cited by examiner

```
                            SEQUENCE LISTING

<160> NUMBER OF SEQ ID NOS: 113

<210> SEQ ID NO 1
<211> LENGTH: 999
<212> TYPE: DNA
<213> ORGANISM: Lactobacillus plantarum

<400> SEQUENCE: 1
atgaaaatta ttgcatatgc tgtacgtgat gacgaacgtc cattcttcga tacttggatg      60
aaagaaaacc cagatgttga agttaaatta gttccagaat tacttactga agacaacgtt     120
gacttagcta aaggcttcga cggtgccgat gtataccaac aaaaggacta tactgctgaa     180
gtattgaaca agttagccga cgaagggtt aagaacatct ctcttcgtaa cgttggtgtt     240
gataacttgg acgttcctac tgttaaagca cgtggcttaa acatttctaa cgtacctgca     300
tactcaccaa atgcgattgc tgaattatca gtaacgcaat tgatgcaatt attacgtcaa     360
accccattgt tcaataagaa gttagctaag caagacttcc gttgggcacc agatattgcc     420
aaggaattaa acaccatgac tgttggtgtt atcggtactg gtcggattgg ccgtgctgcc     480
atcgatattt tcaaaggctt cggcgctaag gttatcggtt acgatgttta ccggaatgct     540
gaacttgaaa aggaaggcat gtacgttgac accttggacg aattatacgc caagctgat      600 gttatcacgt tacacgttcc tgcattgaag ataactacc acatgttgaa tgcggatgcc     660
ttcagcaaga tgaaagatgg cgcctacatc ttgaactttg ctcgtgggac actcatcgat     720
tcagaagact tgatcaaagc cttagacagt ggcaaagttg ccggtgccgc tcttgatacg     780
tatgaatacg aaactaagat cttcaacaaa gaccttgaag gtcaaacgat tgatgacaag     840
gtcttcatga acttgttcaa ccgcgacaat gttttgatta caccacatac ggctttctac     900
actgaaactg ccgttcacaa catggtgcac gtttcaatga acagtaacaa acaattcatc     960
gaaactggta aagctgatac gcaagttaag tttgactaa                            999

<210> SEQ ID NO 2
<211> LENGTH: 332
<212> TYPE: PRT
<213> ORGANISM: Lactobacillus plantarum

<400> SEQUENCE: 2

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
    50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Leu Phe Asn Lys Lys Leu
```

Ala Lys Gln Asp Phe Arg Trp Ala Pro Asp Ile Ala Lys Glu Leu Asn
            115                 120                 125
Thr Met Thr Val Gly Val Ile Gly Thr Gly Arg Ile Gly Arg Ala Ala
130                 135                 140
Ile Asp Ile Phe Lys Gly Phe Gly Ala Lys Val Ile Gly Tyr Asp Val
145                 150                 155                 160
Tyr Arg Asn Ala Glu Leu Glu Lys Gly Met Tyr Val Asp Thr Leu
            165                 170                 175
Asp Glu Leu Tyr Ala Gln Ala Asp Val Ile Thr Leu His Val Pro Ala
            180                 185                 190
Leu Lys Asp Asn Tyr His Met Leu Asn Ala Asp Ala Phe Ser Lys Met
195                 200                 205
Lys Asp Gly Ala Tyr Ile Leu Asn Phe Ala Arg Gly Thr Leu Ile Asp
210                 215                 220
Ser Glu Asp Leu Ile Lys Ala Leu Asp Ser Gly Lys Val Ala Gly Ala
225                 230                 235                 240
Ala Leu Asp Thr Tyr Glu Tyr Glu Thr Lys Ile Phe Asn Lys Asp Leu
            245                 250                 255
Glu Gly Gln Thr Ile Asp Asp Lys Val Phe Met Asn Leu Phe Asn Arg
            260                 265                 270
Asp Asn Val Leu Ile Thr Pro His Thr Ala Phe Tyr Thr Glu Thr Ala
            275                 280                 285
Val His Asn Met Val His Val Ser Met Asn Ser Asn Lys Gln Phe Ile
290                 295                 300
Glu Thr Gly Lys Ala Asp Thr Gln Val Lys Phe Asp
305                 310                 315                 320
            325                 330

<210> SEQ ID NO 3
<211> LENGTH: 963
<212> TYPE: DNA
<213> ORGANISM: Lactobacillus plantarum

<400> SEQUENCE: 3

```
ttgtcaagca tgccaaatca tcaaaaagtt gtgttagtcg gcgacggcgc tgttggttct    60
agttacgctt ttgccatggc acaacaagga attgctgaag aatttgtaat tgtcgatgtt   120
gttaaagatc ggacaaaggg tgacgccctt gatcttgaag acgccaagc attcaccgct   180
cccaagaaga tttactcagg cgaatattca gattgtaagg acgctgactt agttgttatt   240
acagccggtg cgcctcaaaa gcctggtgaa tcacgtttag acttagttaa caagaattta   300
aatatcctat catccattgt caaaccagtt gttgactccg gctttgacgg catcttctta   360
gttgctgcta accctgttga catcttaact tacgctactt ggaaattctc aggttttccca   420
aaggatcgtg tcattggttc agggacttcc ttagactctt cacgtttacg cgttgcgtta   480
ggcaaacaat tcaatgttga tcctcgttcc gttgatgctt acatcatggg tgaacacggt   540
gattctgaat tgctgcctta ctcaactgca accatcggga cacgtccagt tcgcgatgtc   600
gctaaggaac aaggcgtttc tgacgaagat ttagccaagt tagaagacgg tgttcgtaac   660
aaagcttacg acatcatcaa cttgaagggt gccacgttct acggtatcgg gactgcttta   720
atgcggattt ccaaagccat tttacgtgat gaaaatgccg ttttaccagt aggtgcctac   780
atggacggcc aatacggctt aaacgacatt tatatcggga ctccggctgt gattggtgga   840
actggtttga acaaatcat cgaatcacca ctttcagctg acgaactcaa gaagatgcaa   900
```
gattccgccg caactttgaa aaagtgctt aacgacggtt tagctgaatt agaaaataaa         960
taa                                                                      963

<210> SEQ ID NO 4
<211> LENGTH: 320
<212> TYPE: PRT
<213> ORGANISM: Lactobacillus plantarum

<400> SEQUENCE: 4

```
Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Asp Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Glu Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Val Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320
```

<210> SEQ ID NO 5
<211> LENGTH: 930
<212> TYPE: DNA
<213> ORGANISM: Lactobacillus plantarum

<400> SEQUENCE: 5

```
atggataaga agcaacgcaa agtcgtaatt gttggtgatg gctcggtggg ttcatcattt      60
gccttttcat tggtccaaaa ttgcgcccta gatgaactcg ttatcgttga cttggttaaa     120
acgcacgcag aggggacgt taaggattg gaagatgttg ccgcctttac gaatgcgacc      180
aacattcata ccggtgaata tgcggatgcg cgtgatgctg acatcgttgt cattacggct     240
ggtgtgcctc gtaagcctgg tgagagtcgt ttagatttga ttaaccgcaa tacgaagatt     300
ctggaatcca tcgtcaaacc agtggttgcg agtggtttta atggttgctt cgttatctca     360
agtaatcccg tcgatatttt gacttcgatg acgcaacgtt tatccggttt ccacggcat      420 cgggtcattg gtaccgggac ttccttggat acggcgcgt tacgggtcgc cttggctcag      480
aagttgaatg ttgccaccac tgcagttgat gctgcggtac ttggagaaca tggtgatagt     540
tccatcgtta attttgatga aattatgatc aatgctcagc ccttaaagac ggtcacaacg     600
gtcgatgatc agttcaaagc tgaaatcgag caagctgttc gtggtaaagg tggtcaaatc     660
attagtcaga agggggccac gttctatggg gtcgccgtta gtttgatgca aatctgccga     720
gcaattttga acgatgaaaa tgctgagttg attgtctccg ccgctttgtc tggtcaatat     780
ggcattaacg atttgtactt ggggtcaccc gccattatta accgcaacgg gctccaaaaa     840
gtgatcgaag ctgagctatc agatgatgag cgtgcccgga tgcaacattt cgcagccaag     900
atgctgacca tgatgaatgt ggcatcataa                                       930
```

<210> SEQ ID NO 6
<211> LENGTH: 309
<212> TYPE: PRT
<213> ORGANISM: Lactobacillus plantarum

<400> SEQUENCE: 6

```
Met Asp Lys Lys Gln Arg Lys Val Val Ile Val Gly Asp Gly Ser Val
1               5                   10                  15

Gly Ser Ser Phe Ala Phe Ser Leu Val Gln Asn Cys Ala Leu Asp Glu
            20                  25                  30

Leu Val Ile Val Asp Leu Val Lys Thr His Ala Glu Gly Asp Val Lys
        35                  40                  45

Asp Leu Glu Asp Val Ala Ala Phe Thr Asn Ala Thr Asn Ile His Thr
    50                  55                  60

Gly Glu Tyr Ala Asp Ala Arg Asp Ala Asp Ile Val Val Ile Thr Ala
65                  70                  75                  80

Gly Val Pro Arg Lys Pro Gly Glu Ser Arg Leu Asp Leu Ile Asn Arg
                85                  90                  95

Asn Thr Lys Ile Leu Glu Ser Ile Val Lys Pro Val Val Ala Ser Gly
            100                 105                 110

Phe Asn Gly Cys Phe Val Ile Ser Ser Asn Pro Val Asp Ile Leu Thr
        115                 120                 125

Ser Met Thr Gln Arg Leu Ser Gly Phe Pro Arg His Arg Val Ile Gly
    130                 135                 140

Thr Gly Thr Ser Leu Asp Thr Ala Arg Leu Arg Val Ala Leu Ala Gln
145                 150                 155                 160

Lys Leu Asn Val Ala Thr Thr Ala Val Asp Ala Ala Val Leu Gly Glu
                165                 170                 175

His Gly Asp Ser Ser Ile Val Asn Phe Asp Glu Ile Met Ile Asn Ala
            180                 185                 190

Gln Pro Leu Lys Thr Val Thr Thr Val Asp Asp Gln Phe Lys Ala Glu
        195                 200                 205
```

```
Ile Glu Gln Ala Val Arg Gly Lys Gly Gly Gln Ile Ile Ser Gln Lys
    210                 215                 220

Gly Ala Thr Phe Tyr Gly Val Ala Val Ser Leu Met Gln Ile Cys Arg
225                 230                 235                 240

Ala Ile Leu Asn Asp Glu Asn Ala Glu Leu Ile Val Ser Ala Ala Leu
                245                 250                 255

Ser Gly Gln Tyr Gly Ile Asn Asp Leu Tyr Leu Gly Ser Pro Ala Ile
                260                 265                 270

Ile Asn Arg Asn Gly Leu Gln Lys Val Ile Glu Ala Glu Leu Ser Asp
            275                 280                 285

Asp Glu Arg Ala Arg Met Gln His Phe Ala Ala Lys Met Leu Thr Met
    290                 295                 300

Met Asn Val Ala Ser
305
```

<210> SEQ ID NO 7
<211> LENGTH: 710
<212> TYPE: DNA
<213> ORGANISM: Lactobacillus plantarum

<400> SEQUENCE: 7

```
atgaagcgac caattatcat tgcgttagat tttcccaccg ccgaacgggc cttagctttt      60
ttagaccaat ttccggctga tttacatgtc actgtcaaaa tcggcatgga gttattttat    120
gcagcgggac cgagtattgt gacggacgtg caagctcgcg ccatgcggt tttcttagat     180
ttgaaactac atgatattcc caataccgtc gaatccgcaa tgcgggtgat cgggcggtta    240
ggggtaacct atacgacggt tcatgctgcg ggtgggcacg tgatgctttc agccgccaaa    300
cgaggattgg tcgcgggtgc aatggccgct ggagtcactg cccccaagtt attagcgatt    360
acgcagttaa cttcgactaa tcaagctatt ttgaatcagg accagcaaat catgggaacg    420
gttcgggcga gtgtcgtgca ttatgccaaa ctagcacggg cgagtgactg tgatggcgtc    480
atttgttccg cccaagaagt tcaggcgatt catacggccg tcggtgctga ttttctcgga    540
attacgccgg gaattcggcc agcgtcggcg cagtcagatg accagcaacg ggtgatgaca    600
ccggctgccg ctgctaaggc tgggagcaac ggtctcgtca tcgggcggcc aattacgcag    660
gctgcagaac cagttcaagc ttaccgagat attatgacag aatggagtaa                 710
```

<210> SEQ ID NO 8
<211> LENGTH: 252
<212> TYPE: DNA
<213> ORGANISM: Lactobacillus plantarum

<400> SEQUENCE: 8

```
taagtcgtat tggcaccact actcacaccg tgaccgacgc gcccgccagt caagtgttca      60
aaagttagcg tttattaagt gcgataagta taccacaaag gcttattgg cgcccgccaa     120
agggttttgc ggacattgtt aataattgta ttaaaagcat gctcaatcta acacttattt    180
tgcacaaaca tggtatactt taaccgtaaa aactaaattt tcactacgag aggatgactt    240
attttgtcaa gc                                                         252
```

<210> SEQ ID NO 9
<211> LENGTH: 1047
<212> TYPE: DNA
<213> ORGANISM: Achromobacter xylosoxidans

<400> SEQUENCE: 9

```
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180
gaaggggtag gcgtcatcga ggaagtgggc gagagtgtca cgcagttcaa gaaaggcgac     240
aaggtcctga tttcctgcgt cacttcttgc ggctcgtgcg actactgcaa gaagcagctt     300
tactcccatt gccgcgacgg cgggtggatc ctgggttaca tgatcgatgg cgtgcaggcc     360
gaatacgtcc gcatcccgca tgccgacaac agcctctaca gatcccccca gacaattgac     420
gacgaaatcg ccgtcctgct gagcgacatc ctgcccaccg ccacgaaat cggcgtccag      480
tatgggaatg tccagccggg cgatgcggtg ctattgtcg gcgcgggccc cgtcggcatg      540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg gagtcgatgt tgcgatcgag     720
gcggtgggca taccggcgac ttgggacatc tgccaggaga tcgtcaagcc cggcgcgcac     780
atcgccaacg tcggcgtgca tggcgtcaag gttgacttcg agattcagaa gctctggatc     840
aagaacctga cgatcaccac gggactggtg aacacgaaca cgacgcccat gctgatgaag     900
gtcgcctcga ccgacaagct tccgttgaag aagatgatta cccatcgctt cgagctggcc     960
gagatcgagc acgcctatca ggtattcctc aatggcgcca aggagaaggc gatgaagatc    1020
atcctctcga acgcaggcgc tgcctga                                        1047
```

<210> SEQ ID NO 10
<211> LENGTH: 348
<212> TYPE: PRT
<213> ORGANISM: Achromobacter xylosoxidans

<400> SEQUENCE: 10

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
```

```
            180                 185                 190
Thr Ile Ile Val Ile Asp Met Asp Glu Asn Arg Leu Gln Leu Ala Lys
            195                 200                 205
Glu Leu Gly Ala Thr His Thr Ile Asn Ser Gly Thr Glu Asn Val Val
        210                 215                 220
Glu Ala Val His Arg Ile Ala Ala Glu Gly Val Asp Val Ala Ile Glu
225                 230                 235                 240
Ala Val Gly Ile Pro Ala Thr Trp Asp Ile Cys Gln Glu Ile Val Lys
                245                 250                 255
Pro Gly Ala His Ile Ala Asn Val Gly Val His Gly Val Lys Val Asp
            260                 265                 270
Phe Glu Ile Gln Lys Leu Trp Ile Lys Asn Leu Thr Ile Thr Thr Gly
        275                 280                 285
Leu Val Asn Thr Asn Thr Thr Pro Met Leu Met Lys Val Ala Ser Thr
        290                 295                 300
Asp Lys Leu Pro Leu Lys Lys Met Ile Thr His Arg Phe Glu Leu Ala
305                 310                 315                 320
Glu Ile Glu His Ala Tyr Gln Val Phe Leu Asn Gly Ala Lys Glu Lys
                325                 330                 335
Ala Met Lys Ile Ile Leu Ser Asn Ala Gly Ala Ala
            340                 345

<210> SEQ ID NO 11
<211> LENGTH: 643
<212> TYPE: DNA
<213> ORGANISM: Saccharomyces cerevisiae

<400> SEQUENCE: 11
gaaatgaata acaatactga cagtactaaa taattgccta cttggcttca catacgttgc     60
atacgtcgat atagataata atgataatga cagcaggatt atcgtaatac gtaatagttg    120
aaaatctcaa aaatgtgtgg gtcattacgt aaataatgat aggaatggga ttcttctatt    180
tttccttttt ccattctagc agccgtcggg aaaacgtggc atcctctctt tcgggctcaa    240
ttggagtcac gctgccgtga gcatcctctc tttccatatc taacaactga gcacgtaacc    300
aatggaaaag catgagctta gcgttgctcc aaaaaagtat tggatggtta ataccatttg    360
tctgttctct tctgactttg actcctcaaa aaaaaaaaat ctacaatcaa cagatcgctt    420
caattacgcc ctcacaaaaa cttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc ttttcttt    600
gtcatatata accataacca agtaatacat attcaaatct aga                     643

<210> SEQ ID NO 12
<211> LENGTH: 771
<212> TYPE: DNA
<213> ORGANISM: Klebsiella pneumoniae

<400> SEQUENCE: 12
atgaaaaaag tcgcacttgt taccggcgcc ggccagggga ttggtaaagc tatcgccctt     60
cgtctggtga aggatggatt tgccgtggcc attgccgatt ataacgacgc caccgccaaa    120
gcggtcgcct cggaaatcaa ccaggccggc ggacacgccg tggcggtgaa agtggatgtc    180
tccgaccgcg atcaggtatt tgccgccgtt aacaggcgc gcaaaacgct gggcggcttc    240
gacgtcatcg tcaataacgc cggtgtggca ccgtctacgc cgatcgagtc cattacccg    300
```

```
gagattgtcg acaaagtcta caacatcaac gtcaaagggg tgatctgggg tattcaggcg       360
gcggtcgagg cctttaagaa agagggcac ggcgggaaaa tcatcaacgc ctgttcccag        420
gccggccacg tcggcaaccc ggagctggcg gtgtatagct ccagtaaatt cgcggtacgc      480
ggcttaaccc agaccgccgc tcgcgacctc gcgccgctgg catcacggt caacggctac       540 tgcccgggga ttgtcaaaac gccaatgtgg gccgaaattg accgccaggt gtccgaagcc    600
gccggtaaac cgctgggcta cggtaccgcc gagttcgcca aacgcatcac tctcggtcgt    660
ctgtccgagc cggaagatgt cgccgcctgc gtctcctatc ttgccagccc ggattctgat     720
tacatgaccg gtcagtcgtt gctgatcgac ggcgggatgg tatttaacta a                 771
```

<210> SEQ ID NO 13
<211> LENGTH: 256
<212> TYPE: PRT
<213> ORGANISM: Klebsiella pneumoniae

<400> SEQUENCE: 13

```
Met Lys Lys Val Ala Leu Val Thr Gly Ala Gly Gln Gly Ile Gly Lys
  1               5                  10                  15

Ala Ile Ala Leu Arg Leu Val Lys Asp Gly Phe Ala Val Ala Ile Ala
             20                  25                  30

Asp Tyr Asn Asp Ala Thr Ala Lys Ala Val Ala Ser Glu Ile Asn Gln
         35                  40                  45

Ala Gly Gly His Ala Val Ala Val Lys Val Asp Val Ser Asp Arg Asp
     50                  55                  60

Gln Val Phe Ala Ala Val Glu Gln Ala Arg Lys Thr Leu Gly Gly Phe
 65                  70                  75                  80

Asp Val Ile Val Asn Asn Ala Gly Val Ala Pro Ser Thr Pro Ile Glu
                 85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 14
<211> LENGTH: 753
<212> TYPE: DNA
<213> ORGANISM: Saccharomyces cerevisiae

<400> SEQUENCE: 14

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatagccata     300
gtgatgtcta agtaacccttt atggtatatt tcttaatgtg gaaagatact agcgcgcgca     360
cccacacaca agcttcgtct tttcttgaag aaaagaggaa gctcgctaaa tgggattcca     420
cttttccgttc cctgccagct gatggaaaaa ggttagtgga acgatgaaga ataaaagag     480
agatccactg aggtgaaatt tcagctgaca gcgagtttca tgatcgtgat gaacaatggt     540
aacgagttgt ggctgttgcc agggagggtg gttctcaact tttaatgtat ggccaaatcg     600
ctacttgggt ttgttatata caaagaaga ataatgaac tgattctctt cctccttctt     660
gtcctttctt aattctgttg taattacctt cctttgtaat tttttttgta attattcttc     720
ttaataatcc aaacaaacac acatattaca ata                                 753
```

<210> SEQ ID NO 15
<211> LENGTH: 2532
<212> TYPE: DNA
<213> ORGANISM: Roseburia inulinivorans

<400> SEQUENCE: 15

```
atgggcaatt acgattcaac accgatagct aaaagtgata ggattaaaag attggttgat      60
catttgtatg ctaaaatgcc tgaaattgag gccgctagag cagagctaat tactgaatcc     120
tttaaggcca ccgaaggtca acctgttgtt atgagaaagg ctagagcttt tgaacatata     180
ctaaagaatt tgccaattat cataagacca gaagaactga ttgttggctc aactacaatt     240
gccctagag gttgccaaac gtatccagaa ttctcatacg agtggttaga ggctgaattt     300
gaaactgtcg aaacgcgttc agctgaccca ttttatattt cagaagaaac gaagaaacgt     360
ttgctggctg ccgatgctta ttggaaaggt aaaacaaccct cagagttggc aacttcatat     420
atggccccag aaactctaag agccatgaag cataacttct tcacccctgg aaactacttc     480
tacaatggtc tcggtcatgt cacagttcaa atgaaacag tattagcaat cggcttgaat     540
ggagtaaaag agaaggttag gaaagagatg gagaattgtc attttggtga tgccgattat     600
agtacaaaga tgtgttttct ggagagcatt ttaatatcgt gtgatgccgt aatcacttat     660
gctaatagat atgccaagat ggccgaggaa atggctgaaa agaaacaga tgctgcaagg     720
aggcaagaac tattaacaat cgccagggtt tgcaaaaacg ttcctgaatt cccagccgaa     780
agcttccagg aggcctgcca atccttttgg ttcatacaac aagtgcttca aattgaatcc     840
agtggtcatt caatttcccc aggtagattt gatcaatata tgtatcctta ttacgaaaag     900
gatttaaagg aaggtagctt aactaggaa atgctcagg aactgatcga ttgtatctgg     960
gttaagttaa atgatctgaa taagtgcagg gatgctgcct ctgctgaggg ctttgcagga    1020
tattccttat ttcaaaactt aatcgttggg gccaaacgg ttcaaggaag gacgccacc    1080
aatgatttga gttttatgtg tatcacggca tctgaacacg tctttttacc gatgccgtcg    1140
ttgtctataa gagtttggca tggtagttcc aaagcactgc ttatgagagc agctgaattg    1200
actagaaccg gtataggctt acctgcttat tacaatgatg aagtcatcat accagctttg    1260
gtgcataggg gtgctactat ggatgaagca agaaattaca acataatagg atgtgtcgaa    1320
```

```
ccgcaggttc ctggtaaaac tgatggctgg cacgatgcag cattctttaa catgtgcaga    1380
cctttggaaa tggtgtttag taatggttat gataacggtg aaattgcatc tatacaaact    1440
ggtaacgtag aatcttttca gagttttgat gagtttatgg aagcttacag aaaacaaatg    1500
ctatataaca tagaacttat ggtaaatgcc gacaacgcga tagattatgc ccacgcaaag    1560
ttggccccat tgccatttga gtcatgtttg gttgatgact gtataaagag aggaatgtcc    1620
gctcaggaag gcggcgcaat ctataatttc actggtccac agggctttgg tattgcaaac    1680
gttgctgata gcttgtatac gattaagaaa ttggtgttcg aggagaagag aattacgatg    1740
ggtgaattaa agaaagcgtt ggaaatgaat tatggtaagg gtttggatgc cacaaccgct    1800
ggtgacatcg caatgcaggt cgcgaaggga ctaaagatg ccggacagga agtgggtccc     1860
gacgtgatcg ctaatacaat ccgtcaagtt cttgaaatgg aattaccaga agatgtaaga    1920
aagagatatg aagagatcca tgaaatgata cttgagttac caaagtatgg taatgatata    1980
gatgaagttg atgaattagc tagagaagca gcttactttt acacaagacc attagaaact    2040
tttaagaatc caagggggtgg catgtatcaa gccggccttt atcccgtgtc cgctaatgtg    2100
ccactaggcg ctcaaacggg ggccacaccc gatggacgtt tggcgcatac acccgtggcg    2160
gatggcgttg gtccgacatc aggcttcgat atatccggac caacagcttc ttgcaattct    2220
gtcgccaagt tggatcatgc tatagcctct aatggtacct tatttaatat gaagatgcac    2280
ccaaccgcaa tggcaggtga aaagggctta gaatccttca tatcgttgat ccgtggttat    2340
ttcgatcaac aagtatgca catgcaattt aacgtagtag acagggctac actgcttgat    2400
gcgcaggccc acccctgaaaa gtattcaggc ttaattgtca gagtggcagg ttattctgcc    2460 cttttttacca cattgtccaa gtcattacaa gatgatataa tcaaacgtac cgaacaagca    2520
gacaatagat ag                                                        2532
```

<210> SEQ ID NO 16
<211> LENGTH: 843
<212> TYPE: PRT
<213> ORGANISM: Roseburia inulinivorans

<400> SEQUENCE: 16

```
Met Gly Asn Tyr Asp Ser Thr Pro Ile Ala Lys Ser Asp Arg Ile Lys
1               5                   10                  15

Arg Leu Val Asp His Leu Tyr Ala Lys Met Pro Glu Ile Glu Ala Ala
                20                  25                  30

Arg Ala Glu Leu Ile Thr Glu Ser Phe Lys Ala Thr Glu Gly Gln Pro
            35                  40                  45

Val Val Met Arg Lys Ala Arg Ala Phe Glu His Ile Leu Lys Asn Leu
        50                  55                  60

Pro Ile Ile Ile Arg Pro Glu Leu Ile Val Gly Ser Thr Thr Ile
65                  70                  75                  80

Ala Pro Arg Gly Cys Gln Thr Tyr Pro Glu Phe Ser Tyr Glu Trp Leu
                85                  90                  95

Glu Ala Glu Phe Glu Thr Val Glu Thr Arg Ser Ala Asp Pro Phe Tyr
                100                 105                 110

Ile Ser Glu Glu Thr Lys Lys Arg Leu Leu Ala Ala Asp Ala Tyr Trp
            115                 120                 125

Lys Gly Lys Thr Thr Ser Glu Leu Ala Thr Ser Tyr Met Ala Pro Glu
        130                 135                 140

Thr Leu Arg Ala Met Lys His Asn Phe Phe Thr Pro Gly Asn Tyr Phe
```

```
145                 150                 155                 160
Tyr Asn Gly Val Gly His Val Thr Val Gln Tyr Glu Thr Val Leu Ala
                165                 170                 175
Ile Gly Leu Asn Gly Val Lys Glu Lys Val Arg Lys Glu Met Glu Asn
                180                 185                 190
Cys His Phe Gly Asp Ala Asp Tyr Ser Thr Lys Met Cys Phe Leu Glu
                195                 200                 205
Ser Ile Leu Ile Ser Cys Asp Ala Val Ile Thr Tyr Ala Asn Arg Tyr
            210                 215                 220
Ala Lys Met Ala Glu Met Ala Glu Lys Glu Thr Asp Ala Ala Arg
225                 230                 235                 240
Arg Gln Glu Leu Leu Thr Ile Ala Arg Val Cys Lys Asn Val Pro Glu
                245                 250                 255
Phe Pro Ala Glu Ser Phe Gln Glu Ala Cys Gln Ser Phe Trp Phe Ile
                260                 265                 270
Gln Gln Val Leu Gln Ile Glu Ser Ser Gly His Ser Ile Ser Pro Gly
                275                 280                 285
Arg Phe Asp Gln Tyr Met Tyr Pro Tyr Tyr Glu Lys Asp Leu Lys Glu
                290                 295                 300
Gly Ser Leu Thr Arg Glu Tyr Ala Gln Glu Leu Ile Asp Cys Ile Trp
305                 310                 315                 320
Val Lys Leu Asn Asp Leu Asn Lys Cys Arg Asp Ala Ala Ser Ala Glu
                325                 330                 335
Gly Phe Ala Gly Tyr Ser Leu Phe Gln Asn Leu Ile Val Gly Gly Gln
                340                 345                 350
Thr Val Gln Gly Arg Asp Ala Thr Asn Asp Leu Ser Phe Met Cys Ile
                355                 360                 365
Thr Ala Ser Glu His Val Phe Leu Pro Met Pro Ser Leu Ser Ile Arg
            370                 375                 380
Val Trp His Gly Ser Ser Lys Ala Leu Leu Met Arg Ala Ala Glu Leu
385                 390                 395                 400
Thr Arg Thr Gly Ile Gly Leu Pro Ala Tyr Tyr Asn Asp Glu Val Ile
                405                 410                 415
Ile Pro Ala Leu Val His Arg Gly Ala Thr Met Asp Glu Ala Arg Asn
                420                 425                 430
Tyr Asn Ile Ile Gly Cys Val Glu Pro Gln Val Pro Gly Lys Thr Asp
                435                 440                 445
Gly Trp His Asp Ala Ala Phe Phe Asn Met Cys Arg Pro Leu Glu Met
450                 455                 460
Val Phe Ser Asn Gly Tyr Asp Asn Gly Glu Ile Ala Ser Ile Gln Thr
465                 470                 475                 480
Gly Asn Val Glu Ser Phe Gln Ser Phe Asp Glu Phe Met Glu Ala Tyr
                485                 490                 495
Arg Lys Gln Met Leu Tyr Asn Ile Glu Leu Met Val Asn Ala Asp Asn
                500                 505                 510
Ala Ile Asp Tyr Ala His Ala Lys Leu Ala Pro Leu Pro Phe Glu Ser
            515                 520                 525
Cys Leu Val Asp Asp Cys Ile Lys Arg Gly Met Ser Ala Gln Glu Gly
            530                 535                 540
Gly Ala Ile Tyr Asn Phe Thr Gly Pro Gln Gly Phe Gly Ile Ala Asn
545                 550                 555                 560
Val Ala Asp Ser Leu Tyr Thr Ile Lys Lys Leu Val Phe Glu Glu Lys
                565                 570                 575
```

Arg Ile Thr Met Gly Glu Leu Lys Lys Ala Leu Glu Met Asn Tyr Gly
            580                 585                 590

Lys Gly Leu Asp Ala Thr Thr Ala Gly Asp Ile Ala Met Gln Val Ala
        595                 600                 605

Lys Gly Leu Lys Asp Ala Gly Gln Glu Val Gly Pro Asp Val Ile Ala
    610                 615                 620

Asn Thr Ile Arg Gln Val Leu Glu Met Glu Leu Pro Glu Asp Val Arg
625                 630                 635                 640

Lys Arg Tyr Glu Glu Ile His Glu Met Ile Leu Glu Leu Pro Lys Tyr
                645                 650                 655

Gly Asn Asp Ile Asp Glu Val Asp Glu Leu Ala Arg Glu Ala Ala Tyr
            660                 665                 670

Phe Tyr Thr Arg Pro Leu Glu Thr Phe Lys Asn Pro Arg Gly Gly Met
        675                 680                 685

Tyr Gln Ala Gly Leu Tyr Pro Val Ser Ala Asn Val Pro Leu Gly Ala
    690                 695                 700

Gln Thr Gly Ala Thr Pro Asp Gly Arg Leu Ala His Thr Pro Val Ala
705                 710                 715                 720

Asp Gly Val Gly Pro Thr Ser Gly Phe Asp Ile Ser Gly Pro Thr Ala
                725                 730                 735

Ser Cys Asn Ser Val Ala Lys Leu Asp His Ala Ile Ala Ser Asn Gly
            740                 745                 750

Thr Leu Phe Asn Met Lys Met His Pro Thr Ala Met Ala Gly Glu Lys
        755                 760                 765

Gly Leu Glu Ser Phe Ile Ser Leu Ile Arg Gly Tyr Phe Asp Gln Gln
    770                 775                 780

Gly Met His Met Gln Phe Asn Val Val Asp Arg Ala Thr Leu Leu Asp
785                 790                 795                 800

Ala Gln Ala His Pro Glu Lys Tyr Ser Gly Leu Ile Val Arg Val Ala
                805                 810                 815

Gly Tyr Ser Ala Leu Phe Thr Thr Leu Ser Lys Ser Leu Gln Asp Asp
            820                 825                 830

Ile Ile Lys Arg Thr Glu Gln Ala Asp Asn Arg
        835                 840

<210> SEQ ID NO 17
<211> LENGTH: 794
<212> TYPE: DNA
<213> ORGANISM: Roseburia inulinivorans

<400> SEQUENCE: 17
atgaaagaat atcttaatac ttcaggtaga atatttgata tccagaggta ttctattcac     60
gatggccctg gtgtgcgtac aattgtgttt ctaaaaggtt gtgcccttag atgcagatgg    120
tgctgtaatc ctgaaagcca aagcttcgaa gttgaaacaa tgacgattaa tggaaaacct    180
aaagtcatgg gtaaagatgt tacagtcgcc gaggttatga agacggtaga agagacatg     240 ccttattacc ttcaatcagg tggtggtatc accttatcgg gtggcgaatg tactttgcaa    300
ccagaatttt cccttggcct attgagagct gcaaaggatt gggcatatc cacggcaata    360 gagagcatgg cgtacgcaaa gtacgaagta atagaaactc ttcttccgta tttggatacg    420
tatttaatgg acatcaaaca tatgaatcct gagaaacata agaatacac tggtcatgat    480 aacttgagga tgttagaaaa cgccttaaga gtcgcgcatt ctggtcagac cgaactgatc    540
atcagagtac ctgtcatccc aggattcaac gcaactgagc aggaactact agatattgca    600

```
aaattcgcag atacactgcc tggagttaga caaatacaca tcttgccata tcataatttt    660
ggtcagggta atacgaagg attgaacagg gactatccga tgggggacac tgagaaaccc    720
tctaatgaac agatgaaagc ttttcaagaa atgattcaaa gaacacttcc cctacattgc    780
caaatcggtg gtta                                                      794
```

```
<210> SEQ ID NO 18
<211> LENGTH: 264
<212> TYPE: PRT
<213> ORGANISM: Roseburia inulinivorans

<400> SEQUENCE: 18
```

| Met | Lys | Glu | Tyr | Leu | Asn | Thr | Ser | Gly | Arg | Ile | Phe | Asp | Ile | Gln | Arg |
|---|---|---|---|---|---|---|---|---|---|---|---|---|---|---|---|
| 1 | | | | 5 | | | | | 10 | | | | | 15 | |

Tyr Ser Ile His Asp Gly Pro Gly Val Arg Thr Ile Val Phe Leu Lys
            20                  25                  30

Gly Cys Ala Leu Arg Cys Arg Trp Cys Cys Asn Pro Glu Ser Gln Ser
        35                  40                  45

Phe Glu Val Glu Thr Met Thr Ile Asn Gly Lys Pro Lys Val Met Gly
    50                  55                  60

Lys Asp Val Thr Val Ala Glu Val Met Lys Thr Val Glu Arg Asp Met
65                  70                  75                  80

Pro Tyr Tyr Leu Gln Ser Gly Gly Ile Thr Leu Ser Gly Gly Glu
                85                  90                  95

Cys Thr Leu Gln Pro Glu Phe Ser Leu Gly Leu Leu Arg Ala Ala Lys
            100                 105                 110

Asp Leu Gly Ile Ser Thr Ala Ile Glu Ser Met Ala Tyr Ala Lys Tyr
        115                 120                 125

Glu Val Ile Glu Thr Leu Leu Pro Tyr Leu Asp Thr Tyr Leu Met Asp
    130                 135                 140

Ile Lys His Met Asn Pro Glu Lys His Lys Glu Tyr Thr Gly His Asp
145                 150                 155                 160

Asn Leu Arg Met Leu Glu Asn Ala Leu Arg Val Ala His Ser Gly Gln
                165                 170                 175

Thr Glu Leu Ile Ile Arg Val Pro Val Ile Pro Gly Phe Asn Ala Thr
            180                 185                 190

Glu Gln Glu Leu Leu Asp Ile Ala Lys Phe Ala Asp Thr Leu Pro Gly
        195                 200                 205

Val Arg Gln Ile His Ile Leu Pro Tyr His Asn Phe Gly Gln Gly Lys
    210                 215                 220

Tyr Glu Gly Leu Asn Arg Asp Tyr Pro Met Gly Asp Thr Glu Lys Pro
225                 230                 235                 240

Ser Asn Glu Gln Met Lys Ala Phe Gln Glu Met Ile Gln Lys Asn Thr
                245                 250                 255

Ser Leu His Cys Gln Ile Gly Gly
            260

```
<210> SEQ ID NO 19
<211> LENGTH: 978
<212> TYPE: DNA
<213> ORGANISM: Lactococcus lactis

<400> SEQUENCE: 19
```

```
atggctgata acaacgtaa aaaagttatc cttgtaggtg acggtgctgt aggttcatca     60
tacgcttttg ctcttgtaaa ccaagggatt gcacaagaat taggaattgt tgaccttttt    120
```

```
aagaaaaaa ctcaaggaga tgcagaagac ctttctcatg ccttggcatt tacttcacct        180
aaaaagattt actctgcaga ctactctgat gcaagcgacg ctgacctcgt agtcttgact        240
tctggtgctc cacaaaaacc aggtgaaact cgtcttgacc ttgttgaaaa aaatcttcgt        300
atcactaaag atgttgtcac taaaattgtt gcttcaggtt tcaaaggaat cttccttgtt        360
gctgctaacc cagttgatat cttgacatac gctacttgga aattctcagg tttccctaaa        420
aaccgcgtta taggttcagg tacttcactt gatactgcac gtttccgtca agcattggca        480
gaaaaagttg atgttgacgc tcgttcaatc cacgcataca tcatgggtga acacggtgac        540
tcagaatttg ccgtttggtc acacgctaac gttgctggtg ttaaattgga acaatggttc        600
caagaaaatg actaccttaa cgaagctgaa atcgttgaat tgtttgaatc tgtacgtgat        660
gctgcttact caatcatcgc taaaaaaggt gcaacattct atggtgtcgc tgtagctctt        720
gctcgtatta ctaaagcaat tcttgatgat gaacatgcag tacttccagt atcagtattc        780
caagatggac aatatggcgt aagcgactgc taccttggtc aaccagctgt agttggtgct        840
gaaggtgttg ttaacccaat ccacattcca ttgaatgatg ctgaaatgca aaaaatggaa        900
gcttctggtg ctcaattgaa agcaatcatt gacgaagctt ttgctaaaga gaatttgct        960 tctgcagtta aaaactaa                                                     978

<210> SEQ ID NO 20
<211> LENGTH: 325
<212> TYPE: PRT
<213> ORGANISM: Lactococcus lactis

<400> SEQUENCE: 20

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
                20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
                100                 105                 110

Gly Phe Lys Gly Ile Phe Leu Val Ala Ala Asn Pro Val Asp Ile Leu
            115                 120                 125

Thr Tyr Ala Thr Trp Lys Phe Ser Gly Phe Pro Lys Asn Arg Val Val
130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
```

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
            245                 250                 255

Val Ser Val Phe Gln Asp Gly Gln Tyr Gly Val Ser Asp Cys Tyr Leu
        260                 265                 270

Gly Gln Pro Ala Val Gly Ala Glu Gly Val Val Asn Pro Ile His
    275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
            325

<210> SEQ ID NO 21
<211> LENGTH: 996
<212> TYPE: DNA
<213> ORGANISM: Leuconostoc mesenteroides

<400> SEQUENCE: 21
atgaagattt ttgcttacgg cattcgtgat gatgaaaagc catcacttga agaatggaaa      60
gcggctaacc cagagattga agtggactac acacaagaat tattgacacc tgaaacagct     120
aagttggctg agggatcaga ttcagctgtt gtttatcaac aattggacta tacacgtgaa     180
acattgacag ctttagctaa cgttggtgtt actaacttgt cattgcgtaa cgttggtaca     240
gataacattg attttgatgc agcacgtgaa tttaacttta acatttcaaa tgttcctgtt     300
tattcaccaa atgctattgc agaacactca atgattcaat tatctcgttt gctacgtcgc     360
acgaaagcat ggatgccaaa attgctaag cacgacttgc gttgggcacc aacaattgga     420
cgtgaaatgc gtatgcaaac agttggtgtt attggtacag gtcatattgg ccgtgttgct     480
attaacattt tgaaaggctt tgggccaag gttattgctt atgacaagta cccaaatgct     540
gaattacaag cagaaggttt gtacgttgac acattagacg aattatatgc acaagctgat     600
gcaatttcat tgtatgttcc tggtgtacct gaaaaccatc atctaatcaa tgcagatgct     660
attgctaaga tgaaggatgg tgtggttatc atgaacgctc gcgtggtaa tttgatggac     720
attgacgcta ttattgatgg tttgaattct ggtaagattt cagacttcgg tatggacgtt     780
tatgaaaatg aagttggctt gttcaatgaa gattggtctg gtaaagaatt cccagatgct     840
aagattgctg acttgattgc acgcgaaaat gtattggtta cgccacacac ggctttctat     900
acaactaaag ctgttctaga aatggttcac caatcatttg atgcagcagt tgctttcgcc     960
aagggtgaga agccagctat tgctgttgaa tattaa                              996

<210> SEQ ID NO 22
<211> LENGTH: 331
<212> TYPE: PRT
<213> ORGANISM: Leuconostoc mesenteroides

<400> SEQUENCE: 22

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

```
Glu Leu Leu Thr Pro Glu Thr Ala Lys Leu Ala Glu Gly Ser Asp Ser
             35                  40                  45

Ala Val Val Tyr Gln Gln Leu Asp Tyr Thr Arg Glu Thr Leu Thr Ala
 50                  55                  60

Leu Ala Asn Val Gly Val Thr Asn Leu Ser Leu Arg Asn Val Gly Thr
 65                  70                  75                  80

Asp Asn Ile Asp Phe Asp Ala Ala Arg Glu Phe Asn Phe Asn Ile Ser
                 85                  90                  95

Asn Val Pro Val Tyr Ser Pro Asn Ala Ile Ala Glu His Ser Met Ile
                100                 105                 110

Gln Leu Ser Arg Leu Leu Arg Arg Thr Lys Ala Leu Asp Ala Lys Ile
                115                 120                 125

Ala Lys His Asp Leu Arg Trp Ala Pro Thr Ile Gly Arg Glu Met Arg
            130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
            195                 200                 205

Val Pro Glu Asn His His Leu Ile Asn Ala Asp Ala Ile Ala Lys Met
            210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ala Arg
            275                 280                 285

Glu Asn Val Leu Val Thr Pro His Thr Ala Phe Tyr Thr Thr Lys Ala
290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
            325                 330

<210> SEQ ID NO 23
<211> LENGTH: 987
<212> TYPE: DNA
<213> ORGANISM: Streptococcus thermophilus

<400> SEQUENCE: 23
atgactgcaa ctaaactaca caaaaaagtc atccttgttg gtgacggtgc cgtaggttca      60
tcttacgctt tcgcacttgt aaaccaaggt atcgctcaag aactaggtat catcgaaatt     120
ccacaattat ttgaaaaagc cgttggtgat gcgcttgacc ttagccacgc acttcctttc     180
acttcaccta aaaaaatcta tgcagctaaa tatgaagact gtgcggatgc tgaccttgta     240
gttatcactg ctggtgctcc tcaaaaacca ggtgagactc gtcttgatct tgttggtaaa     300
aaccttgcaa tcaacaaatc aatcgttact caagttgttg aatcaggatt caacggtatt     360
ttccttgtag ctgctaaccc agtagacgta ttgacttact ctacatggaa gttctcagga     420
```

```
ttccctaaag aacgcgttat cggttcaggt acttcacttg actcagctcg tttccgtcaa    480
gcacttgctg aaaaacttaa tgtcgatgct cgttcagttc acgcttacat catgggtgaa    540
cacggcgact cagagtttgc ggtttggtca cacgctaaca tcgccggtgt aaaccttgaa    600
gagttcctta agacgaaga aaacgttcaa gaagctgaat tagttgaatt gttcgaaggt    660
gttcgtgatg cagcttacac aattatcaac aaaaaaggtg ctacatacta cggtatcgca    720
gtagcccttg ctcgtatcac taaagctatc cttgacgatg aaaatgcagt acttccattg    780
tctgtattcc aagaaggtca atatggtgta acaacatct ttatcggtca acctgctatt    840
gtaggcgcac acggtatcgt acgtccagta aacatcccat gaacgatgc tgaacaacaa    900
aagatgaagg cttctgccga tgaattgcaa gctatcattg atgaagcatg gaaaaaccct    960
gaattccaag aagcttcaaa aaactaa                                         987

<210> SEQ ID NO 24
<211> LENGTH: 328
<212> TYPE: PRT
<213> ORGANISM: Streptococcus thermophilus

<400> SEQUENCE: 24

Met Thr Ala Thr Lys Leu His Lys Lys Val Ile Leu Val Gly Asp Gly
1               5                   10                  15

Ala Val Gly Ser Ser Tyr Ala Phe Ala Leu Val Asn Gln Gly Ile Ala
            20                  25                  30

Gln Glu Leu Gly Ile Ile Glu Ile Pro Gln Leu Phe Glu Lys Ala Val
        35                  40                  45

Gly Asp Ala Leu Asp Leu Ser His Ala Leu Pro Phe Thr Ser Pro Lys
    50                  55                  60

Lys Ile Tyr Ala Ala Lys Tyr Glu Asp Cys Ala Asp Ala Asp Leu Val
65                  70                  75                  80

Val Ile Thr Ala Gly Ala Pro Gln Lys Pro Gly Glu Thr Arg Leu Asp
                85                  90                  95

Leu Val Gly Lys Asn Leu Ala Ile Asn Lys Ser Ile Val Thr Gln Val
            100                 105                 110

Val Glu Ser Gly Phe Asn Gly Ile Phe Leu Val Ala Ala Asn Pro Val
        115                 120                 125

Asp Val Leu Thr Tyr Ser Thr Trp Lys Phe Ser Gly Phe Pro Lys Glu
    130                 135                 140

Arg Val Ile Gly Ser Gly Thr Ser Leu Asp Ser Ala Arg Phe Arg Gln
145                 150                 155                 160

Ala Leu Ala Glu Lys Leu Asn Val Asp Ala Arg Ser Val His Ala Tyr
                165                 170                 175

Ile Met Gly Glu His Gly Asp Ser Glu Phe Ala Val Trp Ser His Ala
            180                 185                 190

Asn Ile Ala Gly Val Asn Leu Glu Glu Phe Leu Lys Asp Glu Glu Asn
        195                 200                 205

Val Gln Glu Ala Glu Leu Val Glu Leu Phe Glu Gly Val Arg Asp Ala
    210                 215                 220

Ala Tyr Thr Ile Ile Asn Lys Lys Gly Ala Thr Tyr Tyr Gly Ile Ala
225                 230                 235                 240

Val Ala Leu Ala Arg Ile Thr Lys Ala Ile Leu Asp Asp Glu Asn Ala
                245                 250                 255

Val Leu Pro Leu Ser Val Phe Gln Glu Gly Gln Tyr Gly Val Asn Asn
            260                 265                 270
```

```
Ile Phe Ile Gly Gln Pro Ala Ile Val Gly Ala His Gly Ile Val Arg
            275                 280                 285

Pro Val Asn Ile Pro Leu Asn Asp Ala Glu Gln Lys Met Lys Ala
        290                 295                 300

Ser Ala Asp Glu Leu Gln Ala Ile Ile Asp Glu Ala Trp Lys Asn Pro
305                 310                 315                 320

Glu Phe Gln Glu Ala Ser Lys Asn
                325

<210> SEQ ID NO 25
<211> LENGTH: 996
<212> TYPE: DNA
<213> ORGANISM: Pediococcus pentosaceus

<400> SEQUENCE: 25
atgaaaatta ttgcttatgg cattcgagat gacgaaaaac cttacctaga agaatgggtt      60
aaagataata aaattgaagt aaaggctgtt agcgaattgt tggactccaa cacgattgaa     120
caagctaagg gttatgacgg agttgttgca atcaacagaa accttatac agatgatttg      180 ttcgataaaa tgaatgaatt cgggattcat gccttttcgc ttcgtaacgt tggtgttgat     240
aatgttccag ttgaggcttt aaagcgaaat aatattaaga ttaccaatgt tccagcgtac     300
tctccaatgg cgattgcaga actttcagta acccaactcc tagctttaat cgtcgaatt      360 ccagaatttg atgctaagat ggctcgtggt gatttcagat gggaaccaga tattgctcta     420
gaacttaacc aaatgacagt aggagttatt ggtaccggaa gaattgggcg tgcggccatt     480
aatatcttta aaggctttgg agctaaagtg attgcttatg atgttttccg aaattcagaa     540
cttgaaaaag aaggaatcta tgttgactcg cttgaagaac tttatcgtca agtagatgtt     600
attaccttac atgttcccgc tttaaaagat aactaccata tgttaaatga tgaagcgttc     660
gcacagatgc atgatggggt atttgttcta aattttgctc gcggtagctt gattgacacg     720
aaggcattac ttaaggcttt agatagtggt aaggtggctg gtgcggcact agataccta     780 gaagacgaag taggtatttt tgatgtggat caccaaaatg acccaatcaa tgatcccgta     840
tttaatgatt tatacagtag acgtaatgta aaaatcacac acatgcggc ttttttatact     900 aagccagcag ttaaaaatat ggtacaaatt gctcttgaaa ataataaagc actaattgaa     960
aaaggtgctg caagaaatga agttaagttt gactaa                              996

<210> SEQ ID NO 26
<211> LENGTH: 331
<212> TYPE: PRT
<213> ORGANISM: Pediococcus pentosaceus

<400> SEQUENCE: 26

Met Lys Ile Ile Ala Tyr Gly Ile Arg Asp Asp Glu Lys Pro Tyr Leu
1               5                   10                  15

Glu Glu Trp Val Lys Asp Asn Lys Ile Glu Val Lys Ala Val Ser Glu
            20                  25                  30

Leu Leu Asp Ser Asn Thr Ile Glu Gln Ala Lys Gly Tyr Asp Gly Val
        35                  40                  45

Val Ala Tyr Gln Gln Lys Pro Tyr Thr Asp Asp Leu Phe Asp Lys Met
    50                  55                  60

Asn Glu Phe Gly Ile His Ala Phe Ser Leu Arg Asn Val Gly Val Asp
65                  70                  75                  80

Asn Val Pro Val Glu Ala Leu Lys Arg Asn Asn Ile Lys Ile Thr Asn
                85                  90                  95
```

Val Pro Ala Tyr Ser Pro Met Ala Ile Ala Glu Leu Ser Val Thr Gln
                100                 105                 110

Leu Leu Ala Leu Ile Arg Arg Ile Pro Glu Phe Asp Ala Lys Met Ala
            115                 120                 125

Arg Gly Asp Phe Arg Trp Glu Pro Asp Ile Ala Leu Glu Leu Asn Gln
        130                 135                 140

Met Thr Val Gly Val Ile Gly Thr Gly Arg Ile Gly Arg Ala Ala Ile
145                 150                 155                 160

Asn Ile Phe Lys Gly Phe Gly Ala Lys Val Ile Ala Tyr Asp Val Phe
                165                 170                 175

Arg Asn Ser Glu Leu Glu Lys Glu Gly Ile Tyr Val Asp Ser Leu Glu
            180                 185                 190

Glu Leu Tyr Arg Gln Val Asp Val Ile Thr Leu His Val Pro Ala Leu
        195                 200                 205

Lys Asp Asn Tyr His Met Leu Asn Asp Glu Ala Phe Ala Gln Met His
210                 215                 220

Asp Gly Val Phe Val Leu Asn Phe Ala Arg Gly Ser Leu Ile Asp Thr
225                 230                 235                 240

Lys Ala Leu Leu Lys Ala Leu Asp Ser Gly Lys Val Ala Gly Ala Ala
                245                 250                 255

Leu Asp Thr Tyr Glu Asp Glu Val Gly Ile Phe Asp Val Asp His Gln
            260                 265                 270

Asn Asp Pro Ile Asn Asp Pro Val Phe Asn Asp Leu Tyr Ser Arg Arg
        275                 280                 285

Asn Val Lys Ile Thr Pro His Ala Ala Phe Tyr Thr Lys Pro Ala Val
            290                 295                 300

Lys Asn Met Val Gln Ile Ala Leu Glu Asn Asn Lys Ala Leu Ile Glu
305                 310                 315                 320

Lys Gly Ala Ala Arg Asn Glu Val Lys Phe Asp
                325                 330

<210> SEQ ID NO 27
<211> LENGTH: 1110
<212> TYPE: DNA
<213> ORGANISM: Pediococcus pentosaceus

<400> SEQUENCE: 27
atgacaatga ttaatggtta tgaacaaagt gatcgtgaag aaaaaattga catttaaat      60 ttggagtctt tggaagaaag agccgaaaag attattccaa ctggtgggtt tggatatatc   120
tctggtggtt ctgaagatga atggactctc cgacaaaatc gaactgcatt ccagcatcga   180 caatcgcgc ccaaagcttt gagtggaatt gaaaaaccag aactaaatac agaaatcttt    240
ggaattccat tgaatactcc agtgatgatg gcgccagctg cagctcaagg cttagcacat   300
tcacaaggtg aaaagatac agctagaggt cttgccgcag taggaggctt aatggcacaa    360
agcacatatt catcagtttc tattgctgat acggcagctg ctggtgaagg tgctcctcaa   420 ttttttccagc tttacatgag taaggactgg aattttaatg agagcttgct agatgaggct   480
aaaaaagctc atgttaaagc aattatttg accgtagatg ccactgttga tggttatcga    540
gaagctgata ttaaaaataa gtttgcattt ccacttccaa tggctaactt aactaagttt   600
tccgagggtg atggtcaagg aaaggaatt gaagaaatct acgcttctgc agctcaaaat    660
ataagaccgg aagatgttag aagaattgct gattacacac aattaccgt aattgttaaa   720 ggaattcaaa ctcctgagga tgctattcga gcaattgatg ctggggcagc cggcatttat   780

```
gtatcaaacc atggaggtcg tcagctaaac gggggacctg gatcttttga tgttttggaa    840
gatatcgcta cctccgttaa taagcaggtg ccaattatct ttgatagtgg tgtacgtcgt    900
ggttcagatg tatttaaagc tttggctagt ggcgcagaca tcgtggcttt gggtcgtcca    960
gtaatttatg gattagcttt aggtggtgcc aaagggggttc aatctgtatt tgaacatata   1020
gaccatgaac ttgaaattgt gatgcaacta gcaggtacta aaccattga tgatattaaa    1080 aataacccac tactaaacat caaatattaa                                     1110
```

<210> SEQ ID NO 28
<211> LENGTH: 369
<212> TYPE: PRT
<213> ORGANISM: Pediococcus pentosaceus

<400> SEQUENCE: 28

```
Met Thr Met Ile Asn Gly Tyr Glu Gln Ser Asp Arg Glu Glu Lys Ile
1               5                   10                  15

Asp Ile Leu Asn Leu Glu Ser Leu Glu Glu Arg Ala Glu Lys Ile Ile
            20                  25                  30

Pro Thr Gly Gly Phe Gly Tyr Ile Ser Gly Gly Ser Glu Asp Glu Trp
        35                  40                  45

Thr Leu Arg Gln Asn Arg Thr Ala Phe Gln His Arg Gln Ile Ala Pro
    50                  55                  60

Lys Ala Leu Ser Gly Ile Glu Lys Pro Glu Leu Asn Thr Glu Ile Phe
65                  70                  75                  80

Gly Ile Pro Leu Asn Thr Pro Val Met Met Ala Pro Ala Ala Gln
                85                  90                  95

Gly Leu Ala His Ser Gln Gly Glu Lys Asp Thr Ala Arg Gly Leu Ala
            100                 105                 110

Ala Val Gly Gly Leu Met Ala Gln Ser Thr Tyr Ser Ser Val Ser Ile
        115                 120                 125

Ala Asp Thr Ala Ala Ala Gly Glu Gly Ala Pro Gln Phe Phe Gln Leu
    130                 135                 140

Tyr Met Ser Lys Asp Trp Asn Phe Asn Glu Ser Leu Leu Asp Glu Ala
145                 150                 155                 160

Lys Lys Ala His Val Lys Ala Ile Ile Leu Thr Val Asp Ala Thr Val
                165                 170                 175

Asp Gly Tyr Arg Glu Ala Asp Ile Lys Asn Lys Phe Ala Phe Pro Leu
            180                 185                 190

Pro Met Ala Asn Leu Thr Lys Phe Ser Glu Gly Asp Gly Gln Gly Lys
        195                 200                 205

Gly Ile Glu Glu Ile Tyr Ala Ser Ala Ala Gln Asn Ile Arg Pro Glu
    210                 215                 220

Asp Val Arg Arg Ile Ala Asp Tyr Thr Gln Leu Pro Val Ile Val Lys
225                 230                 235                 240

Gly Ile Gln Thr Pro Glu Asp Ala Ile Arg Ala Ile Asp Ala Gly Ala
                245                 250                 255

Ala Gly Ile Tyr Val Ser Asn His Gly Gly Arg Gln Leu Asn Gly Gly
            260                 265                 270

Pro Gly Ser Phe Asp Val Leu Glu Asp Ile Ala Thr Ser Val Asn Lys
        275                 280                 285

Gln Val Pro Ile Ile Phe Asp Ser Gly Val Arg Gly Ser Asp Val
    290                 295                 300

Phe Lys Ala Leu Ala Ser Gly Ala Asp Ile Val Ala Leu Gly Arg Pro
```

```
                305                 310                 315                 320
Val Ile Tyr Gly Leu Ala Leu Gly Gly Ala Lys Gly Val Gln Ser Val
                    325                 330                 335

Phe Glu His Ile Asp His Glu Leu Glu Ile Val Met Gln Leu Ala Gly
            340                 345                 350

Thr Lys Thr Ile Asp Asp Ile Lys Asn Asn Pro Leu Leu Asn Ile Lys
        355                 360                 365

Tyr

<210> SEQ ID NO 29
<211> LENGTH: 972
<212> TYPE: DNA
<213> ORGANISM: Lactobacillus acidophilus

<400> SEQUENCE: 29
atggcaagag ttgaaaaacc tcgtaaagtt attttagttg gtgacggtgc tgtaggttct      60
acctttgcat tttcaatggt gcaacaaggt attgctgaag aattaggtat cattgatatt     120
gctaaggaac acgttgaagg tgacgcaatc gacttagcag atgctactcc atggactttc     180
ccaaagaaca tttacgcagc tgactacgct gactgcaagg acgcagactt agtagttatt     240
actgctggtg ctccacaaaa gccaggtgaa actcgtcttg accttgttaa caagaacttg     300
aagattttat catcaatcgt tgaaccagtt gttgaatcag ctttgaagg tatcttctta     360 gtagttgcta acccagttga catcttgact cacgcaactt ggaagatttc aggcttccct     420
aaggatcgcg ttattggttc aggtacttca cttgatactg tcgtcttca aaaggttatc     480 ggtaagatgg aacacgttga cccacgttca gttaatgcat acatgcttgg tgaacacggt     540
gatactgaat tcccagtatg gagctacaac aatgttggtg cgtaaaggt tagcgactgg     600 gttaaggctc acggtatgga tgaatctaag cttgaagaaa tccacaagga agttgctgac     660
atggcttacg acattatcaa caagaagggt gctactttct acggtatcgg tacagcttca     720
gcaatgatcg ctaaggctat cttgaacgat gaacaccgtg tacttccact ctcagttgca     780
atggatggtc aatacggttt acacgacctt cacattggta ctcctgcagt tgttggccgt     840
aacggtcttg aacaaattat tgaaatgcct ttaaccgctg atgaacaagc taagatggaa     900
gcttctgcta agcaattaaa ggaagttatg gacaaagcct ttgaagaaac tggcgttaag     960
gttcgtcaat aa                                                         972

<210> SEQ ID NO 30
<211> LENGTH: 323
<212> TYPE: PRT
<213> ORGANISM: Lactobacillus acidophilus

<400> SEQUENCE: 30

Met Ala Arg Val Glu Lys Pro Arg Lys Val Ile Leu Val Gly Asp Gly
1               5                   10                  15

Ala Val Gly Ser Thr Phe Ala Phe Ser Met Val Gln Gln Gly Ile Ala
            20                  25                  30

Glu Glu Leu Gly Ile Ile Asp Ile Ala Lys Glu His Val Glu Gly Asp
        35                  40                  45

Ala Ile Asp Leu Ala Asp Ala Thr Pro Trp Thr Phe Pro Lys Asn Ile
    50                  55                  60

Tyr Ala Ala Asp Tyr Ala Asp Cys Lys Asp Ala Asp Leu Val Val Ile
65                  70                  75                  80

Thr Ala Gly Ala Pro Gln Lys Pro Gly Glu Thr Arg Leu Asp Leu Val
```

```
                85                  90                  95
Asn Lys Asn Leu Lys Ile Leu Ser Ser Ile Val Glu Pro Val Val Glu
            100                 105                 110

Ser Gly Phe Glu Gly Ile Phe Leu Val Val Ala Asn Pro Val Asp Ile
        115                 120                 125

Leu Thr His Ala Thr Trp Lys Ile Ser Gly Phe Pro Lys Asp Arg Val
    130                 135                 140

Ile Gly Ser Gly Thr Ser Leu Asp Thr Gly Arg Leu Gln Lys Val Ile
145                 150                 155                 160

Gly Lys Met Glu His Val Asp Pro Arg Ser Val Asn Ala Tyr Met Leu
                165                 170                 175

Gly Glu His Gly Asp Thr Glu Phe Pro Val Trp Ser Tyr Asn Asn Val
            180                 185                 190

Gly Gly Val Lys Val Ser Asp Trp Val Lys Ala His Gly Met Asp Glu
        195                 200                 205

Ser Lys Leu Glu Glu Ile His Lys Glu Val Ala Asp Met Ala Tyr Asp
    210                 215                 220

Ile Ile Asn Lys Lys Gly Ala Thr Phe Tyr Gly Ile Gly Thr Ala Ser
225                 230                 235                 240

Ala Met Ile Ala Lys Ala Ile Leu Asn Asp Glu His Arg Val Leu Pro
                245                 250                 255

Leu Ser Val Ala Met Asp Gly Gln Tyr Gly Leu His Asp Leu His Ile
            260                 265                 270

Gly Thr Pro Ala Val Val Gly Arg Asn Gly Leu Glu Gln Ile Ile Glu
        275                 280                 285

Met Pro Leu Thr Ala Asp Glu Gln Ala Lys Met Glu Ala Ser Ala Lys
    290                 295                 300

Gln Leu Lys Glu Val Met Asp Lys Ala Phe Glu Glu Thr Gly Val Lys
305                 310                 315                 320

Val Arg Gln

<210> SEQ ID NO 31
<211> LENGTH: 927
<212> TYPE: DNA
<213> ORGANISM: Lactobacillus acidophilus

<400> SEQUENCE: 31
atgagtagaa aagtgttcct tgtaggtgat ggtgctgttg gttcaacttt tgcaaatgac    60
ttattgcaaa atacaactgt tgatgaatta gcgattttttg atgttgctaa agatcgtcca   120
gttggtgatt caatggattt ggaagatatt actccattta caggtcaaac taatattcat   180
ccagcagaat atagtgatgc taaagatgca gatgtgtgtg taattactgc tggtgttcct   240
cgtaaacctg gtgaaactag acttgactta gttaataaga atgtaaagat tttaaagact   300
attgttgatc cggttgttga atccggtttt aagggtgtat tgttgtttc agctaacccg   360 gttgatattt taccacatt gactcaaaaa atatccggtt ttccaaaaga tcgtgtaatt   420
ggtactggta cttcacttga ttcaatgcgt cttcgcgttg aattggcaaa gaaacttaat   480
gttccagtag ctaaggttaa ctcaatggtt cttggtgaac acggtgatac tagttttgaa   540
aactttgacg aatcaactgt tgacaataag ccacttcgcg attactcaga atcaatgat    600 aatgttttaa gtgaaattga gtcagacgtc cgtaaaaagg gtggaaagat catcactaac   660
aaaggagcta cattctatgg tgttgctatg atgcttactc aaattgttag tgctatttta   720
gataatcgtt caatttgttt gccattatca gccccaatta atggtgaata tggcattaag   780
```

```
catgatcttt acttaggtac tccaactata attaacggta atggtattga aaaagttatt    840
gaaactaaac tttcagatgt agaaaaagct aagatgatca attctgcaga taagatgcaa    900
gaagttttat caggtgttga aatgtaa                                       927
```

<210> SEQ ID NO 32
<211> LENGTH: 308
<212> TYPE: PRT
<213> ORGANISM: Lactobacillus acidophilus

<400> SEQUENCE: 32

```
Met Ser Arg Lys Val Phe Leu Val Gly Asp Gly Ala Val Gly Ser Thr
1               5                   10                  15

Phe Ala Asn Asp Leu Leu Gln Asn Thr Thr Val Asp Glu Leu Ala Ile
                20                  25                  30

Phe Asp Val Ala Lys Asp Arg Pro Val Gly Asp Ser Met Asp Leu Glu
            35                  40                  45

Asp Ile Thr Pro Phe Thr Gly Gln Thr Asn Ile His Pro Ala Glu Tyr
        50                  55                  60

Ser Asp Ala Lys Asp Ala Asp Val Cys Val Ile Thr Ala Gly Val Pro
65                  70                  75                  80

Arg Lys Pro Gly Glu Thr Arg Leu Asp Leu Val Asn Lys Asn Val Lys
                85                  90                  95

Ile Leu Lys Thr Ile Val Asp Pro Val Val Glu Ser Gly Phe Lys Gly
                100                 105                 110

Val Phe Val Val Ser Ala Asn Pro Val Asp Ile Leu Thr Thr Leu Thr
            115                 120                 125

Gln Lys Ile Ser Gly Phe Pro Lys Asp Arg Val Ile Gly Thr Gly Thr
        130                 135                 140

Ser Leu Asp Ser Met Arg Leu Arg Val Glu Leu Ala Lys Lys Leu Asn
145                 150                 155                 160

Val Pro Val Ala Lys Val Asn Ser Met Val Leu Gly Glu His Gly Asp
                165                 170                 175

Thr Ser Phe Glu Asn Phe Asp Glu Ser Thr Val Asp Asn Lys Pro Leu
            180                 185                 190

Arg Asp Tyr Ser Glu Ile Asn Asp Asn Val Leu Ser Glu Ile Glu Ser
        195                 200                 205

Asp Val Arg Lys Lys Gly Gly Lys Ile Ile Thr Asn Lys Gly Ala Thr
    210                 215                 220

Phe Tyr Gly Val Ala Met Met Leu Thr Gln Ile Val Ser Ala Ile Leu
225                 230                 235                 240

Asp Asn Arg Ser Ile Cys Leu Pro Leu Ser Ala Pro Ile Asn Gly Glu
                245                 250                 255

Tyr Gly Ile Lys His Asp Leu Tyr Leu Gly Thr Pro Thr Ile Ile Asn
            260                 265                 270

Gly Asn Gly Ile Glu Lys Val Ile Glu Thr Lys Leu Ser Asp Val Glu
        275                 280                 285

Lys Ala Lys Met Ile Asn Ser Ala Asp Lys Met Gln Glu Val Leu Ser
    290                 295                 300

Gly Val Glu Met
305
```

<210> SEQ ID NO 33
<211> LENGTH: 1050
<212> TYPE: DNA

<213> ORGANISM: Lactobacillus acidophilus

<400> SEQUENCE: 33

```
atggtcatac taataaattt tacggaggtt aaatttatga caaagatttt tgcttacgct      60
attcgtaaag acgaagaacc attcttaaac gaatggaagg aagctcacaa agatatcgat     120
gttgattaca ctgataaact tttgactcct gaaactgcaa agcttgctga aggtgcagac     180
ggtgttgttg ttaccaaca attagactac actcctgaaa cccttcaagc attggcagat     240
gctggcgtaa ctaagatgtc attacgtaac gttggtgtcg ataacatcga catggacaag     300
gccaaagaat taggctttga atcactaat gttcctgttt actcaccaga cgctattgct     360
gaacatgctg ctattcaagc tgcacgtgta ttacgtcaag caagcgcat ggacgaaaag     420
atggctaaac gtgatttacg ttgggcacca actatcggcc gtgaagttcg tgaccaagtt     480
gtcggtgttg ttggtactgg tcacattggt caagtattta tgaagattat ggaaggcttt     540
ggcgcaaaag ttattgctta cgatatcttc aagaaccctg aacttgaaaa gaagggttac     600
tacgttgatt cacttgatga cttgtacaag caagctgatg taatttcact tcacgtacca     660
gacgttccag ctaacgtaca catgattaac gatgaatcaa tcgccaaaat gaaggatggc     720
gttgtaatcg taaactgctc acgtggtcca cttgttgaca ctgatgcagt aattcgtggt     780
ttagactcag gcaagatctt cggcttcgtt atggatactt acgaaggcga agttggtgta     840
tttaacaagg actgggaagg taagaattc ccagacgaac gcttggcaga cttaattgat     900
cgtccaaacg tattggtaac cccacacact gccttctaca ctactcacgc tgtacgtaac     960
atggttgtta aggcatttga caacaacttg gaattaatca gggcgaaaa accagattct    1020
ccagttgctt tggacaagaa caagttctaa                                     1050
```

<210> SEQ ID NO 34
<211> LENGTH: 349
<212> TYPE: PRT
<213> ORGANISM: Lactobacillus acidophilus

<400> SEQUENCE: 34

```
Met Val Ile Leu Ile Asn Phe Thr Glu Val Lys Phe Met Thr Lys Ile
1               5                   10                  15

Phe Ala Tyr Ala Ile Arg Lys Asp Glu Glu Pro Phe Leu Asn Glu Trp
            20                  25                  30

Lys Glu Ala His Lys Asp Ile Asp Val Asp Tyr Thr Asp Lys Leu Leu
        35                  40                  45

Thr Pro Glu Thr Ala Lys Leu Ala Glu Gly Ala Asp Gly Val Val Val
    50                  55                  60

Tyr Gln Gln Leu Asp Tyr Thr Pro Glu Thr Leu Gln Ala Leu Ala Asp
65                  70                  75                  80

Ala Gly Val Thr Lys Met Ser Leu Arg Asn Val Gly Val Asp Asn Ile
                85                  90                  95

Asp Met Asp Lys Ala Lys Glu Leu Gly Phe Glu Ile Thr Asn Val Pro
            100                 105                 110

Val Tyr Ser Pro Asp Ala Ile Ala Glu His Ala Ala Ile Gln Ala Ala
        115                 120                 125

Arg Val Leu Arg Gln Asp Lys Arg Met Asp Glu Lys Met Ala Lys Arg
    130                 135                 140

Asp Leu Arg Trp Ala Pro Thr Ile Gly Arg Glu Val Arg Asp Gln Val
145                 150                 155                 160

Val Gly Val Val Gly Thr Gly His Ile Gly Gln Val Phe Met Lys Ile
```

```
                          165                 170                 175
Met Glu Gly Phe Gly Ala Lys Val Ile Ala Tyr Asp Ile Phe Lys Asn
                180                 185                 190

Pro Glu Leu Glu Lys Lys Gly Tyr Tyr Val Asp Ser Leu Asp Asp Leu
            195                 200                 205

Tyr Lys Gln Ala Asp Val Ile Ser Leu His Val Pro Asp Val Pro Ala
        210                 215                 220

Asn Val His Met Ile Asn Asp Glu Ser Ile Ala Lys Met Lys Asp Gly
225                 230                 235                 240

Val Val Ile Val Asn Cys Ser Arg Gly Pro Leu Val Asp Thr Asp Ala
                245                 250                 255

Val Ile Arg Gly Leu Asp Ser Gly Lys Ile Phe Gly Phe Val Met Asp
                260                 265                 270

Thr Tyr Glu Gly Glu Val Gly Val Phe Asn Lys Asp Trp Glu Gly Lys
            275                 280                 285

Glu Phe Pro Asp Glu Arg Leu Ala Asp Leu Ile Asp Arg Pro Asn Val
        290                 295                 300

Leu Val Thr Pro His Thr Ala Phe Tyr Thr Thr His Ala Val Arg Asn
305                 310                 315                 320

Met Val Val Lys Ala Phe Asp Asn Asn Leu Glu Leu Ile Lys Gly Glu
                325                 330                 335

Lys Pro Asp Ser Pro Val Ala Leu Asp Lys Asn Lys Phe
            340                 345

<210> SEQ ID NO 35
<211> LENGTH: 5323
<212> TYPE: DNA
<213> ORGANISM: artificial sequence
<220> FEATURE:
<223> OTHER INFORMATION: vector

<400> SEQUENCE: 35
gaattcagat ctctcgagcc cgggatcgat ggtacctcgc gaaagcttgg atgttgtaca      60
ggataatgtc cagaaggtcg atagaaagcg tgagaaacag cgtacagacg atttagagat     120
gtagaggtac ttttatgccg agaaaacttt ttgcgtgtga cagtccttaa aatatactta     180
gagcgtaagc gaaagtagta gcgacagcta ttaactttcg gttgcaaagc tctaggatt      240 ttaatggacg cagcgcatca cacgcaaaaa ggaaattgga ataaatgcga aatttgagat     300
gttaattaaa dacctttttg aggtctttt ttcttagatt tttgggggtta tttaggggag     360 aaaacatagg ggggtactac gacctccccc ctaggtgtcc attgtccatt gtccaaacaa     420
ataaataaat attgggtttt taatgttaaa aggttgtttt ttatgttaaa gtgaaaaaaa     480
cagatgttgg gaggtacagt gatagttgta gatagaaaag aagagaaaaa agttgctgtt     540 acttttaagac ttacaacaga gaaaatgag atattaaata gaatcaaaga aaaatataat     600
attagcaaat cagatgcaac cggtattcta ataaaaaaat atgcaaagga ggaatacggt     660
gcattttaaa caaaaaaaga tagacagcac tggcatgctg cctatctatg actaaatttt    720
gttaagtgta ttagcaccgt tattatatca tgagcgaaaa tgtaataaaa gaaactgaaa    780
acaagaaaaa ttcaagagga cgtaattgga catttgtttt atatccagaa tcagcaaaag    840
ccgagtggtt agagtatttaa aaagagttac acattcaatt tgtagtgtct ccattacatg    900
atagggatac tgatacagaa ggtaggatga aaaagagca ttatcatatt ctagtgatgt    960
atgagggtaa taaatcttat gaacagataa aaataattaa cagaagaatt gaatgcgact   1020
```

```
attccgcaga ttgcaggaag tgtgaaaggt cttgtgagat atatgcttca catggacgat    1080
cctaataaat ttaaatatca aaagaagat atgatagttt atggcggtgt agatgttgat     1140
gaattattaa agaaaacaac aacagataga tataaattaa ttaaagaaat gattgagttt    1200
attgatgaac aaggaatcgt agaatttaag agtttaatgg attatgcaat gaagtttaaa    1260
tttgatgatt ggttcccgct tttatgtgat aactcggcgt atgttattca agaatatata    1320
aaatcaaatc ggtataaatc tgaccgatag attttgaatt taggtgtcac aagacactct    1380
tttttcgcac cagcgaaaac tggtttaagc cgactgcgca aaagacataa tcgattcaca    1440
aaaaataggc acacgaaaaa caagttaagg gatgcagttt atgcatccct taacttactt    1500
attaaataat ttatagctat tgaaaagaga taagaattgt tcaaagctaa tattgtttaa    1560
atcgtcaatt cctgcatgtt ttaaggaatt gttaaattga ttttttgtaa atattttctt    1620
gtattctttg ttaacccatt tcataacgaa ataattatac ttttgtttat ctttgtgtga    1680
tattcttgat tttttctac ttaatctgat aagtgagcta ttcactttag gtttaggatg      1740
aaaatattct cttggaacca tacttaatat agaaatatca acttctgcca ttaaaagtaa    1800
tgccaatgag cgttttgtat ttaataatct tttagcaaac ccgtattcca cgattaaata    1860
aatctcatta gctatactat caaaaacaat tttgcgtatt atatccgtac ttatgttata    1920
aggtatatta ccatatattt tataggattg ttttttagga aatttaaact gcaatatatc    1980 cttgttaaa acttggaaat tatcgtgatc aacaagttta ttttctgtag ttttgcataa    2040
tttatggtct atttcaatgg cagttacgaa attacacctc tttactaatt caagggtaaa    2100
atggcctttt cctgagccga tttcaaagat attatcatgt tcatttaatc ttatatttgt    2160 cattattta tctatattat gttttgaagt aataaagttt tgactgtgtt ttatatttt       2220 ctcgttcatt ataaccctct ttaatttggt tatatgaatt ttgcttatta acgattcatt    2280
ataaccactt attttttgtt tggttgataa tgaactgtgc tgattacaaa aatactaaaa    2340
atgcccatat ttttcctcc ttataaaatt agtataatta tagcacgagc tctgataaat      2400
atgaacatga tgagtgatcg ttaaatttat actgcaatcg gatgcgatta ttgaataaaa    2460
gatatgagag atttatctaa tttcttttt cttgtaaaaa aagaaagttc ttaaaggttt      2520
tatagttttg gtcgtagagc acacggttta acgacttaat tacgaagtaa ataagtctag    2580
tgtgttagac tttatgaaat ctatatacgt ttatatatat ttattatccg gatctgcatc    2640
gcaggatgct gctggctacc ctgtggaaca cctacatctg tattaacgaa gcgctggcat    2700
tgaccctgag tgattttct ctggtcccgc cgcatccata ccgccagttg tttacccctca     2760 caacgttcca gtaaccgggc atgttcatca tcagtaaccc gtatcgtgag catcctctct    2820
cgtttcatcg gtatcattac ccccatgaac agaaattccc ccttacacgg aggcatcaag    2880
tgaccaaaca ggaaaaaacc gcccttaaca tggcccgctt tatcagaagc cagacattaa    2940
cgcttctgga gaaactcaac gagctggacg cggatgaaca ggcagacatc tgtgaatcgc    3000
ttcacgacca cgctgatgag ctttaccgca gctgcctcgc gcgtttcggt gatgacggtg    3060
aaaacctctg acacatgcag ctcccggaga cggtcacagc ttgtctgtaa gcggatgccg    3120
ggagcagaca agcccgtcag ggcgcgtcag cgggtgttgg cgggtgtcgg ggcgcagcca    3180
tgacccagtc acgtagcgat agcggagtgt atactggctt aactatgcgg catcagagca    3240
gattgtactg agagtgcacc atatgcggtg tgaaataccg cacagatgcg taaggagaaa    3300
ataccgcatc aggcgctctt ccgcttcctc gctcactgac tcgctgcgct cggtcgttcg    3360
gctgcggcga gcggtatcag ctcactcaaa ggcggtaata cggttatcca cagaatcagg    3420
```

```
ggataacgca ggaaagaaca tgtgagcaaa aggccagcaa aaggccagga accgtaaaaa    3480
ggccgcgttg ctggcgtttt tccataggct ccgcccccct gacgagcatc acaaaaatcg    3540
acgctcaagt cagaggtggc gaaacccgac aggactataa agataccagg cgtttccccc    3600
tggaagctcc ctcgtgcgct ctcctgttcc gaccctgccg cttaccggat acctgtccgc    3660
ctttctccct tcgggaagcg tggcgctttc tcaatgctca cgctgtaggt atctcagttc    3720
ggtgtaggtc gttcgctcca agctgggctg tgtgcacgaa ccccccgttc agcccgaccg    3780
ctgcgcctta tccggtaact atcgtcttga gtccaacccg gtaagacacg acttatcgcc    3840
actggcagca gccactggta acaggattag cagagcgagg tatgtaggcg gtgctacaga    3900
gttcttgaag tggtggccta actacggcta cactagaagg acagtatttg gtatctgcgc    3960
tctgctgaag ccagttacct tcggaaaaag agttggtagc tcttgatccg gcaaacaaac    4020
caccgctggt agcggtggtt tttttgtttg caagcagcag attacgcgca gaaaaaagg    4080 atctcaagaa gatcctttga tcttttctac ggggtctgac gctcagtgga acgaaaactc    4140
acgttaaggg attttggtca tgagattatc aaaaaggatc ttcacctaga tccttttaaa    4200
ttaaaaatga agttttaaat caatctaaag tatatatgag taaacttggt ctgacagtta    4260
ccaatgctta atcagtgagg cacctatctc agcgatctgt ctatttcgtt catccatagt    4320
tgcctgactc cccgtcgtgt agataactac gatacgggag ggcttaccat ctggccccag    4380
tgctgcaatg ataccgcgag acccacgctc accggctcca gatttatcag caataaacca    4440
gccagccgga agggccgagc gcagaagtgg tcctgcaact ttatccgcct ccatccagtc    4500
tattaattgt tgccgggaag ctagagtaag tagttcgcca gttaatagtt tgcgcaacgt    4560
tgttgccatt gctgcaggca tcgtggtgtc acgctcgtcg tttggtatgg cttcattcag    4620
ctccggttcc caacgatcaa ggcgagttac atgatccccc atgttgtgca aaaaagcggt    4680
tagctccttc ggtcctccga tcgttgtcag aagtaagttg gccgcagtgt tatcactcat    4740
ggttatggca gcactgcata attctcttac tgtcatgcca tccgtaagat gcttttctgt    4800
gactggtgag tactcaacca agtcattctg agaatagtgt atgcggcgac cgagttgctc    4860
ttgcccggcg tcaacacggg ataataccgc gccacatagc agaactttaa aagtgctcat    4920
cattggaaaa cgttcttcgg ggcgaaaact ctcaaggatc ttaccgctgt tgagatccag    4980
ttcgatgtaa cccactcgtg cacccaactg atcttcagca tcttttactt tcaccagcgt    5040
ttctgggtga gcaaaaacag gaaggcaaaa tgccgcaaaa aagggaataa gggcgacacg    5100
gaaatgttga atactcatac tcttcctttt tcaatattat tgaagcattt atcagggtta    5160
ttgtctcatg agcggataca tatttgaatg tatttagaaa aataaacaaa tagggggttcc    5220 gcgcacattt ccccgaaaag tgccacctga cgtctaagaa accattatta tcatgacatt    5280
aacctataaa aataggcgta tcacgaggcc ctttcgtctt caa                      5323

<210> SEQ ID NO 36
<211> LENGTH: 5581
<212> TYPE: DNA
<213> ORGANISM: artificial sequence
<220> FEATURE:
<223> OTHER INFORMATION: vector

<400> SEQUENCE: 36
gaattcacta gtcttaagta agtcgtattg gcaccactac tcacaccgtg accgacgcgc      60
ccgccagtca agtgttcaaa agttagcgtt tattaagtgc gataagtata ccacaaaggg     120
```

```
cttattgacg cccgccaaag ggttttgcgg acattgttaa taattgtatt aaaagcatgc      180
tcaatctaac acttattttg cacaaacatg gtatactttta accgtaaaaa ctaaattttc     240
actacgagag gatgacttat tttgtcaagc ctcgagcccg ggatcgatgg tacctcgcga     300
aagcttggat gttgtacagg ataatgtcca gaaggtcgat agaaagcgtg agaaacagcg      360
tacagacgat ttagagatgt agaggtactt ttatgccgag aaaactttttt gcgtgtgaca    420 gtccttaaaa tatacttaga gcgtaagcga aagtagtagc gacagctatt aactttcggt      480
tgcaaagctc taggattttt aatggacgca gcgcatcaca cgcaaaaagg aaattggaat     540
aaatgcgaaa tttgagatgt taattaaaga ccttttttgag gtctttttttt cttagatttt    600 tggggttatt taggggagaa acatagggg ggtactacga cctccccct aggtgtccat      660 tgtccattgt ccaaacaaat aaataaatat tgggttttta atgttaaaag gttgtttttt     720
atgttaaagt gaaaaaaaca gatgttggga ggtacagtga tagttgtaga tagaaaagaa     780
gagaaaaaag ttgctgttac tttaagactt acaacagaag aaaatgagat attaaataga     840
atcaaagaaa aatataatat tagcaaatca gatgcaaccg gtattctaat aaaaaaatat     900
gcaaaggagg aatacggtgc atttttaaaca aaaaaagata gacagcactg gcatgctgcc     960
tatctatgac taaattttgt taagtgtatt agcaccgtta ttatatcatg agcgaaaatg    1020
taataaaaga aactgaaaac aagaaaaatt caagaggacg taattggaca tttgttttat    1080
atccagaatc agcaaaagcc gagtggttag agtatttaaa agagttacac attcaatttg    1140
tagtgtctcc attacatgat agggatactg atacagaagg taggatgaaa aaagagcatt    1200
atcatattct agtgatgtat gagggtaata aatcttatga acagataaaa ataattaaca    1260
gaagaattga atgcgactat tccgcagatt gcaggaagtg tgaaaggtct tgtgagatat    1320
atgcttcaca tggacgatcc taataaattt aaatatcaaa agaagatat gatagtttat    1380 ggcggtgtag atgttgatga attattaaag aaaacaacaa cagatagata taaattaatt    1440
aaagaaatga ttgagtttat tgatgaacaa ggaatcgtag aatttaagag tttaatggat    1500
tatgcaatga agtttaaatt tgatgattgg ttcccgcttt tatgtgataa ctcggcgtat    1560
gttattcaag aatatataaa atcaaatcgg tataaatctg accgatagat tttgaattta    1620
ggtgtcacaa gacactcttt tttcgcacca gcgaaaactg gtttaagccg actgcgcaaa    1680
agacataatc gattcacaaa aaataggcac acgaaaaaca agttaaggga tgcagtttat    1740
gcatccctta acttacttat taaataattt atagctattg aaaagagata agaattgttc    1800
aaagctaata ttgtttaaat cgtcaattcc tgcatgtttt aaggaattgt taaattgatt    1860
ttttgtaaat atttttcttgt attctttgtt aacccatttc ataacgaaat aattatactt    1920
ttgtttatct ttgtgtgata ttcttgattt ttttctactt aatctgataa gtgagctatt    1980
cactttaggt ttaggatgaa aatattctct tggaaccata cttaatatag aaatatcaac    2040
ttctgccatt aaaagtaatg ccaatgagcg ttttgtatt aataatcttt tagcaaaccc    2100
gtattccacg attaaataaa tctcattagc tatactatca aaaacaattt tgcgtattat    2160
atccgtactt atgttataag gtatattacc atatatttta taggattggt ttttaggaaa    2220
tttaaactgc aatatatcct tgtttaaaac ttggaaatta tcgtgatcaa caagtttatt    2280
ttctgtagtt ttgcataatt tatggtctat ttcaatggca gttacgaaat tacacctctt    2340
tactaattca agggtaaaat ggccttttcc tgagccgatt tcaaagatat tatcatgttc    2400
atttaatctt atatttgtca ttattttatc tatattatgt tttgaagtaa taagttttg     2460 actgtgttttt atattttttct cgttcattat aaccctcttt aatttggtta tatgaatttt    2520
```

```
gcttattaac gattcattat aaccacttat tttttgtttg gttgataatg aactgtgctg   2580
attacaaaaa tactaaaaat gcccatattt tttcctcctt ataaaattag tataattata   2640
gcacgagctc tgataaatat gaacatgatg agtgatcgtt aaatttatac tgcaatcgga   2700
tgcgattatt gaataaaaga tatgagagat ttatctaatt tctttttct tgtaaaaaaa    2760
gaaagttctt aaaggtttta tagttttggt cgtagagcac acggtttaac gacttaatta   2820
cgaagtaaat aagtctagtg tgttagactt tatgaaatct atatacgttt atatatattt   2880
attatccgga tctgcatcgc aggatgctgc tggctaccct gtggaacacc tacatctgta   2940
ttaacgaagc gctggcattg accctgagtg attttctct ggtcccgccg catccatacc    3000
gccagttgtt taccctcaca acgttccagt aaccgggcat gttcatcatc agtaacccgt   3060
atcgtgagca tcctctctcg tttcatcggt atcattaccc ccatgaacag aaattccccc   3120
ttacacggag gcatcaagtg accaaacagg aaaaaaccgc ccttaacatg gcccgcttta   3180
tcagaagcca gacattaacg cttctggaga aactcaacga gctggacgcg gatgaacagg   3240
cagacatctg tgaatcgctt cacgaccacg ctgatgagct ttaccgcagc tgcctcgcgc   3300
gtttcggtga tgacggtgaa aacctctgac acatgcagct cccggagacg gtcacagctt   3360
gtctgtaagc ggatgccggg agcagacaag cccgtcaggg cgcgtcagcg ggtgttggcg   3420
ggtgtcgggg cgcagccatg acccagtcac gtagcgatag cggagtgtat actggcttaa   3480
ctatgcggca tcagagcaga ttgtactgag agtgcaccat atgcggtgtg aaataccgca   3540
cagatgcgta aggagaaaat accgcatcag gcgctcttcc gcttcctcgc tcactgactc   3600
gctgcgctcg gtcgttcggc tgcggcgagc ggtatcagct cactcaaagg cggtaatacg   3660
gttatccaca gaatcagggg ataacgcagg aagaacatg tgagcaaaag gccagcaaaa    3720
ggccaggaac cgtaaaaagg ccgcgttgct ggcgttttc cataggctcc gcccccctga    3780
cgagcatcac aaaatcgac gctcaagtca gaggtggcga acccgacag gactataaag     3840
ataccaggcg tttccccctg gaagctccct cgtgcgctct cctgttccga ccctgccgct   3900
taccggatac ctgtccgcct ttctcccttc gggaagcgtg gcgctttctc aatgctcacg   3960
ctgtaggtat ctcagttcgg tgtaggtcgt tcgctccaag ctgggctgtg tgcacgaacc   4020
ccccgttcag cccgaccgct gcgccttatc cggtaactat cgtcttgagt ccaacccggt   4080
aagacacgac ttatcgccac tggcagcagc cactggtaac aggattagca gagcgaggta   4140
tgtaggcggt gctacagagt tcttgaagtg gtggcctaac tacggctaca ctagaaggac   4200
agtatttggt atctgcgctc tgctgaagcc agttaccttc ggaaaaagag ttggtagctc   4260
ttgatccggc aaacaaacca ccgctggtag cggtggtttt tttgtttgca agcagcagat   4320
tacgcgcaga aaaaaggat ctcaagaaga tcctttgatc ttttctacgg ggtctgacgc    4380
tcagtggaac gaaaactcac gttaagggat tttggtcatg agattatcaa aaaggatctt   4440
cacctagatc cttttaaatt aaaaatgaag ttttaaatca atctaaagta tatatgagta   4500
aacttggtct gacagttacc aatgcttaat cagtgaggca cctatctcag cgatctgtct   4560
atttcgttca tccatagttg cctgactccc cgtcgtgtag ataactacga tacgggaggg   4620
cttaccatct ggccccagtg ctgcaatgat accgcgagac ccacgctcac cggctccaga   4680
tttatcagca ataaaccagc cagccggaag ggccgagcgc agaagtggtc ctgcaacttt   4740
atccgcctcc atccagtcta ttaattgttg ccgggaagct agagtaagta gttcgccagt   4800
taatagtttg cgcaacgttg ttgccattgc tgcaggcatc gtggtgtcac gctcgtcgtt   4860
```

```
tggtatggct tcattcagct ccggttccca acgatcaagg cgagttacat gatcccccat    4920
gttgtgcaaa aaagcggtta gctccttcgg tcctccgatc gttgtcagaa gtaagttggc    4980
cgcagtgtta tcactcatgg ttatggcagc actgcataat tctcttactg tcatgccatc    5040
cgtaagatgc ttttctgtga ctggtgagta ctcaaccaag tcattctgag aatagtgtat    5100
gcggcgaccg agttgctctt gcccggcgtc aacacgggat aataccgcgc cacatagcag    5160
aactttaaaa gtgctcatca ttggaaaacg ttcttcgggg cgaaaactct caaggatctt    5220
accgctgttg agatccagtt cgatgtaacc cactcgtgca cccaactgat cttcagcatc    5280
ttttactttc accagcgttt ctgggtgagc aaaaacagga aggcaaaatg ccgcaaaaaa    5340
gggaataagg gcgacacgga aatgttgaat actcatactc ttcctttttc aatattattg    5400
aagcatttat cagggttatt gtctcatgag cggatacata tttgaatgta tttagaaaaa    5460
taaacaaata ggggttccgc gcacatttcc ccgaaaagtg ccacctgacg tctaagaaac    5520
cattattatc atgacattaa cctataaaaa taggcgtatc acgaggccct ttcgtcttca    5580
a                                                                    5581

<210> SEQ ID NO 37
<211> LENGTH: 7443
<212> TYPE: DNA
<213> ORGANISM: artificial sequence
<220> FEATURE:
<223> OTHER INFORMATION: vector

<400> SEQUENCE: 37
gaattcacta gtcttaagta agtcgtattg gcaccactac tcacaccgtg accgacgcgc      60
ccgccagtca agtgttcaaa agttagcgtt tattaagtgc gataagtata ccacaaaggg     120
cttattgacg cccgccaaag ggttttgcgg acattgttaa taattgtatt aaaagcatgc     180
tcaatctaac acttattttg cacaaacatg gtatacttta accgtaaaaa ctaaattttc     240
actacgagag gatgacttat tttgtcaagc ctcgaggcta gcatatatag gaggaatttt     300
tgtaatgaaa aaagtcgcac ttgttaccgg cgccggccag gggattggta agctatcgc      360
ccttcgtctg gtgaaggatg gatttgccgt ggccattgcc gattataacg acgccaccgc     420
caaagcggtc gcctccgaaa tcaaccaggc cggcggccgc gccatggcgg tgaaagtgga     480
tgtttctgac cgcgaccagg tatttgccgc cgtcgaacag gcgcgcaaaa cgctgggcgg     540
cttcgacgtc atcgtcaaca acgccggcgt ggcgccatcc acgccgatcg agtccattac     600
cccggagatt gtcgacaaag tctacaacat caacgtcaaa ggggtgatct ggggcatcca     660
ggcggcggtc gaggccttta agaaagaggg tcacggcggg aaaatcatca cgcctgttc      720
ccaggccggc cacgtcggca acccggagct ggcggtatat agctcgagta aattcgccgt     780
acgcggctta acccagaccg ccgctcgcga cctcgcgccg ctgggcatca cggtcaacgg     840
ctactgcccg gggattgtca aaacgccaat gtgggccgaa attgaccgcc aggtgtccga     900
agccgccggt aaaccgctgg gctacggtac cgccgagttc gccaaacgca tcaccctcgg     960
ccgcctgtcc gagccggaag atgtcgccgc ctgcgtctcc tatcttgcca gcccggattc    1020
tgattatatg accggtcagt cattgctgat cgacggcggg atggtgttta actaagatat    1080
catatatagg aggaattttt gtaatgaaag ctctggttta tcacggtgac cacaagatct    1140
cgcttgaaga caagcccaag cccacccttc aaaagcccac ggatgtagta gtacgggttt    1200
tgaagaccac gatctgcggc acggatctcg gcatctacaa aggcaagaat ccagaggtcg    1260
ccgacgggcg catcctgggc catgaagggg taggcgtcat cgaggaagtg ggcgagagtg    1320
```

```
tcacgcagtt caagaaaggc gacaaggtcc tgatttcctg cgtcacttct tgcggctcgt   1380
gcgactactg caagaagcag ctttactccc attgccgcga cggcgggtgg atcctgggtt   1440
acatgatcga tggcgtgcag gccgaatacg tccgcatccc gcatgccgac aacagcctct   1500
acaagatccc ccagacaatt gacgacgaaa tcgccgtcct gctgagcgac atcctgccca   1560
ccggccacga aatcggcgtc cagtatggga atgtccagcc gggcgatgcg gtggctattg   1620
tcggcgcggg ccccgtcggc atgtccgtac tgttgaccgc ccagttctac tcccctcga   1680 ccatcatcgt gatcgacatg gacgagaatc gcctccagct cgccaaggag ctcggggcaa   1740
cgcacaccat caactccggc acggagaacg ttgtcgaagc cgtgcatagg attgcggcag   1800
agggagtcga tgttgcgatc gaggcggtgg gcataccggc gacttgggac atctgccagg   1860
agatcgtcaa gcccggcgcg cacatcgcca acgtcggcgt gcatggcgtc aaggttgact   1920
tcgagattca gaagctctgg atcaagaacc tgacgatcac cacgggactg gtgaacacga   1980
acacgacgcc catgctgatg aaggtcgcct cgaccgacaa gcttccgttg aagaagatga   2040
ttacccatcg cttcgagctg gccgagatcg agcacgccta tcaggtattc ctcaatggcg   2100
ccaaggagaa ggcgatgaag atcatcctct cgaacgcagg cgctgcctga ggtacctcgc   2160
gaaagcttgg atgttgtaca ggataatgtc cagaaggtcg atagaaagcg tgagaaacag   2220
cgtacagacg atttagagat gtagaggtac ttttatgccg agaaaacttt ttgcgtgtga   2280
cagtccttaa aatatactta gagcgtaagc gaaagtagta gcgacagcta ttaactttcg   2340
gttgcaaagc tctaggattt ttaatggacg cagcgcatca cacgcaaaaa ggaaattgga   2400
ataaatgcga aatttgagat gttaattaaa gaccttttg aggtcttttt ttcttagatt   2460
tttggggtta tttaggggag aaaacatagg ggggtactac gacctccccc ctaggtgtcc   2520
attgtccatt gtccaaacaa ataaataaat attgggtttt taatgttaaa aggttgtttt   2580
ttatgttaaa gtgaaaaaaa cagatgttgg gaggtacagt gatagttgta gatagaaaaag   2640 aagagaaaaa agttgctgtt actttaagac ttacaacaga agaaaatgag atattaaata   2700
gaatcaaaga aaaatataat attagcaaat cagatgcaac cggtattcta ataaaaaaat   2760
atgcaaagga ggaatacggt gcattttaaa caaaaaaaga tagacagcac tggcatgctg   2820
cctatctatg actaaatttt gttaagtgta ttagcaccgt tattatatca tgagcgaaaa   2880
tgtaataaaa gaaactgaaa acaagaaaaa ttcaagagga cgtaattgga catttgtttt   2940
atatccagaa tcagcaaaag ccgagtggtt agagtattta aaagagttac acattcaatt   3000
tgtagtgtct ccattacatg atagggatac tgatacagaa ggtaggatga aaaagagca   3060 ttatcatatt ctagtgatgt atgagggtaa taaatcttat gaacagataa aaataattaa   3120
cagaagaatt gaatgcgact attccgcaga ttgcaggaag tgtgaaaggt cttgtgagat   3180
atatgcttca catggacgat cctaataaat ttaaatatca aaaagaagat atgatagttt   3240
atggcggtgt agatgttgat gaattattaa agaaacaac aacagataga tataaattaa   3300
ttaaagaaat gattgagttt attgatgaac aaggaatcgt agaatttaag agtttaatgg   3360
attatgcaat gaagttttaaa tttgatgatt ggttcccgct tttatgtgat aactcggcgt   3420
atgttattca agaatatata aaatcaaatc ggtataaatc tgaccgatag attttgaatt   3480
taggtgtcac aagacactct ttttttcgcac cagcgaaaac tggtttaagc cgactgcgca   3540
aaagacataa tcgattcaca aaaaataggc acacgaaaaa caagttaagg gatgcagttt   3600
atgcatccct taacttactt attaaataat ttatagctat tgaaaagaga taagaattgt   3660
```

```
tcaaagctaa tattgtttaa atcgtcaatt cctgcatgtt ttaaggaatt gttaaattga    3720
ttttttgtaa atattttctt gtattctttg ttaacccatt tcataacgaa ataattatac    3780
ttttgtttat ctttgtgtga tattcttgat ttttttctac ttaatctgat aagtgagcta    3840
ttcactttag gtttaggatg aaaatattct cttggaacca tacttaatat agaaatatca    3900
acttctgcca ttaaaagtaa tgccaatgag cgttttgtat ttaataatct tttagcaaac    3960
ccgtattcca cgattaaata aatctcatta gctatactat caaaaacaat tttgcgtatt    4020
atatccgtac ttatgttata aggtatatta ccatatattt tataggattg gttttagga     4080 aatttaaact gcaatatatc cttgtttaaa acttggaaat tatcgtgatc aacaagttta    4140
ttttctgtag ttttgcataa tttatggtct atttcaatgg cagttacgaa attacacctc    4200
tttactaatt caagggtaaa atggccttt cctgagccga tttcaaagat attatcatgt     4260
tcatttaatc ttatatttgt cattatttta tctatattat gttttgaagt aataaagttt    4320
tgactgtgtt ttatatttt ctcgttcatt ataaccctct ttaatttggt tatatgaatt     4380
ttgcttatta acgattcatt ataaccactt attttttgtt tggttgataa tgaactgtgc    4440
tgattacaaa aatactaaaa atgcccatat ttttcctcc ttataaaatt agtataatta     4500
tagcacgagc tctgataaat atgaacatga tgagtgatcg ttaaatttat actgcaatcg    4560
gatgcgatta ttgaataaaa gatatgagag atttatctaa tttctttttt cttgtaaaaa    4620
aagaaagttc ttaaaggttt tatagttttg gtcgtagagc acacggttta acgacttaat    4680
tacgaagtaa ataagtctag tgtgttagac tttatgaaat ctatatacgt ttatatatat    4740
ttattatccg gatctgcatc gcaggatgct gctggctacc ctgtggaaca cctacatctg    4800
tattaacgaa gcgctggcat tgaccctgag tgattttct ctggtcccgc cgcatccata     4860
ccgccagttg tttaccctca caacgttcca gtaaccgggc atgttcatca tcagtaaccc    4920
gtatcgtgag catcctctct cgtttcatcg gtatcattac ccccatgaac agaaattccc    4980
ccttacacgg aggcatcaag tgaccaaaca ggaaaaaacc gcccttaaca tggcccgctt    5040
tatcagaagc cagacattaa cgcttctgga gaaactcaac gagctggacg cggatgaaca    5100
ggcagacatc tgtgaatcgc ttcacgacca cgctgatgag ctttaccgca gctgcctcgc    5160
gcgtttcggt gatgacggtg aaaacctctg acacatgcag ctcccggaga cggtcacagc    5220
ttgtctgtaa gcggatgccg ggagcagaca agcccgtcag ggcgcgtcag cgggtgttgg    5280
cgggtgtcgg ggcgcagcca tgacccagtc acgtagcgat agcggagtgt atactggctt    5340
aactatgcgg catcagagca gattgtactg agagtgcacc atatgcggtg tgaaataccg    5400
cacagatgcg taaggagaaa ataccgcatc aggcgctctt ccgcttcctc gctcactgac    5460
tcgctgcgct cggtcgttcg gctgcggcga gcggtatcag ctcactcaaa ggcggtaata    5520
cggttatcca cagaatcagg ggataacgca ggaaagaaca tgtgagcaaa aggccagcaa    5580
aaggccagga accgtaaaaa ggccgcgttg ctggcgtttt tccataggct ccgcccccct    5640
gacgagcatc acaaaaatcg acgctcaagt cagaggtggc gaaacccgac aggactataa    5700
agataccagg cgtttccccc tggaagctcc ctcgtgcgct ctcctgttcc gaccctgccg    5760
cttaccggat acctgtccgc ctttctccct tcgggaagcg tggcgctttc tcaatgctca    5820
cgctgtaggt atctcagttc ggtgtaggtc gttcgctcca agctgggctg tgtgcacgaa    5880
ccccccgttc agcccgaccg ctgcgcctta tccggtaact atcgtcttga gtccaacccg    5940
gtaagacacg acttatcgcc actggcagca gccactggta acaggattag cagagcgagg    6000
tatgtaggcg gtgctacaga gttcttgaag tggtggccta actacggcta cactagaagg    6060
```

```
acagtatttg gtatctgcgc tctgctgaag ccagttacct tcggaaaaag agttggtagc    6120
tcttgatccg gcaaacaaac caccgctggt agcggtggtt tttttgtttg caagcagcag    6180
attacgcgca gaaaaaaagg atctcaagaa gatcctttga tcttttctac ggggtctgac    6240
gctcagtgga acgaaaactc acgttaaggg attttggtca tgagattatc aaaaaggatc    6300
ttcacctaga tccttttaaa ttaaaaatga agttttaaat caatctaaag tatatatgag    6360
taaacttggt ctgacagtta ccaatgctta atcagtgagg cacctatctc agcgatctgt    6420
ctatttcgtt catccatagt tgcctgactc cccgtcgtgt agataactac gatacgggag    6480
ggcttaccat ctggccccag tgctgcaatg ataccgcgag acccacgctc accggctcca    6540
gatttatcag caataaacca gccagccgga agggccgagc gcagaagtgg tcctgcaact    6600
ttatccgcct ccatccagtc tattaattgt tgccgggaag ctagagtaag tagttcgcca    6660
gttaatagtt tgcgcaacgt tgttgccatt gctgcaggca tcgtggtgtc acgctcgtcg    6720
tttggtatgg cttcattcag ctccggttcc caacgatcaa ggcagttac atgatccccc    6780 atgttgtgca aaaaagcggt tagctccttc ggtcctccga tcgttgtcag aagtaagttg    6840
gccgcagtgt tatcactcat ggttatggca gcactgcata attctcttac tgtcatgcca    6900
tccgtaagat gcttttctgt gactggtgag tactcaacca agtcattctg agaatagtgt    6960
atgcggcgac cgagttgctc ttgcccggcg tcaacacggg ataataccgc gccacatagc    7020
agaactttaa aagtgctcat cattggaaaa cgttcttcgg ggcgaaaact ctcaaggatc    7080
ttaccgctgt tgagatccag ttcgatgtaa cccactcgtg cacccaactg atcttcagca    7140
tcttttactt tcaccagcgt ttctgggtga gcaaaaacag gaaggcaaaa tgccgcaaaa    7200
aagggaataa gggcgacacg gaaatgttga atactcatac tcttcctttt tcaatattat    7260
tgaagcattt atcagggtta ttgtctcatg agcggataca tatttgaatg tatttagaaa    7320
aataaacaaa taggggttcc gcgcacattt ccccgaaaag tgccacctga cgtctaagaa    7380
accattatta tcatgacatt aacctataaa aataggcgta tcacgaggcc ctttcgtctt    7440
caa                                                                  7443
```

<210> SEQ ID NO 38
<211> LENGTH: 5311
<212> TYPE: DNA
<213> ORGANISM: artificial sequence
<220> FEATURE:
<223> OTHER INFORMATION: vector

<400> SEQUENCE: 38

```
gaattcacta gtcttaagta agtcgtattg caccactac tcacaccgtg accgacgcgc      60
ccgccagtca agtgttcaaa agttagcgtt tattaagtgc gataagtata ccacaaaggg    120
cttattgacg cccgccaaag ggttttgcgg acattgttaa taattgtatt aaaagcatgc    180
tcaatctaac acttattttg cacaaacatg gtatacttta accgtaaaaa ctaaattttc    240
actacgagag gatgacttat tttgtcaagc ctcgaggcta gcatatatag gaggaatttt    300
tgtaatgaaa aaagtcgcac ttgttaccgg cgcggccag gggattggta aagctatcgc    360
ccttcgtctg gtgaaggatg gatttgccgt ggccattgcc gattataacg acgccaccgc    420
caaagcggtc gcctccgaaa tcaaccaggc cggcggccgc gccatggcgg tgaaagtgga    480
tgtttctgac cgcgaccagg tatttgccgc cgtcgaacag gcgcgcaaaa cgctgggcgg    540
cttcgacgtc atcgtcaaca acgccggcgt ggcgccatcc acgccgatcg agtccattac    600
```

```
cccggagatt gtcgacaaag tctacaacat caacgtcaaa ggggtgatct ggggcatcca    660
ggcggcggtc gaggccttta agaaagaggg tcacggcggg aaaatcatca acgcctgttc    720
ccaggccggc cacgtcggca acccggagct ggcggtatat agctcgagta aattcgccgt    780
acgcggctta acccagaccg ccgctcgcga cctcgcgccg ctgggcatca cggtcaacgg    840
ctactgcccg gggattgtca aaacgccaat gtgggccgaa attgaccgcc aggtgtccga    900
agccgccggt aaaccgctgg gctacggtac cgccgagttc gccaaacgca tcaccctcgg    960
ccgcctgtcc gagccggaag atgtcgccgc ctgcgtctcc tatcttgcca gcccggattc   1020
tgattatatg accggtcagt cattgctgat cgacggcggg atggtgttta actaagatag   1080
cttggatgtt gtacaggata atgtccagaa ggtcgataga aagcgtgaga acagcgtac    1140
agacgattta gagatgtaga ggtactttta tgccgagaaa acttttttgcg tgtgacagtc   1200
cttaaaatat acttagagcg taagcgaaag tagtagcgac agctattaac tttcggttgc   1260
aaagctctag gatttttaat ggacgcagcg catcacacgc aaaaggaaa ttggaataaa    1320
tgcgaaattt gagatgttaa ttaaagacct ttttgaggtc tttttttctt agattttgg    1380
ggttatttag gggagaaaac ataggggggt actacgacct cccccctagg tgtccattgt   1440
ccattgtcca aacaaataaa taaatattgg gttttaatg ttaaaaggtt gtttttatg    1500
ttaaagtgaa aaaacagat gttgggaggt acagtgatag ttgtagatag aaagaagag    1560
aaaaaagttg ctgttacttt aagacttaca acagaagaaa atgagatatt aaatagaatc   1620
aaagaaaaat ataatattag caaatcagat gcaaccggta ttctaataaa aaaatatgca   1680
aaggaggaat acggtgcatt ttaaacaaaa aaagatagac agcactggca tgctgcctat   1740
ctatgactaa attttgttaa gtgtattagc accgttatta tatcatgagc gaaaatgtaa   1800
taaaagaaac tgaaaacaag aaaaattcaa gaggacgtaa ttggacattt gttttatatc   1860
cagaatcagc aaaagccgag tggttagagt atttaaaaga gttacacatt caatttgtag   1920
tgtctccatt acatgatagg gatactgata cagaaggtag gatgaaaaaa gagcattatc   1980
atattctagt gatgtatgag ggtaataaat cttatgaaca gataaaaata attaacagaa   2040
gaattgaatc gactattcc gcagattgca ggaagtgtga aaggtcttgt gagatatatg   2100
cttcacatgg acgatcctaa taaatttaaa tatcaaaaag aagatatgat agtttatggc   2160
ggtgtagatg ttgatgaatt attaaagaaa acaacaacag atagatataa attaattaaa   2220
gaaatgattg agtttattga tgaacaagga atcgtagaat ttaagagttt aatggattat   2280
gcaatgaagt ttaaatttga tgattggttc ccgcttttat gtgataactc ggcgtatgtt   2340
attcaagaat atataaaatc aaatcggtat aaatctgacc gatagatttt gaatttaggt   2400
gtcacaagac actctttttt cgcaccagcg aaaactggtt taagccgact gcgcaaaaga   2460
cataatcgat tcacaaaaaa taggcacacg aaaaacaagt taagggatgc agtttatgca   2520
tcccttaact tacttattaa ataatttata gctattgaaa agagataaga attgttcaaa   2580
gctaatattg tttaaatcgt caattcctgc atgttttaag gaattgttaa attgattttt   2640
tgtaaatatt ttcttgtatt ctttgttaac ccatttcata acgaaataat tatacttttg   2700
tttatctttg tgtgatattc ttgatttttt tctacttaat ctgataagtg agctattcac   2760
tttaggttta ggatgaaaat attctcttgg aaccatactt aatatagaaa tatcaacttc   2820
tgccattaaa agtaatgcca atgagcgttt tgtatttaat aatctttag caaacccgta   2880
ttccacgatt aaataaatct cattagctat actatcaaaa acaattttgc gtattatatc   2940
cgtacttatg ttataaggta tattaccata tattttatag gattggtttt taggaaattt   3000
```

-continued

```
aaactgcaat atatccttgt ttaaaacttg gaaattatcg tgatcaacaa gtttattttc    3060
tgtagttttg cataatttat ggtctatttc aatggcagtt acgaaattac acctctttac    3120
taattcaagg gtaaaatggc cttttcctga gccgatttca agatattat catgttcatt     3180
taatcttata tttgtcatta ttttatctat attatgtttt gaagtaataa agttttgact    3240
gtgttttata tttttctcgt tcattataac cctctttaat ttggttatat gaattttgct    3300
tattaacgat tcattataac cacttatttt ttgtttggtt gataatgaac tgtgctgatt    3360
acaaaaatac taaaaatgcc catattttt cctccttata aaattagtat aattatagca     3420
cgagctctga taaatatgaa catgatgagt gatcgttaaa tttatactgc aatcggatgc    3480
gattattgaa taaagatat gagagattta tctaatttct tttttcttgt aaaaaaagaa     3540
agttcttaaa ggttttatag ttttggtcgt agagcacacg gttaacgac ttaattacga     3600
agtaaataag tctagtgtgt tagactttat gaaatctata tacgtttata tatatttatt    3660
atccggatct gcatcgcagg atgctgctgg ctaccctgtg gaacacctac atctgtatta    3720
acgaagcgct ggcattgacc ctgagtgatt tttctctggt cccgccgcat ccataccgcc    3780
agttgtttac cctcacaacg ttccagtaac cgggcatgtt catcatcagt aacccgtatc    3840
gtgagcatcc tctctcgttt catcggtatc attaccccca tgaacagaaa ttcccccta    3900
cacggaggca tcaagtgacc aaacaggaaa aaaccgccct taacatggcc cgctttatca    3960
gaagccagac attaacgctt ctggagaaac tcaacgagct ggacgcggat gaacaggcag    4020
acatctgtga atcgcttcac gaccacgctg atgagcttta ccgcagctgc ctcgcgcgtt    4080
tcggtgatga cggtgaaaac ctctgacaca tgcagctccc ggagacggtc acagcttgtc    4140
tgtaagcgga tgccgggagc agacaagccc gtcaggcgc gtcagcgggt gttggcgggt     4200
gtcggggcgc agccatgacc cagtcacgta gcgatagcgg agtgtatact ggcttaacta    4260
tgcggcatca gagcagattg tactgagagt gcaccatatg cggtgtgaaa taccgcacag    4320
atgcgtaagg agaaaatacc gcatcaggcg ctcttccgct tcctcgctca ctgactcgct    4380
gcgctcggtc gttcggctgc ggcgagcggt atcagctcac tcaaaggcgg taatacggtt    4440
atccacagaa tcaggggata acgcaggaaa gaacatgtga gcaaaaggcc agcaaaaggc    4500
caggaaccgt aaaaaggccg cgttgctggc gttttttccat aggctccgcc cccctgacga    4560
gcatcacaaa aatcgacgct caagtcagag gtggcgaaac ccgacaggac tataaagata    4620
ccaggcgttt ccccctggaa gctccctcgt gcgctctcct gttccgaccc tgccgcttac    4680
cggatacctg tccgcctttc tcccttcggg aagcgtggcg ctttctcaat gctcacgctg    4740
taggtatctc agttcggtgt aggtcgttcg ctccaagctg ggctgtgtgc acgaaccccc    4800
cgttcagccc gaccgctgcg ccttatccgg taactatcgt cttgagtcca acccggtaag    4860
acacgactta tcgccactgg cagcagccac tggtaacagg attagcagag cgaggtatgt    4920
aggcggtgct acagagttct tgaagtggtg gcctaactac ggctacacta aaggacagt     4980
atttggtatc tgcgctctgc tgaagccagt taccttcgga aaaagagttg gtagctcttg    5040
atccggcaaa caaaccaccg ctggtagcgg tggttttttt gtttgcaagc agcagattac    5100
gcgcagaaaa aaaggatctc aagaagatcc tttgatcttt tctacggggt ctgacgctca    5160
gtggaacgaa aactcacgtt aagggatttt ggtcatgaga ttatcaaaaa ggatcttcac    5220
ctagatcctt ttaaattaaa aatgaagttt taaatcaatc taaagtatat atgagtaaac    5280
ttggtctgac agttaccaat gcttaatcag t                                   5311
```

<210> SEQ ID NO 39
<211> LENGTH: 31
<212> TYPE: DNA
<213> ORGANISM: artificial sequence
<220> FEATURE:
<223> OTHER INFORMATION: primer

<400> SEQUENCE: 39
catgaattcg tgctaagagc cagattgtgg a                                31

<210> SEQ ID NO 40
<211> LENGTH: 50
<212> TYPE: DNA
<213> ORGANISM: artificial sequence
<220> FEATURE:
<223> OTHER INFORMATION: primer

<400> SEQUENCE: 40
catgaagacc acgcgtaggc cttctagagc taaattttca catcgtgagc             50

<210> SEQ ID NO 41
<211> LENGTH: 49
<212> TYPE: DNA
<213> ORGANISM: artificial sequence
<220> FEATURE:
<223> OTHER INFORMATION: primer

<400> SEQUENCE: 41
atttagctct agaaggccta cgcgtggtct tcatgaactt gttcaaccg              49

<210> SEQ ID NO 42
<211> LENGTH: 31
<212> TYPE: DNA
<213> ORGANISM: artificial sequence
<220> FEATURE:
<223> OTHER INFORMATION: primer

<400> SEQUENCE: 42
catctcgagc caagctcagt cacgcattta a                                31

<210> SEQ ID NO 43
<211> LENGTH: 22
<212> TYPE: DNA
<213> ORGANISM: artificial sequence
<220> FEATURE:
<223> OTHER INFORMATION: primer

<400> SEQUENCE: 43
aagcacaacg ggaagcgaac at                                          22

<210> SEQ ID NO 44
<211> LENGTH: 23
<212> TYPE: DNA
<213> ORGANISM: artificial sequence
<220> FEATURE:
<223> OTHER INFORMATION: primer

<400> SEQUENCE: 44
atacaactat gacgctggaa gcg                                         23

<210> SEQ ID NO 45
<211> LENGTH: 23
<212> TYPE: DNA
<213> ORGANISM: artificial sequence
<220> FEATURE:
<223> OTHER INFORMATION: primer

```
<400> SEQUENCE: 45
gtaggttttc ccgtccttga tag                                             23

<210> SEQ ID NO 46
<211> LENGTH: 35
<212> TYPE: DNA
<213> ORGANISM: artificial sequence
<220> FEATURE:
<223> OTHER INFORMATION: primer

<400> SEQUENCE: 46
tataagatct tgactctggt gaacttgtcg caacc                                35

<210> SEQ ID NO 47
<211> LENGTH: 34
<212> TYPE: DNA
<213> ORGANISM: artificial sequence
<220> FEATURE:
<223> OTHER INFORMATION: primer

<400> SEQUENCE: 47
atatctcgag aataagtcat cctctcgtag tgaa                                 34

<210> SEQ ID NO 48
<211> LENGTH: 34
<212> TYPE: DNA
<213> ORGANISM: artificial sequence
<220> FEATURE:
<223> OTHER INFORMATION: primer

<400> SEQUENCE: 48
tatactcgag taatcatttc atacgattaa atgt                                 34

<210> SEQ ID NO 49
<211> LENGTH: 32
<212> TYPE: DNA
<213> ORGANISM: artificial sequence
<220> FEATURE:
<223> OTHER INFORMATION: primer

<400> SEQUENCE: 49
atatcccggg gtgagcgggt aaagtccttg cc                                   32

<210> SEQ ID NO 50
<211> LENGTH: 69
<212> TYPE: DNA
<213> ORGANISM: artificial sequence
<220> FEATURE:
<223> OTHER INFORMATION: primer

<400> SEQUENCE: 50
tatactcgag gctagcatat gatatcatat ataggaggaa ttttttgtaat gaaagctctg    60 gtttatcac                                                             69

<210> SEQ ID NO 51
<211> LENGTH: 22
<212> TYPE: DNA
<213> ORGANISM: artificial sequence
<220> FEATURE:
<223> OTHER INFORMATION: primer

<400> SEQUENCE: 51
atatatagga ggaattttg ta                                               22
```

<210> SEQ ID NO 52
<211> LENGTH: 34
<212> TYPE: DNA
<213> ORGANISM: artificial sequence
<220> FEATURE:
<223> OTHER INFORMATION: primer

<400> SEQUENCE: 52
tataggtacc tcaggcagcg cctgcgttcg agag                        34

<210> SEQ ID NO 53
<211> LENGTH: 21
<212> TYPE: DNA
<213> ORGANISM: artificial sequence
<220> FEATURE:
<223> OTHER INFORMATION: primer

<400> SEQUENCE: 53
cgggcacctg caaccgaggt c                                      21

<210> SEQ ID NO 54
<211> LENGTH: 22
<212> TYPE: DNA
<213> ORGANISM: artificial sequence
<220> FEATURE:
<223> OTHER INFORMATION: primer

<400> SEQUENCE: 54
ctgtttctca cgctttctat cg                                     22

<210> SEQ ID NO 55
<211> LENGTH: 22
<212> TYPE: DNA
<213> ORGANISM: artificial sequence
<220> FEATURE:
<223> OTHER INFORMATION: primer

<400> SEQUENCE: 55
gattttcttt atcaacttcg ac                                     22

<210> SEQ ID NO 56
<211> LENGTH: 55
<212> TYPE: DNA
<213> ORGANISM: artificial sequence
<220> FEATURE:
<223> OTHER INFORMATION: primer

<400> SEQUENCE: 56
tatagctagc atatatagga ggaattttg taatgaaaaa agtcgcactt gttac    55

<210> SEQ ID NO 57
<211> LENGTH: 31
<212> TYPE: DNA
<213> ORGANISM: artificial sequence
<220> FEATURE:
<223> OTHER INFORMATION: primer

<400> SEQUENCE: 57
tatagatatc ttagttaaac accatcccgc c                           31

<210> SEQ ID NO 58
<211> LENGTH: 21
<212> TYPE: DNA
<213> ORGANISM: artificial sequence
<220> FEATURE:
<223> OTHER INFORMATION: primer

<400> SEQUENCE: 58
ttggaaaacg ttcttcgggg c                                              21

<210> SEQ ID NO 59
<211> LENGTH: 49
<212> TYPE: DNA
<213> ORGANISM: artificial sequence
<220> FEATURE:
<223> OTHER INFORMATION: primer

<400> SEQUENCE: 59
atgttgtaca aaacaggagg gccaaaatca tgggcaatta cgattcaac                49

<210> SEQ ID NO 60
<211> LENGTH: 34
<212> TYPE: DNA
<213> ORGANISM: artificial sequence
<220> FEATURE:
<223> OTHER INFORMATION: primer

<400> SEQUENCE: 60
atcctgtaca ctaaccaccg atttggcaat gtag                                34

<210> SEQ ID NO 61
<211> LENGTH: 46
<212> TYPE: DNA
<213> ORGANISM: artificial sequence
<220> FEATURE:
<223> OTHER INFORMATION: primer

<400> SEQUENCE: 61
tagaattcgt gaattccact agtcttaagt aagtcgtatt ggcacc                   46

<210> SEQ ID NO 62
<211> LENGTH: 47
<212> TYPE: DNA
<213> ORGANISM: artificial sequence
<220> FEATURE:
<223> OTHER INFORMATION: primer

<400> SEQUENCE: 62
acttgtagga ctcgaggctt gacaaaataa gtcatcctct cgtagtg                  47

<210> SEQ ID NO 63
<211> LENGTH: 1053
<212> TYPE: DNA
<213> ORGANISM: Bacillus cereus

<400> SEQUENCE: 63
atgaaagcac tactttggca taatcaacgt gatgtacgag tagaagaagt accagaacca    60
acagtaaaac caggaacagt gaaaatcaaa gttaaatggt gtggtatttg tgggacagac 120
ttgcatgaat atttagcagg gcctattttt attccaacag aagaacatcc attaacacat 180
gtgaaagcac ctgttatttt aggtcatgag tttagtggtg aggtaataga gattggtgaa 240
ggagttacat ctcataaagt gggagaccgc gttgttgtag agccaattta ttcttgtggt 300
aaatgtgaag cttgtaaaca tggacattac aatgtttgtg aacaacttgt tttccacggt 360
cttggcggag aaggcggcgg tttctctgaa tatacagtag taccagaaga tatggttcat 420
cacattccag atgaaatgac gtatgaacaa ggtgcgcttg tagaaccagc agcagtagca 480
gttcatgcag tacgtcaaag taaattaaaa gaaggggaag ctgtagcggt atttggttgc 540

-continued

```
ggtccaattg gacttcttgt tatccaagca gctaaagcag caggagcaac tcctgttatt    600
gcagttgaac tttctaaaga acgtcaagag ttagcgaaat tagcaggtgc ggattatgta    660
ttaaatccag caactcaaga tgtgttagct gaaattcgta acttaacaaa tggtttaggt    720
gtaaatgtta gctttgaagt aacaggtgtt gaagttgtac tacgccaagc gattgaaagt    780
acaagcttcg aaggacaaac tgtaattgtt agtgtatggg aaaaagacgc aacaattact    840
ccaaataact tagtattaaa agaaaaagaa gttattggta ttttaggata ccgtcacatc    900
ttcccagctg ttattaaatt gattagctcc ggtcaaattc aagcagagaa attaattacg    960
aaaaaaatta cagtggatca agttgttgaa gaaggatttg aagcacttgt aaaagataaa    1020
acacaagtga aaattcttgt ttcacctaaa taa                                1053
```

<210> SEQ ID NO 64
<211> LENGTH: 350
<212> TYPE: PRT
<213> ORGANISM: Bacillus cereus

<400> SEQUENCE: 64

```
Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Ile Glu Ile Gly Glu
65                  70                  75                  80

Gly Val Thr Ser His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Glu Gly Gly Gly Phe
        115                 120                 125

Ser Glu Tyr Thr Val Val Pro Glu Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285
```

```
Lys Glu Val Ile Gly Ile Leu Gly Tyr Arg His Ile Phe Pro Ala Val
            290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Thr Gln Val Lys Ile Leu Val Ser Pro Lys
            340                 345                 350

<210> SEQ ID NO 65
<211> LENGTH: 1113
<212> TYPE: DNA
<213> ORGANISM: Lactococcus lactis

<400> SEQUENCE: 65
ttgcctgaaa cgacaaccat cctatataga ggaggcgttt ttatgcgcgc agcacgtttt      60
tacgaccgcg gggatatccg cattgatgaa attaatgaac caatagtaaa agctggccaa     120
gttggcattg atgtggcttg gtgtggaatt tgtggaacag atctccatga attttagat      180 ggcccaattt tttgtccgtc agcagaacat cctaatccaa ttactggaga agtaccacca     240
gtcactcttg acatgaaat gtctggggtt gtaaatttta taggtgaagg agtaagcgga      300
cttaaagtag gtgaccatgt cgttgtcgaa ccttatatcg ttcccgaagg gactgataca     360
agtgaaactg acattataa cctctcagaa ggctcaaact ttattggttt gggcggaaat     420
ggtggaggtt tggctgaaaa aatttctgtt gatgaacgtt gggttcacaa aattcctgat     480
aacttaccat tggatgaagc tgctctaatt gagccactat cagtcggcta tcacgctgtt     540
gaacgagcaa atttaagtga aaagagtacg gtattagttg ttggtgctgg accaattgga     600
ctattaactg ctgccgttgc aaaagcgcaa ggacatactg ttatcatcag tgaacctagt     660
ggacttcgtc gtaaaaaagc acaagaagca caagttgctg attatttctt caatccaatt     720
gaagatgaca ttcaagctaa agttcatgaa attaatgaaa aaggagtgga cgcagccttt     780
gaatgtacct ctgtccaacc gggatttgac gcttgtctag atgcgattcg tatgggtgga     840
acagttgtca ttgtcgcaat ttggggcaag cctgctagtg ttgatatggc aaaattagta     900
atcaaagaag ctaacctttt aggaacgatt gcttataata acactcatcc aaaaacaatt     960
gatttagtat caacaggtaa aataaaattg gaccaattca tcacagctaa atcggtttg    1020 gatgatttga ttgataaagg attcgatacg ctgattcatc ataatgaaac agctgttaaa    1080
attttagttt caccaactgg taaaggtcta taa                                 1113

<210> SEQ ID NO 66
<211> LENGTH: 370
<212> TYPE: PRT
<213> ORGANISM: Lactococcus lactis

<400> SEQUENCE: 66

Met Pro Glu Thr Thr Thr Ile Leu Tyr Arg Gly Gly Val Phe Met Arg
1               5                  10                  15

Ala Ala Arg Phe Tyr Asp Arg Gly Asp Ile Arg Ile Asp Glu Ile Asn
                20                  25                  30

Glu Pro Ile Val Lys Ala Gly Gln Val Gly Ile Asp Val Ala Trp Cys
            35                  40                  45

Gly Ile Cys Gly Thr Asp Leu His Glu Phe Leu Asp Gly Pro Ile Phe
        50                  55                  60
```

Cys Pro Ser Ala Glu His Pro Asn Pro Ile Thr Gly Glu Val Pro Pro
 65                  70                  75                  80

Val Thr Leu Gly His Glu Met Ser Gly Val Val Asn Phe Ile Gly Glu
                 85                  90                  95

Gly Val Ser Gly Leu Lys Val Gly Asp His Val Val Glu Pro Tyr
            100                 105                 110

Ile Val Pro Glu Gly Thr Asp Thr Ser Glu Thr Gly His Tyr Asn Leu
            115                 120                 125

Ser Glu Gly Ser Asn Phe Ile Gly Leu Gly Gly Asn Gly Gly Gly Leu
130                 135                 140

Ala Glu Lys Ile Ser Val Asp Glu Arg Trp Val His Lys Ile Pro Asp
145                 150                 155                 160

Asn Leu Pro Leu Asp Glu Ala Ala Leu Ile Glu Pro Leu Ser Val Gly
                165                 170                 175

Tyr His Ala Val Glu Arg Ala Asn Leu Ser Glu Lys Ser Thr Val Leu
            180                 185                 190

Val Val Gly Ala Gly Pro Ile Gly Leu Leu Thr Ala Ala Val Ala Lys
        195                 200                 205

Ala Gln Gly His Thr Val Ile Ile Ser Glu Pro Ser Gly Leu Arg Arg
210                 215                 220

Lys Lys Ala Gln Glu Ala Gln Val Ala Asp Tyr Phe Phe Asn Pro Ile
225                 230                 235                 240

Glu Asp Asp Ile Gln Ala Lys Val His Glu Ile Asn Glu Lys Gly Val
                245                 250                 255

Asp Ala Ala Phe Glu Cys Thr Ser Val Gln Pro Gly Phe Asp Ala Cys
            260                 265                 270

Leu Asp Ala Ile Arg Met Gly Gly Thr Val Val Ile Val Ala Ile Trp
        275                 280                 285

Gly Lys Pro Ala Ser Val Asp Met Ala Lys Leu Val Ile Lys Glu Ala
290                 295                 300

Asn Leu Leu Gly Thr Ile Ala Tyr Asn Asn Thr His Pro Lys Thr Ile
305                 310                 315                 320

Asp Leu Val Ser Thr Gly Lys Ile Lys Leu Asp Gln Phe Ile Thr Ala
                325                 330                 335

Lys Ile Gly Leu Asp Asp Leu Ile Asp Lys Gly Phe Asp Thr Leu Ile
            340                 345                 350

His His Asn Glu Thr Ala Val Lys Ile Leu Val Ser Pro Thr Gly Lys
        355                 360                 365

Gly Leu
370

<210> SEQ ID NO 67
<211> LENGTH: 3378
<212> TYPE: DNA
<213> ORGANISM: artificial sequence
<220> FEATURE:
<223> OTHER INFORMATION: synthesized double coding region

<400> SEQUENCE: 67
ggatccgttt aaacaggagg gccaaaatca tgggcaatta cgattcaaca ccgatagcta    60
aaagtgatag gattaaaaga ttggttgatc atttgtatgc taaaatgcct gaaattgagg   120
ccgctagagc agagctaatt actgaatcct ttaaggccac cgaaggtcaa cctgttgtta   180
tgagaaaggc tagagctttt gaacatatac taaagaattt gccaattatc ataagaccag   240
aagaactgat tgttggctca actacaattg cccctagagg ttgccaaacg tatccagaat   300

```
tctcatacga gtggttagag gctgaatttg aaactgtcga aacgcgttca gctgacccat    360
tttatatttc agaagaaacg aagaaacgtt tgctggctgc cgatgcttat tggaaaggta    420
aaacaacctc agagttggca acttcatata tggccccaga aactctaaga gccatgaagc    480
ataacttctt caccccgtgga aactactcct acaatggtgt cggtcatgtc acagttcaat    540
atgaaacagt attagcaatc ggcttgaatg gagtaaaaga gaaggttagg aaagagatgg    600
agaattgtca ttttggtgat gccgattata gtacaaagat gtgtttcttg gagagcattt    660
taatatcgtg tgatgccgta atcacttatg ctaatagata tgccaagatg gccgaggaaa    720
tggctgaaaa agaaacagat gctgcaagga ggcaagaact attaacaatc gccagggttt    780
gcaaaaacgt tcctgaattc ccagccgaaa gcttccagga ggcctgccaa tccttttggt    840
tcatacaaca agtgcttcaa attgaatcca gtggtcattc aatttcccca ggtagatttg    900
atcaatatat gtatccttat tacgaaaagg atttaaagga aggtagctta actagggaat    960
atgctcagga actgatcgat tgtatctggg ttaagttaaa tgatctgaat aagtgcaggg    1020
atgctgcctc tgctgagggc tttgcaggat attccttatt tcaaaactta atcgttgggg    1080
gccaaacggt tcaaggaagg gacgccacca atgatttgag ttttatgtgt atcacggcat    1140
ctgaacacgt cttttttaccg atgccgtcgt tgtctataag agtttggcat ggtagttcca    1200
aagcactgct tatgagagca gctgaattga ctagaaccgg tataggctta cctgcttatt    1260
acaatgatga agtcatcata ccagctttgg tgcatagggg tgctactatg gatgaagcaa    1320
gaaattacaa cataataggga tgtgtcgaac cgcaggttcc tggtaaaact gatggctggc    1380
acgatgcagc attctttaac atgtgcagac ctttggaaat ggtgtttagt aatggttatg    1440
ataacggtga aattgcatct atacaaactg gtaacgtaga atcttttcag agttttgatg    1500
agtttatgga agcttacaga aaacaaatgc tatataacat agaacttatg gtaaatgccg    1560
acaacgcgat agattatgcc cacgcaaagt tggccccatt gccatttgag tcatgtttgg    1620
ttgatgactg tataaagaga ggaatgtccg ctcaggaagg cggcgcaatc tataatttca    1680
ctggtccaca gggctttggt attgcaaacg ttgctgatag cttgtatacg attaagaaat    1740
tggtgttcga ggagaagaga attacgatgg gtgaattaaa gaaagcgttg gaaatgaatt    1800
atggtaaggg tttggatgcc acaaccgctg gtgacatcgc aatgcaggtc gcgaagggac    1860
taaaagatgc cggacaggaa gtgggtcccg acgtgatcgc taatacaatc cgtcaagttc    1920
ttgaaatgga attaccagaa gatgtaagaa agagatatga agagatccat gaaatgatac    1980
ttgagttacc aaagtatggt aatgatatag atgaagttga tgaattagct agagaagcag    2040
cttacttta cacaagacca ttagaaactt ttaagaatcc aagggggtggc atgtatcaag    2100
ccggcccttta tcccgtgtcc gctaatgtgc cactaggcgc tcaaacgggg gccacacccg    2160
atggacgttt ggcgcataca cccgtggcgg atggcgttgg tccgacatca ggcttcgata    2220
tatccggacc aacagcttct tgcaattctg tcgccaagtt ggatcatgct atagcctcta    2280
atggtacctt atttaatatg aagatgcacc caaccgcaat ggcaggtgaa aagggcttag    2340
aatccttcat atcgttgatc cgtggttatt tcgatcaaca aggtatgcac atgcaatttta    2400
acgtagtaga cagggctaca ctgctttgatg cgcaggccca ccctgaaaag tattcaggct    2460
taattgtcag agtggcaggt tattctgccc tttttaccac attgtccaag tcattacaag    2520
atgatataat caaacgtacc gaacaagcag acaatagata ggaaggaaaa acgcgttatg    2580
aaagaatatc ttaatacttc aggtagaata tttgatatcc agaggtattc tattcacgat    2640
```

```
ggccctggtg tgcgtacaat tgtgtttcta aaaggttgtg cccttagatg cagatggtgc    2700
tgtaatcctg aaagccaaag cttcgaagtt gaaacaatga cgattaatgg aaaacctaaa    2760
gtcatgggta aagatgttac agtcgccgag gttatgaaga cggtagaaag agacatgcct    2820
tattaccttc aatcaggtgg tggtatcacc ttatcgggtg cgaatgtac tttgcaacca     2880 gaattttccc ttggcctatt gagagctgca aaggatttgg gcatatccac ggcaatagag    2940
agcatggcgt acgcaaagta cgaagtaata gaaactcttc ttccgtatt ggatacgtat     3000 ttaatggaca tcaaacatat gaatcctgag aaacataaag aatacactgg tcatgataac    3060
ttgaggatgt tagaaaacgc cttaagagtc gcgcattctg gtcagaccga actgatcatc    3120
agagtacctg tcatcccagg attcaacgca actgagcagg aactactaga tattgcaaaa    3180
ttcgcagata cactgcctgg agttagacaa atacacatct tgccatatca taattttggt    3240
cagggtaaat acgaaggatt gaacagggac tatccgatgg gggacactga gaaaccctct    3300
aatgaacaga tgaaagcttt tcaagaaatg attcaaaaga cacttccct acattgccaa     3360 atcggtggtt aggtcgac                                                   3378

<210> SEQ ID NO 68
<400> SEQUENCE: 68

000

<210> SEQ ID NO 69
<211> LENGTH: 2445
<212> TYPE: DNA
<213> ORGANISM: Lactobacillus plantarum

<400> SEQUENCE: 69
atgatcatgt ctgaaacttt aactaaaaca acgacaacta ttaaccactt cggtaaattg      60
acgccaatga tggatcgctt acgcgatagc atcattgatg caaaacctta tgtcgatcca     120
gaacgggcga ttctcacaac cgaaacttat cgacaacacc aagacgaaca agtcgatata     180
ttacgggcta aaatgcttga acacgttctt gataaaatga gtatcttcat tgaagatgat     240
actttaattg ttggtaacca agcacgccaa atcgttggg caccagtatt ccctgagtat      300
tctatgaatt gggtcattga tgaattagat acatttgaga agcgtcctgg tgacgttttc     360
tatattacgg agaaatccaa ggaagaactt cgtgcgattg cgccttctg gaaacataat      420 accttggaag accgcggcta cgctagtttt ccagaagcaa gtcgtatttt ttatgattta     480
ggtattattg gagccgatgg taatatcact tctggtgatg gtcacattgc ggtcgactat     540
aaaaacgttg ttaataaggg acttaaatgg tatgaagacc gcattaagac agcacttgct     600
aatcttgacc ttactgattt taaccagcaa aaacaatact atttctataa agcgggccta     660
attgtaattg atgccattca caattttgct aaacgttacg cccaattagc gtccaagcaa     720
gctcaaaaca cgacatccgc aactcgcaaa gcacaacttg aaaaaatcgc caaattcta     780 aacaaggttc cttacgaacc tgcaaattca tttatgaag cgattcaagc tgtctggtta     840
gttcatctga cctttacaaat cgaatccaac ggtcattctg tctcatatgg tcgtctagat     900
cagtacctag ctccattcta tgagcacgat ttaaaaactg tgctattga cgccaacggt     960 gcaaccgaat tactcacaaa cttatgtctt aagacgttaa cgattaataa agtacgctca    1020
tggcaacata ctgaattttc tgcagggagt ccccctctacc aaaacattac gattggtggt    1080
caaacaccag atggtaaaga tgccgttaat ccgacgtcct atctgatttt acgagcaatt    1140
```

```
gcgcaagcac atttaccaca acccaactta acggtccgtt atcaccatgg cttaagcgat   1200
aagtttatgc gtgaatgtgt cgaagttatt aaacaaggct taggtatgcc tgcgtttaat   1260
aacgacgaaa ttattattcc gtcgtttatt cgtcgtggcg tcaagaaaga agacgcctat   1320
aattacagtg ccatcggttg tgtcgaaaca gcgatccctg aaaatgggg ctatcgttgc    1380 accgggatga gcttcattaa cttcccacgc gttctcttac tcattatgaa tggtggcatt   1440
gatcctgaat ctggcaaacg gttattaccc gattatggta agttcactga tatgacttct   1500
tttgatcaac ttatgactgc ttgggacaaa gcgctccgtg aaatgacacg acaaagtgtg   1560
attatcgaaa atagttgtga tttggctttg aacaaaatt atcctgatat tctctgctcc    1620
gttttaaccg acgattgtat cggtcgtggt aagaccatta agaaggtgg cgcggtatac    1680 gactttatca gtggattaca agttggtatt gctaacctag cggactccct agctgcaatc   1740
aagaaacttg tctttgaaga aaagaagttg acaacaaccc aactttggca cgcacttacc   1800
actgattttg cggatgaaga tggtgaaaag attcggcaga tgctcattaa tgatgcccca   1860
aagtatggta acgatgatga ttatgttgat gatttgattg ttgaagctta taaccatat    1920 attgatgaaa ttgccaagta caaaaacacg cgctacggtc gcggccctat tggtggcttg   1980
cgctacgcag gaacctcttc tatttcggcc aacgttggtc aagggcacag cactttggct   2040
acaccagatg gtcggcacgc tcggacacca ttagccgaag gttgctcacc agaacatgca   2100
atggatactg atggcccaac tgctgtgttc aaatcagttt ccaaattatc cactaaggac   2160
atcactggtg gcgtattact gaaccaaaag atgtcaccac aaattctacg gagtgatgaa   2220
agctgcatga aattggttgc actactacgg accttcttca atcgacttca tggttaccat   2280
gtccaataca acattgtttc acgggatacc ttgattgatg cacagaacca tcctgacaag   2340
caccgtgact tgattgttcg ggttgctgga tattccgcct tcttcgtggg cctatccaaa   2400
gaaacccaag atgatattat cgaacggacg gagcagtctc tataa                  2445
```

<210> SEQ ID NO 70
<211> LENGTH: 814
<212> TYPE: PRT
<213> ORGANISM: Lactobacillus plantarum

<400> SEQUENCE: 70

```
Met Ile Met Ser Glu Thr Leu Thr Lys Thr Thr Thr Ile Asn His
1               5                   10                  15

Phe Gly Lys Leu Thr Pro Met Met Asp Arg Leu Arg Asp Ser Ile Ile
                20                  25                  30

Asp Ala Lys Pro Tyr Val Asp Pro Glu Arg Ala Ile Leu Thr Thr Glu
            35                  40                  45

Thr Tyr Arg Gln His Gln Asp Glu Gln Val Asp Ile Leu Arg Ala Lys
        50                  55                  60

Met Leu Glu His Val Leu Asp Lys Met Ser Ile Phe Ile Glu Asp Asp
65                  70                  75                  80

Thr Leu Ile Val Gly Asn Gln Ala Arg Gln Asn Arg Trp Ala Pro Val
                85                  90                  95

Phe Pro Glu Tyr Ser Met Asn Trp Val Ile Asp Glu Leu Asp Thr Phe
                100                 105                 110

Glu Lys Arg Pro Gly Asp Val Phe Tyr Ile Thr Glu Lys Ser Lys Glu
            115                 120                 125

Glu Leu Arg Ala Ile Ala Pro Phe Trp Lys His Asn Thr Leu Glu Asp
        130                 135                 140
```

-continued

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
                165                 170                 175

Ala Val Asp Tyr Lys Asn Val Val Asn Lys Gly Leu Lys Trp Tyr Glu
                180                 185                 190

Asp Arg Ile Lys Thr Ala Leu Ala Asn Leu Asp Leu Thr Asp Phe Asn
                195                 200                 205

Gln Gln Lys Gln Tyr Tyr Phe Tyr Lys Ala Gly Leu Ile Val Ile Asp
210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
                245                 250                 255

Ala Gln Ile Leu Asn Lys Val Pro Tyr Glu Pro Ala Asn Ser Phe Tyr
                260                 265                 270

Glu Ala Ile Gln Ala Val Trp Leu Val His Leu Thr Leu Gln Ile Glu
                275                 280                 285

Ser Asn Gly His Ser Val Ser Tyr Gly Arg Leu Asp Gln Tyr Leu Ala
290                 295                 300

Pro Phe Tyr Glu His Asp Leu Lys Thr Gly Ala Ile Asp Ala Asn Gly
305                 310                 315                 320

Ala Thr Glu Leu Leu Thr Asn Leu Cys Leu Lys Thr Leu Thr Ile Asn
                325                 330                 335

Lys Val Arg Ser Trp Gln His Thr Glu Phe Ser Ala Gly Ser Pro Leu
                340                 345                 350

Tyr Gln Asn Ile Thr Ile Gly Gly Gln Thr Pro Asp Gly Lys Asp Ala
                355                 360                 365

Val Asn Pro Thr Ser Tyr Leu Ile Leu Arg Ala Ile Ala Gln Ala His
                370                 375                 380

Leu Pro Gln Pro Asn Leu Thr Val Arg Tyr His His Gly Leu Ser Asp
385                 390                 395                 400

Lys Phe Met Arg Glu Cys Val Glu Val Ile Lys Gln Gly Leu Gly Met
                405                 410                 415

Pro Ala Phe Asn Asn Asp Glu Ile Ile Pro Ser Phe Ile Arg Arg
                420                 425                 430

Gly Val Lys Lys Glu Asp Ala Tyr Asn Tyr Ser Ala Ile Gly Cys Val
                435                 440                 445

Glu Thr Ala Ile Pro Gly Lys Trp Gly Tyr Arg Cys Thr Gly Met Ser
450                 455                 460

Phe Ile Asn Phe Pro Arg Val Leu Leu Leu Ile Met Asn Gly Gly Ile
465                 470                 475                 480

Asp Pro Glu Ser Gly Lys Arg Leu Leu Pro Asp Tyr Gly Lys Phe Thr
                485                 490                 495

Asp Met Thr Ser Phe Asp Gln Leu Met Thr Ala Trp Asp Lys Ala Leu
                500                 505                 510

Arg Glu Met Thr Arg Gln Ser Val Ile Ile Glu Asn Ser Cys Asp Leu
                515                 520                 525

Ala Leu Glu Gln Asn Tyr Pro Asp Ile Leu Cys Ser Val Leu Thr Asp
                530                 535                 540

Asp Cys Ile Gly Arg Gly Lys Thr Ile Lys Glu Gly Gly Ala Val Tyr
545                 550                 555                 560

Asp Phe Ile Ser Gly Leu Gln Val Gly Ile Ala Asn Leu Ala Asp Ser

```
                565                 570                 575
Leu Ala Ala Ile Lys Lys Leu Val Phe Glu Lys Lys Leu Thr Thr
            580                 585                 590

Thr Gln Leu Trp His Ala Leu Thr Thr Asp Phe Ala Asp Glu Asp Gly
        595                 600                 605

Glu Lys Ile Arg Gln Met Leu Ile Asn Asp Ala Pro Lys Tyr Gly Asn
    610                 615                 620

Asp Asp Asp Tyr Val Asp Asp Leu Ile Val Glu Ala Tyr Lys Pro Tyr
625                 630                 635                 640

Ile Asp Glu Ile Ala Lys Tyr Lys Asn Thr Arg Tyr Gly Arg Gly Pro
                645                 650                 655

Ile Gly Gly Leu Arg Tyr Ala Gly Thr Ser Ser Ile Ser Ala Asn Val
                660                 665                 670

Gly Gln Gly His Ser Thr Leu Ala Thr Pro Asp Gly Arg His Ala Arg
            675                 680                 685

Thr Pro Leu Ala Glu Gly Cys Ser Pro Glu His Ala Met Asp Thr Asp
        690                 695                 700

Gly Pro Thr Ala Val Phe Lys Ser Val Ser Lys Leu Ser Thr Lys Asp
705                 710                 715                 720

Ile Thr Gly Gly Val Leu Leu Asn Gln Lys Met Ser Pro Gln Ile Leu
                725                 730                 735

Arg Ser Asp Glu Ser Cys Met Lys Leu Val Ala Leu Leu Arg Thr Phe
                740                 745                 750

Phe Asn Arg Leu His Gly Tyr His Val Gln Tyr Asn Ile Val Ser Arg
            755                 760                 765

Asp Thr Leu Ile Asp Ala Gln Asn His Pro Asp Lys His Arg Asp Leu
        770                 775                 780

Ile Val Arg Val Ala Gly Tyr Ser Ala Phe Phe Val Gly Leu Ser Lys
785                 790                 795                 800

Glu Thr Gln Asp Asp Ile Ile Glu Arg Thr Glu Gln Ser Leu
                805                 810
```

<210> SEQ ID NO 71
<211> LENGTH: 2259
<212> TYPE: DNA
<213> ORGANISM: Lactobacillus plantarum

<400> SEQUENCE: 71

```
atgattacat cagaaaagac aacaaaacca gcagcttgga aaggtttcaa aggcgggcac      60
tggcaggaag aaatcaacat tcgtgatttt attcaaaata acttcacaca gtacaatggc     120
gacgaaagct tcctggccgg accaacagcc gctactaaga ccttgaatga caaagtctta     180
gaattaaaga acaagaacg tgccgctggt ggtgtgttgg atgctgatac taaagtcgtt     240
gcaacgatta cttcacacgg ccctggttat attcaaaaag atctcgaaaa gattgttggt     300
ctccagactg acaagccttt gaagcgggcc ttcatgccat tggtggtat tcgaatggct      360 gatgacgctt tgaaatcata cggttatacc cctgatgaag aaaacgacaa gattttcact     420
gaatatcgca agactcataa ccaaggcgtc ttcgatgttt atactcctga catgcggaaa     480
gcacgtcact acaagatcat caccggacta ccagatgcat acgcacgtgg ccgtctcatt     540
cctgatcttc acgggtcgc tgtttatggg atcgatcgtt taatggaaga caaagctaat     600
gactttgccc acattggtga tgtgaattg actgatgatg ttattcgcct ccgtgaagaa      660
gttcaagatc aataccgtgc tttagcagat atgaagaaga tggctgccag ttatggctac     720
```

```
gatattagca agcctgcaac taatgctcaa gaagctattc aatggatgta cttcgcttac    780
ttagctgcta tcaagaccca aaacggcgct gcaatgtccg ttggccggat tgatacaacg    840
atggacatct tcatccaacg tgacttggac aatggtgttc tggacgaaag ccaagctcaa    900
gaattaattg atcaattcgt catgaaacta cggatggttc ggttcatccg tactgaagaa    960
tacaattctc tcttctctgg tgacccaatc tgggcaacct tatcaatgtg tggtttaggc   1020
gtcgacggtc aacaccatgt gactaagact gctttccgga ttttaaagac tttgacaac    1080
atgggcgccg caccagaacc aaacatcacg attttatggt cagaccgctt accagaagac   1140
ttcaaacgtt acgcaactga agtttcaatc gacagttcaa ccattcagta tgaaaatgat   1200
gacttgatgc gggtacaatg gggtaccgat tattatggca ttgcttgctg tgtttccgca   1260
caaccaattg ctgatggaat ccagtacttc ggtgcccggg caaacttagc caaagcgatt   1320
ctttatgcca tcaatggtgg ccgcgacgaa attgctggag atcaagttgg ccctgcttac   1380
gaaccaatta cttcagaata catcgattac gacgaattca tgaagaaatt agacaagcaa   1440
atggattggt tagctgacac ttacgttaac tcactgaatg caattcatta tatgcatgat   1500
aagtactact atgaagctgc ccaattagct ttgaagaata ctgatcttga tcggaccttt   1560
gcaactggga tttctggctt atcacatgcc gcggattcaa tctcagctat caagtatggt   1620
cacgttaaag taattcgtga cgaacgtggt atcgccgttg acttcaaagc cgacaatgac   1680
tacccacgtt atgggaacaa tgacgatcgc gctgatgaca ttgctaaatg gttagtcaaa   1740
gaattataca gcaagatgaa cacgcatcac ctctatcgga atgccaaact ttcaacttct   1800
gttttgacga ttacctccaa cgttgtttat ggtaagaaca ctggtaccac gccaaatggc   1860
cgtcaaaaag gcgaaccatt ctcaccaggt gctaaccctg catacggtgc tgaaagagt    1920
ggtgcattag cttcacttct ttcaactgcc aaattaccat accgttacgc aactgacggg   1980
atttccaaca cgttcggcgt taccccctaac acgttaggcc atgacctcga atcacggaaa   2040
gacacgttag taaacatgtt agacggttac atgaagaacg atgggatgca cttgaacatc   2100
aacgtcttca ataaagacac tttgattgat gctcagaaac accctgaaga atacccaaca   2160
ttaacggttc gggtttctgg ctattgtgtc tacttcgcag atttaaccaa ggaacaacaa   2220
gatgacgtta tttcacggac attcttcgaa tcaatgtaa                          2259
```

<210> SEQ ID NO 72
<211> LENGTH: 752
<212> TYPE: PRT
<213> ORGANISM: Lactobacillus plantarum

<400> SEQUENCE: 72

```
Met Ile Thr Ser Glu Lys Thr Thr Lys Pro Ala Ala Trp Lys Gly Phe
1               5                   10                  15

Lys Gly Gly His Trp Gln Glu Glu Ile Asn Ile Arg Asp Phe Ile Gln
            20                  25                  30

Asn Asn Phe Thr Gln Tyr Asn Gly Asp Glu Ser Phe Leu Ala Gly Pro
        35                  40                  45

Thr Ala Ala Thr Lys Thr Leu Asn Asp Lys Val Leu Glu Leu Lys Lys
    50                  55                  60

Gln Glu Arg Ala Ala Gly Gly Val Leu Asp Ala Asp Thr Lys Val Val
65                  70                  75                  80

Ala Thr Ile Thr Ser His Gly Pro Gly Tyr Ile Gln Lys Asp Leu Glu
                85                  90                  95

Lys Ile Val Gly Leu Gln Thr Asp Lys Pro Leu Lys Arg Ala Phe Met
```

-continued

```
                100                 105                 110
Pro Phe Gly Gly Ile Arg Met Ala Asp Asp Ala Leu Lys Ser Tyr Gly
            115                 120                 125
Tyr Thr Pro Asp Glu Glu Asn Asp Lys Ile Phe Thr Glu Tyr Arg Lys
130                 135                 140
Thr His Asn Gln Gly Val Phe Asp Val Tyr Thr Pro Asp Met Arg Lys
145                 150                 155                 160
Ala Arg His Tyr Lys Ile Ile Thr Gly Leu Pro Asp Ala Tyr Ala Arg
                165                 170                 175
Gly Arg Leu Ile Pro Asp Leu Pro Arg Val Ala Val Tyr Gly Ile Asp
            180                 185                 190
Arg Leu Met Glu Asp Lys Ala Asn Asp Phe Ala His Ile Gly Asp Gly
            195                 200                 205
Glu Leu Thr Asp Asp Val Ile Arg Leu Arg Glu Val Gln Asp Gln
210                 215                 220
Tyr Arg Ala Leu Ala Asp Met Lys Lys Met Ala Ala Ser Tyr Gly Tyr
225                 230                 235                 240
Asp Ile Ser Lys Pro Ala Thr Asn Ala Gln Glu Ala Ile Gln Trp Met
                245                 250                 255
Tyr Phe Ala Tyr Leu Ala Ala Ile Lys Thr Gln Asn Gly Ala Ala Met
            260                 265                 270
Ser Val Gly Arg Ile Asp Thr Thr Met Asp Ile Phe Ile Gln Arg Asp
            275                 280                 285
Leu Asp Asn Gly Val Leu Asp Glu Ser Gln Ala Gln Glu Leu Ile Asp
        290                 295                 300
Gln Phe Val Met Lys Leu Arg Met Val Arg Phe Ile Arg Thr Glu Glu
305                 310                 315                 320
Tyr Asn Ser Leu Phe Ser Gly Asp Pro Ile Trp Ala Thr Leu Ser Met
                325                 330                 335
Cys Gly Leu Gly Val Asp Gly Gln His His Val Thr Lys Thr Ala Phe
            340                 345                 350
Arg Ile Leu Lys Thr Leu Asp Asn Met Gly Ala Ala Pro Glu Pro Asn
            355                 360                 365
Ile Thr Ile Leu Trp Ser Asp Arg Leu Pro Glu Asp Phe Lys Arg Tyr
        370                 375                 380
Ala Thr Glu Val Ser Ile Asp Ser Ser Thr Ile Gln Tyr Glu Asn Asp
385                 390                 395                 400
Asp Leu Met Arg Val Gln Trp Gly Thr Asp Tyr Tyr Gly Ile Ala Cys
                405                 410                 415
Cys Val Ser Ala Gln Pro Ile Ala Asp Gly Ile Gln Tyr Phe Gly Ala
            420                 425                 430
Arg Ala Asn Leu Ala Lys Ala Ile Leu Tyr Ala Ile Asn Gly Gly Arg
            435                 440                 445
Asp Glu Ile Ala Gly Asp Gln Val Gly Pro Ala Tyr Glu Pro Ile Thr
        450                 455                 460
Ser Glu Tyr Ile Asp Tyr Asp Glu Phe Met Lys Lys Leu Asp Lys Gln
465                 470                 475                 480
Met Asp Trp Leu Ala Asp Thr Tyr Val Asn Ser Leu Asn Ala Ile His
                485                 490                 495
Tyr Met His Asp Lys Tyr Tyr Glu Ala Ala Gln Leu Ala Leu Lys
            500                 505                 510
Asn Thr Asp Leu Asp Arg Thr Phe Ala Thr Gly Ile Ser Gly Leu Ser
            515                 520                 525
```

His Ala Ala Asp Ser Ile Ser Ala Ile Lys Tyr Gly His Val Lys Val
            530                 535                 540

Ile Arg Asp Glu Arg Gly Ile Ala Val Asp Phe Lys Ala Asp Asn Asp
545                 550                 555                 560

Tyr Pro Arg Tyr Gly Asn Asn Asp Asp Arg Ala Asp Asp Ile Ala Lys
                565                 570                 575

Trp Leu Val Lys Glu Leu Tyr Ser Lys Met Asn Thr His His Leu Tyr
            580                 585                 590

Arg Asn Ala Lys Leu Ser Thr Ser Val Leu Thr Ile Thr Ser Asn Val
        595                 600                 605

Val Tyr Gly Lys Asn Thr Gly Thr Thr Pro Asn Gly Arg Gln Lys Gly
        610                 615                 620

Glu Pro Phe Ser Pro Gly Ala Asn Pro Ala Tyr Gly Ala Glu Lys Ser
625                 630                 635                 640

Gly Ala Leu Ala Ser Leu Leu Ser Thr Ala Lys Leu Pro Tyr Arg Tyr
                645                 650                 655

Ala Thr Asp Gly Ile Ser Asn Thr Phe Gly Val Thr Pro Asn Thr Leu
            660                 665                 670

Gly His Asp Leu Glu Ser Arg Lys Asp Thr Leu Val Asn Met Leu Asp
        675                 680                 685

Gly Tyr Met Lys Asn Asp Gly Met His Leu Asn Ile Asn Val Phe Asn
        690                 695                 700

Lys Asp Thr Leu Ile Asp Ala Gln Lys His Pro Glu Glu Tyr Pro Thr
705                 710                 715                 720

Leu Thr Val Arg Val Ser Gly Tyr Cys Val Tyr Phe Ala Asp Leu Thr
                725                 730                 735

Lys Glu Gln Gln Asp Asp Val Ile Ser Arg Thr Phe Phe Glu Ser Met
            740                 745                 750

<210> SEQ ID NO 73
<211> LENGTH: 804
<212> TYPE: DNA
<213> ORGANISM: Lactobacillus plantarum

<400> SEQUENCE: 73

```
atgccaacga tcacaactaa gacgcccgta aaaggactaa tatttaacat tcaaaaattt     60
agtatcaatg atggaccagg tattcgaaca gtagttttct ttaaagggtg cccgttacgc    120
tgcaagtggt gttctaatcc agaatcacaa tcaggtgagc aagaatcaat gtatgatgaa    180
cagaccgcca agcaaaccat cgtcggtgat tatatgacgg ttgatgatat tatgaaagtt    240
attctacaag ataaagactt ctatgaagag tctggcggtg gggtaacctt ctctggtggt    300
gaagttcttt ttcaagcttc ctttgcgatt gagcttgcta aggcagttaa agcagctggc    360
attaatttag cctgtgagac aactggttac gcacggccta aggttttcaa tgaattcatg    420
tcttatatgg acttcatgta ttatgactgt aaacaatggg acccagccca acatcgaatc    480
ggaacgggtg ccgataacgg ggtaatttta cgtaacttag caactgcagt gcaagctcat    540
caaaagatga tggttcggat tccggttatt ccaggtttta attatacatt gaatgacgcg    600
gatcattttg acaactatt taatcagatt ggcgtaaccg aagttgaatt attgccatt    660 caccagtttg ggttgaaaaa gtatcaagat ttgggccgaa aatatgcgct agttaatgtt    720
aaacagttac aagcggatga cttaattgat tatgctgaac atattcgtgc acatggtgtt    780
aaagtacggg tgaatgggtg gtaa                                           804
```

<210> SEQ ID NO 74
<211> LENGTH: 267
<212> TYPE: PRT
<213> ORGANISM: Lactobacillus plantarum

<400> SEQUENCE: 74

Met Pro Thr Ile Thr Thr Lys Thr Pro Val Lys Gly Leu Ile Phe Asn
1               5                   10                  15

Ile Gln Lys Phe Ser Ile Asn Asp Gly Pro Gly Ile Arg Thr Val Val
            20                  25                  30

Phe Phe Lys Gly Cys Pro Leu Arg Cys Lys Trp Cys Ser Asn Pro Glu
        35                  40                  45

Ser Gln Ser Gly Glu Gln Ser Met Tyr Asp Glu Gln Thr Ala Lys
    50                  55                  60

Gln Thr Ile Val Gly Asp Tyr Met Thr Val Asp Asp Ile Met Lys Val
65                  70                  75                  80

Ile Leu Gln Asp Lys Asp Phe Tyr Glu Glu Ser Gly Gly Val Thr
                85                  90                  95

Phe Ser Gly Gly Glu Val Leu Phe Gln Ala Ser Phe Ala Ile Glu Leu
            100                 105                 110

Ala Lys Ala Val Lys Ala Ala Gly Ile Asn Leu Ala Cys Glu Thr Thr
        115                 120                 125

Gly Tyr Ala Arg Pro Lys Val Phe Asn Glu Phe Met Ser Tyr Met Asp
    130                 135                 140

Phe Met Tyr Tyr Asp Cys Lys Gln Trp Asp Pro Ala Gln His Arg Ile
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
        195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265

<210> SEQ ID NO 75
<211> LENGTH: 822
<212> TYPE: DNA
<213> ORGANISM: Lactobacillus plantarum

<400> SEQUENCE: 75
atggaaaaca acaagttttc aacaacgcaa gcggcggcaa aggagccttt gataggctac      60
gttcactcca tcgaaacgtt tggctccgtt gacggaccag gtatccgtta cgtggcattc     120
cttcaaggat gccacatgcg ttgccaatac tgtcacaacc ctgatacttg aaactcaac      180 gttggcgatc aaatgacggc cgacgagatt ctcgaagacg cggctaaata ccgggctttc     240
tggggcaaga cgggtggcat cacagtcagt ggtggtgaat cactggtaca atcgacttc      300 atcttagact tattcgaaaa agccaaggcg atgaatatca gtacttgtct ggatacctct     360

```
ggacagcctt ttacccgaga caacctttc tttgacaagt tcgaacgtct aatgaaggtc      420
acggacattt cgttggtcga cattaagcac atcgattctg ccaaacacaa gcagttgacc      480
cagtatggga acgaaaatat cttggatatg attcagtaca tggcccaaca ccacgatgat      540
atgtggattc gtcacgtcct ggttccccaa cggactgatt acgatgaaga cttgaagaaa      600
ctcggcgatt acattgctaa aattccaaac gacgtcgttc aaaaagtcga agtattgccg      660
taccatactt tgggcgttaa aaatatcat gaaatgaaga tcaagtaccg gcttgaagga      720
atcgagtctc caacccaaga tcgggtggca aatgccgaaa agctactgca cactgctgat      780
tacaacgggt acaagacatg gatgccattg ccaaaacttt aa                        822
```

<210> SEQ ID NO 76
<211> LENGTH: 273
<212> TYPE: PRT
<213> ORGANISM: Lactobacillus plantarum

<400> SEQUENCE: 76

```
Met Glu Asn Lys Gln Val Ser Thr Thr Gln Ala Ala Lys Glu Pro
1               5                   10                  15

Leu Ile Gly Tyr Val His Ser Ile Glu Thr Phe Gly Ser Val Asp Gly
            20                  25                  30

Pro Gly Ile Arg Tyr Val Ala Phe Leu Gln Gly Cys His Met Arg Cys
        35                  40                  45

Gln Tyr Cys His Asn Pro Asp Thr Trp Lys Leu Asn Val Gly Asp Gln
    50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

Ile Ser Thr Cys Leu Asp Thr Ser Gly Gln Pro Phe Thr Arg Glu Gln
        115                 120                 125

Pro Phe Phe Asp Lys Phe Glu Arg Leu Met Lys Val Thr Asp Ile Ser
    130                 135                 140

Leu Val Asp Ile Lys His Ile Asp Ser Ala Lys His Lys Gln Leu Thr
145                 150                 155                 160

Gln Tyr Gly Asn Glu Asn Ile Leu Asp Met Ile Gln Tyr Met Ala Gln
                165                 170                 175

His His Asp Asp Met Trp Ile Arg His Val Leu Val Pro Gln Arg Thr
            180                 185                 190

Asp Tyr Asp Glu Asp Leu Lys Lys Leu Gly Asp Tyr Ile Ala Lys Ile
        195                 200                 205

Pro Asn Asp Val Val Gln Lys Val Glu Val Leu Pro Tyr His Thr Leu
    210                 215                 220

Gly Val Lys Lys Tyr His Glu Met Lys Ile Lys Tyr Arg Leu Glu Gly
225                 230                 235                 240

Ile Glu Ser Pro Thr Gln Asp Arg Val Ala Asn Ala Glu Lys Leu Leu
                245                 250                 255

His Thr Ala Asp Tyr Asn Gly Tyr Lys Thr Trp Met Pro Leu Pro Lys
            260                 265                 270

Leu
```

<210> SEQ ID NO 77

<211> LENGTH: 2364
<212> TYPE: DNA
<213> ORGANISM: Lactococcus lactis

<400> SEQUENCE: 77

```
atgaaaaccg aagttacgga aaatatcttt gaacaagctt gggatggttt taaaggaacc      60
aactggcgcg ataaagcaag cgttactcgc tttgtacaag aaaactacaa accatatgat     120
ggtgatgaaa gctttcttgc tgggccaaca gaacgtacac ttaaagtaaa gaaaattatt     180
gaagatacaa aaaatcacta cgaagaagta ggatttccct tcgatactga ccgcgtaacc     240
tctattgata aaatccctgc tggatatatc gatgctaatg ataaagaact tgaactcatc     300
tatgggatgc aaaatagcga acttttccgc ttgaatttca tgccaagagg tggacttcgt     360
gttgctgaaa agattttgac agaacacggt ctctcagttg acccaggctt gcatgatgtt     420
ttgtcacaaa caatgacttc tgtaaatgat ggaatctttc gtgcttatac ttcagcaatt     480
cgtaaagcac gtcatgctca tactgtaaca ggtttgccag atgcttactc tcgtggacgt     540
atcattggtg tctatgcacg tcttgccctt tacggtgctg attaccttat gaaggaaaaa     600
gcaaaagaat gggatgcaat cactgaaatt aacgaagaaa cattcgtct taaagaagaa     660
attaatatgc aataccaagc tttgcaagaa gttgtaaact ttggtgcttt atatggtctt     720
gatgtttcac gtccagctat gaacgtaaaa gaagcaatcc aatgggttaa catcgcttat     780
atggcagtat gtcgtgtcat aatggagct gcaacttcac ttgacgtgt tccaatcgtt     840
cttgatatct ttgcagaacg tgaccttgct cgtggaacat ttactgaaca agaaattcaa     900
gaatttgttg atgatttcgt tttgaagctt cgtacaatga aatttgcgcg tgcagctgct     960
tatgatgaac tttattctgg tgacccaaca ttcatcacaa catctatggc tggtatgggt    1020
aatgacggac gtcaccgtgt cactaaaatg gactaccgtt tcttgaacac acttgataca    1080
atcggaaatg ctccagaacc aaacttgaca gtcctttggg attctaaact tccttactca    1140
ttcaaacgtt attcaatgtc tatgagccac aagcattctt ctattcaata tgaaggtgtt    1200
gaaacaatgg ctaaagatgg atatggcgaa atgtcatgta tctcttgttg tgtctcacca    1260
cttgatccag aaaatgaaga aggacgtcat aacctccaat actttggtgc gcgtgtaaac    1320
gtcttgaaag caatgttgac tggtttgaac ggtggttatg atgacgttca taagagattat    1380
aaagtattcg acatcgaacc tgttcgtgac gaaattcttg actatgatac agttatggaa    1440
aactttgaca atctctcga ctggttgact gatacttatg ttgatgcaat gatatcatt    1500
cattacatga ctgataaata taactatgaa gcagttcaaa tggccttctt gcctactaaa    1560
gttcgtgcta acatgggatt tggtatctgt ggattcgcaa atacagttga ttcactttca    1620
gcaattaaat atgctaaagt taaacattg cgtgatgaaa atggctatat ctacgattac    1680
gaagtagaag gtgatttccc tcgttatggt gaagatgatg atcgtgctga tgatattgct    1740
aaacttgtca tgaaaatgta ccatgaaaaa ttagcttcac acaaacttta caaaatgct    1800
gaagctactg tttcactttt gacaattaca tctaacgttg cttactctaa acaaactggt    1860
aattctccag tacataaagg agtattcctc aatgaagatg gtacagtaaa taaatctaaa    1920
cttgaattct tctcaccagg tgctaaccca tctaataaag ctaagggtgg ttggttgcaa    1980
aatcttcgct cattggctaa gttggaattc aaagatgcaa atgatggtat ttcattgact    2040
actcaagttt cacctcgtgc acttggtaaa actcgtgatg aacaagtgga taacttggtt    2100
caaattcttg atggatactt cacaccaggt gctttgatta tggtactga atttgcaggt    2160
caacacgtta acttgaacgt aatggacctt aaagatgttt acgataaaat catgcgtggt    2220
```

```
gaagatgtta tcgttcgtat ctctggttac tgtgtcaata ctaaatacct cacaccagaa    2280
caaaaacaag aattaactga acgtgtcttc catgaagttc tttcaaacga tgatgaagaa    2340
gtaatgcata cttcaaacat ctaa                                          2364
```

<210> SEQ ID NO 78
<211> LENGTH: 787
<212> TYPE: PRT
<213> ORGANISM: Lactococcus lactis

<400> SEQUENCE: 78

```
Met Lys Thr Glu Val Thr Glu Asn Ile Phe Glu Gln Ala Trp Asp Gly
1               5                   10                  15

Phe Lys Gly Thr Asn Trp Arg Asp Lys Ala Ser Val Thr Arg Phe Val
            20                  25                  30

Gln Glu Asn Tyr Lys Pro Tyr Asp Gly Asp Glu Ser Phe Leu Ala Gly
        35                  40                  45

Pro Thr Glu Arg Thr Leu Lys Val Lys Lys Ile Ile Glu Asp Thr Lys
    50                  55                  60

Asn His Tyr Glu Glu Val Gly Phe Pro Phe Asp Thr Asp Arg Val Thr
65                  70                  75                  80

Ser Ile Asp Lys Ile Pro Ala Gly Tyr Ile Asp Ala Asn Asp Lys Glu
                85                  90                  95

Leu Glu Leu Ile Tyr Gly Met Gln Asn Ser Glu Leu Phe Arg Leu Asn
            100                 105                 110

Phe Met Pro Arg Gly Gly Leu Arg Val Ala Glu Lys Ile Leu Thr Glu
        115                 120                 125

His Gly Leu Ser Val Asp Pro Gly Leu His Asp Val Leu Ser Gln Thr
    130                 135                 140

Met Thr Ser Val Asn Asp Gly Ile Phe Arg Ala Tyr Thr Ser Ala Ile
145                 150                 155                 160

Arg Lys Ala Arg His Ala His Thr Val Thr Gly Leu Pro Asp Ala Tyr
                165                 170                 175

Ser Arg Gly Arg Ile Ile Gly Val Tyr Ala Arg Leu Ala Leu Tyr Gly
            180                 185                 190

Ala Asp Tyr Leu Met Lys Glu Lys Ala Lys Glu Trp Asp Ala Ile Thr
        195                 200                 205

Glu Ile Asn Glu Glu Asn Ile Arg Leu Lys Glu Glu Ile Asn Met Gln
    210                 215                 220

Tyr Gln Ala Leu Gln Glu Val Val Asn Phe Gly Ala Leu Tyr Gly Leu
225                 230                 235                 240

Asp Val Ser Arg Pro Ala Met Asn Val Lys Glu Ala Ile Gln Trp Val
                245                 250                 255

Asn Ile Ala Tyr Met Ala Val Cys Arg Val Ile Asn Gly Ala Ala Thr
            260                 265                 270

Ser Leu Gly Arg Val Pro Ile Val Leu Asp Ile Phe Ala Glu Arg Asp
        275                 280                 285

Leu Ala Arg Gly Thr Phe Thr Glu Gln Glu Ile Gln Glu Phe Val Asp
    290                 295                 300

Asp Phe Val Leu Lys Leu Arg Thr Met Lys Phe Ala Arg Ala Ala Ala
305                 310                 315                 320

Tyr Asp Glu Leu Tyr Ser Gly Asp Pro Thr Phe Ile Thr Thr Ser Met
                325                 330                 335

Ala Gly Met Gly Asn Asp Gly Arg His Arg Val Thr Lys Met Asp Tyr
```

-continued

```
                340             345             350
Arg Phe Leu Asn Thr Leu Asp Thr Ile Gly Asn Ala Pro Glu Pro Asn
            355                 360                 365

Leu Thr Val Leu Trp Asp Ser Lys Leu Pro Tyr Ser Phe Lys Arg Tyr
        370                 375                 380

Ser Met Ser Met Ser His Lys His Ser Ser Ile Gln Tyr Glu Gly Val
385                 390                 395                 400

Glu Thr Met Ala Lys Asp Gly Tyr Gly Glu Met Ser Cys Ile Ser Cys
                405                 410                 415

Cys Val Ser Pro Leu Asp Pro Glu Asn Glu Glu Gly Arg His Asn Leu
            420                 425                 430

Gln Tyr Phe Gly Ala Arg Val Asn Val Leu Lys Ala Met Leu Thr Gly
        435                 440                 445

Leu Asn Gly Gly Tyr Asp Asp Val His Lys Asp Tyr Lys Val Phe Asp
    450                 455                 460

Ile Glu Pro Val Arg Asp Glu Ile Leu Asp Tyr Asp Thr Val Met Glu
465                 470                 475                 480

Asn Phe Asp Lys Ser Leu Asp Trp Leu Thr Asp Thr Tyr Val Asp Ala
                485                 490                 495

Met Asn Ile Ile His Tyr Met Thr Asp Lys Tyr Asn Tyr Glu Ala Val
            500                 505                 510

Gln Met Ala Phe Leu Pro Thr Lys Val Arg Ala Asn Met Gly Phe Gly
        515                 520                 525

Ile Cys Gly Phe Ala Asn Thr Val Asp Ser Leu Ser Ala Ile Lys Tyr
    530                 535                 540

Ala Lys Val Lys Thr Leu Arg Asp Glu Asn Gly Tyr Ile Tyr Asp Tyr
545                 550                 555                 560

Glu Val Glu Gly Asp Phe Pro Arg Tyr Gly Asp Asp Arg Ala
                565                 570                 575

Asp Asp Ile Ala Lys Leu Val Met Lys Met Tyr His Glu Lys Leu Ala
            580                 585                 590

Ser His Lys Leu Tyr Lys Asn Ala Glu Ala Thr Val Ser Leu Leu Thr
        595                 600                 605

Ile Thr Ser Asn Val Ala Tyr Ser Lys Gln Thr Gly Asn Ser Pro Val
    610                 615                 620

His Lys Gly Val Phe Leu Asn Glu Asp Gly Thr Val Asn Lys Ser Lys
625                 630                 635                 640

Leu Glu Phe Phe Ser Pro Gly Ala Asn Pro Ser Asn Lys Ala Lys Gly
                645                 650                 655

Gly Trp Leu Gln Asn Leu Arg Ser Leu Ala Lys Leu Glu Phe Lys Asp
            660                 665                 670

Ala Asn Asp Gly Ile Ser Leu Thr Thr Gln Val Ser Pro Arg Ala Leu
        675                 680                 685

Gly Lys Thr Arg Asp Glu Gln Val Asp Asn Leu Val Gln Ile Leu Asp
    690                 695                 700

Gly Tyr Phe Thr Pro Gly Ala Leu Ile Asn Gly Thr Glu Phe Ala Gly
705                 710                 715                 720

Gln His Val Asn Leu Asn Val Met Asp Leu Lys Asp Val Tyr Asp Lys
                725                 730                 735

Ile Met Arg Gly Glu Asp Val Ile Val Arg Ile Ser Gly Tyr Cys Val
            740                 745                 750

Asn Thr Lys Tyr Leu Thr Pro Glu Gln Lys Gln Glu Leu Thr Glu Arg
        755                 760                 765
```

Val Phe His Glu Val Leu Ser Asn Asp Asp Glu Val Met His Thr
    770                 775                 780

Ser Asn Ile
785

<210> SEQ ID NO 79
<211> LENGTH: 795
<212> TYPE: DNA
<213> ORGANISM: Lactococcus lactis

<400> SEQUENCE: 79
atgatgtcag agaatataga tgaacttaaa aaagttactg gactgattca ttcaactgaa      60
tcttttggtt ctgttgatgg ccctggggtc cgttttatta ttttcatgca aggctgtcgg     120
atgcgttgca atattgtca caaccctgat acttgggcat aaagtcaga taaagcgaca       180 gagcgtaccg tagaagatgt catggatgag gcacttcgtt ttagaggttt ttggggagag    240
aaaggtggaa ttaccgtttc tggtggtgag gcgctccttc aaattgactt tgtattagct    300
cttttcaaat atgcaaaatc tctcggtatt catacaacac ttgatacagc ggctcaacca    360
tatttgactg ataaatatgt aaccgaaaaa attgatgagt actagatta taccgactta     420 gtattattag acattaaaga aataaatcca gaacgacaca agaattgac agctaataaa     480 aacgataata tttagctttt tgcacagtat ttatcagacc gtggtaatgc aatgtgggtt    540
cgtcacgttc ttgttcctgg tgaaagtgat tttgatgaag atttagttca attaggtgaa    600
tttgtaaaaa ctttaaaaaa tgtcttgaaa tttgaaattt taccctacca tacaatgggt    660
gaatttaaat ggcgtgaatt aggttggaaa tatccgcttg aaggtgtgaa acctccaaca    720
aaagatcgtg ttcataatgc taaagaaatc atgaatacag aatcttatca agattactta    780
gaacgtataa gataa                                                     795

<210> SEQ ID NO 80
<211> LENGTH: 264
<212> TYPE: PRT
<213> ORGANISM: Lactococcus lactis

<400> SEQUENCE: 80

Met Met Ser Glu Asn Ile Asp Glu Leu Lys Lys Val Thr Gly Leu Ile
1               5                   10                  15

His Ser Thr Glu Ser Phe Gly Ser Val Asp Gly Pro Gly Val Arg Phe
            20                  25                  30

Ile Ile Phe Met Gln Gly Cys Arg Met Arg Cys Lys Tyr Cys His Asn
        35                  40                  45

Pro Asp Thr Trp Ala Leu Lys Ser Asp Lys Ala Thr Glu Arg Thr Val
    50                  55                  60

Glu Asp Val Met Asp Glu Ala Leu Arg Phe Arg Gly Phe Trp Gly Glu
65                  70                  75                  80

Lys Gly Gly Ile Thr Val Ser Gly Gly Glu Ala Leu Leu Gln Ile Asp
                85                  90                  95

Phe Val Leu Ala Leu Phe Lys Tyr Ala Lys Ser Leu Gly Ile His Thr
            100                 105                 110

Thr Leu Asp Thr Ala Ala Gln Pro Tyr Leu Thr Asp Lys Tyr Val Thr
        115                 120                 125

Glu Lys Ile Asp Glu Leu Leu Asp Tyr Thr Asp Leu Val Leu Leu Asp
    130                 135                 140

Ile Lys Glu Ile Asn Pro Glu Arg His Lys Glu Leu Thr Ala Asn Lys

```
                145            150             155             160
Asn Asp Asn Ile Leu Ala Phe Ala Gln Tyr Leu Ser Asp Arg Gly Asn
                    165                 170                 175

Ala Met Trp Val Arg His Val Leu Val Pro Gly Glu Ser Asp Phe Asp
                    180                 185                 190

Glu Asp Leu Val Gln Leu Gly Glu Phe Val Lys Thr Leu Lys Asn Val
                    195                 200                 205

Leu Lys Phe Glu Ile Leu Pro Tyr His Thr Met Gly Glu Phe Lys Trp
        210                 215                 220

Arg Glu Leu Gly Trp Lys Tyr Pro Leu Glu Gly Val Lys Pro Pro Thr
225                 230                 235                 240

Lys Asp Arg Val His Asn Ala Lys Glu Ile Met Asn Thr Glu Ser Tyr
                    245                 250                 255

Gln Asp Tyr Leu Glu Arg Ile Arg
                260

<210> SEQ ID NO 81
<211> LENGTH: 2310
<212> TYPE: DNA
<213> ORGANISM: Streptococcus thermophilus

<400> SEQUENCE: 81
atggcaacgg ttaaaactaa cacagatgtt tttgaaaaag cgtgggaagg ctttaaagga      60
actgactgga agaaaaaagc aagtgtgtct cgcttcgtac aagcaaacta cacaccatat    120
gatggtgatg aaagcttcct tgcaggacca actgaacgct cacttaaaat caaaaaaatc    180
attgaagaaa ctaaagctca ctacgaagaa actcgtttcc caatggatac tcgtccgaca    240
tcaatcgcag atattcctgc cggctatatt tcaaaagacg acgaactaat ctacggtatt    300
caaaatgatg agttattcaa attgaatttc atgccaaaag gcggaattcg tatggcagaa    360
acagctctca aggaacatgg ctatgaacct gatccagctg ttcacgaaat ttttacaaaa    420
catgtaacta cagtaaatga cggtatcttc cgtgcttata catcaaatat ccgtcgtgca    480
cgtcacgcac acactataac tggacttcca gatgcttact ctcgtggacg tatcatcggt    540
gtttatgctc gccttgctct ttacggtgct gacttcttga tgcaagaaaa agtaaacgac    600
tggaactcta tcgaagaaat caacgaagaa actattcgtc ttcgtgaaga agttaacctt    660
caataccaag cacttcaaga tgttgttcgc cttggtgacc tttacggtgt agatgttcgt    720
cgtccagcct cgatactaa agaagctatc caatggacaa acattgcttt tatggctgta    780
tgtcgtgtta tcaatggtgc ggctacttca cttggtcgtg tgccaatcgt ccttgacata    840
tatgcagaac gtgaccttgc tcgtggtact acactgaat cagaaatcca agaattcgtt    900
gatgattttg tcttgaaact tcgtactgta aaattcgcac gtacaaaagc ttacgacgaa    960
ctttactcag gtgacccaac attcatcaca acttctatgg ctggtatggg tgctgacgga   1020
cgtcaccgtg ttactaaaat ggactaccgt ttcttgaaca cacttgataa tattggtaat   1080
gctccagaac caaacttgac agttctttgg tctgacaaat tgccttactc attccgtcgc   1140
tactgtatgc acatgagtca caagcactct tctattcaat acgaaggtgt gactactatg   1200
gctaaagacg gatacggtga atgagctgt atctcatgtt gtgtatcacc acttgaccca   1260
gaaaacgaag aacaacgcca caacatccaa tacttcggtg ctcgtgttaa cgtacttaaa   1320
gcccttctta ctggttttga acggtggtac gacgatgttc ataaagacta caaagtattt   1380
gacatcgatc cagtccgtga tgaagttctt gactttgaca ctgttaaagc taacttcgaa   1440
```

-continued

```
aaatctcttg actggttgac tgacacttat gtagatgccc ttaacatcat ccactacatg    1500
actgataagt acaactacga agctgttcaa atggccttct tgccaactaa caacgtgct     1560 aacatgggat tcggtatctg tggtttcgca atactgttg atacattgtc agctatcaag     1620
tacgctacag ttaaaccaat ccgtgacgaa gatggctaca tctacgacta cgaaacaatc    1680
ggtgaatacc cacgttgggg tgaagatgac ccacgttcaa acgaattggc agaatggttg    1740
attgaagctt acactactcg tcttcgtagc cataaactct acaaagatgc agaagctaca    1800
gtttcacttc ttacaatcac ttcgaacgtt gcttactcta aacaaactgg taactctcca    1860
gttcacaaag gggtatacct caacgaagat ggttcagtga acttgtctaa attggaattc    1920
ttctcaccag gtgctaaccc atctaacaaa gctaaaggtg gatggttgca aaacttgaac    1980
tcacttgcaa gccttgactt cggttatgca gctgacggta tctcacttac tactcaagta    2040
tcacctcgtg cccttggtaa gactcgcgac gaacaagttg ataacctcgt aactatcctt    2100
gacggatact tcgaaaacgg tggacaacac cttaacttga acgttatgga cttgtcagct    2160
gtttacaaaa agatcatgag cggtgaagat gttatcgtac gtatctctgg atactgtgta    2220
aacactaaat acctcactcc agaacaaaaa actgaattga cacaacgtgt cttccacgaa    2280
gttctttcaa cggacgatgc tatgggataa                                     2310
```

<210> SEQ ID NO 82
<211> LENGTH: 769
<212> TYPE: PRT
<213> ORGANISM: Streptococcus thermophilus

<400> SEQUENCE: 82

```
Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Glu Glu Thr
    50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175

Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Glu Val Asn Leu Gln Tyr Gln Ala
    210                 215                 220
```

```
Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
            245                 250                 255

Phe Met Ala Val Cys Arg Val Ile Asn Gly Ala Ala Thr Ser Leu Gly
        260                 265                 270

Arg Val Pro Ile Val Leu Asp Ile Tyr Ala Glu Arg Asp Leu Ala Arg
    275                 280                 285

Gly Thr Tyr Thr Glu Ser Glu Ile Gln Glu Phe Val Asp Asp Phe Val
290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
    370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Val Ser
                405                 410                 415

Pro Leu Asp Pro Glu Asn Glu Glu Gln Arg His Asn Ile Gln Tyr Phe
            420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
    450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
    530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Pro Arg Ser Asn Glu Leu
                565                 570                 575

Ala Glu Trp Leu Ile Glu Ala Tyr Thr Thr Arg Leu Arg Ser His Lys
            580                 585                 590

Leu Tyr Lys Asp Ala Glu Ala Thr Val Ser Leu Leu Thr Ile Thr Ser
        595                 600                 605

Asn Val Ala Tyr Ser Lys Gln Thr Gly Asn Ser Pro Val His Lys Gly
    610                 615                 620

Val Tyr Leu Asn Glu Asp Gly Ser Val Asn Leu Ser Lys Leu Glu Phe
625                 630                 635                 640
```

```
Phe Ser Pro Gly Ala Asn Pro Ser Asn Lys Ala Lys Gly Gly Trp Leu
            645                 650                 655

Gln Asn Leu Asn Ser Leu Ala Ser Leu Asp Phe Gly Tyr Ala Ala Asp
        660                 665                 670

Gly Ile Ser Leu Thr Thr Gln Val Ser Pro Arg Ala Leu Gly Lys Thr
            675                 680                 685

Arg Asp Glu Gln Val Asp Asn Leu Val Thr Ile Leu Asp Gly Tyr Phe
    690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly

<210> SEQ ID NO 83
<211> LENGTH: 801
<212> TYPE: DNA
<213> ORGANISM: Streptococcus thermophilus

<400> SEQUENCE: 83
atggcagaaa ttgattacag tcaggtgact ggacttgttc attcaaccga aagtttcgga      60
tccgtagatg gtcctggtat ccgttttatt gtgtttatgc aaggctgtaa gctgcgttgc     120
caatattgtc ataacccaga tacttgggcc atgaagtcaa ataaggctgt gaacgtaca     180 gttgaagatg tcttagaaga ggctcttcgc ttccgtcatt tctggggtga gcatggtgga     240
atcactgtat caggtggtga agccatgctt cagattgatt ttgtcactgc cctctttaca     300
gaggctaaga agtagggat tcactgtacg cttgatacgt gtggcttgtc ttatcgtaat     360
actccagagt atcatgaagt tgtcgacaaa cttttggctg taactgactt ggttctactg     420
gatatcaaag agattgaccc cgaacaacac aagtttgtga cccgtcaacc taataagaat     480
atcttggaat ttgctcaata tctgtctgat aaacaagttc cggtctggat tcgtcatgtc     540
ttggtacctg gtttgacaga ttttgacgaa cacttggtta agctcggcga gtttgtaaag     600
accttgaaaa atgtcgataa atttgaaatt cttccatatc atacgatggg ggaattcaag     660
tggcgtgaac ttggcatccc ttatccattg gaaggtgtca accaccaac tgcagatcgt     720 gttaaaaatg ctaaggctct tatgcatacg gaaacttatc aagagtataa gaatcgtatc     780
ggggttaaaa ccttggatta a                                                801

<210> SEQ ID NO 84
<211> LENGTH: 266
<212> TYPE: PRT
<213> ORGANISM: Streptococcus thermophilus

<400> SEQUENCE: 84

Met Ala Glu Ile Asp Tyr Ser Gln Val Thr Gly Leu Val His Ser Thr
1               5                   10                  15

Glu Ser Phe Gly Ser Val Asp Gly Pro Gly Ile Arg Phe Ile Val Phe
            20                  25                  30

Met Gln Gly Cys Lys Leu Arg Cys Gln Tyr Cys His Asn Pro Asp Thr
        35                  40                  45
```

```
Trp Ala Met Lys Ser Asn Lys Ala Val Glu Arg Thr Val Glu Asp Val
     50                  55                  60
Leu Glu Glu Ala Leu Arg Phe Arg His Phe Trp Gly Glu His Gly Gly
 65                  70                  75                  80
Ile Thr Val Ser Gly Gly Glu Ala Met Leu Gln Ile Asp Phe Val Thr
                 85                  90                  95
Ala Leu Phe Thr Glu Ala Lys Lys Leu Gly Ile His Cys Thr Leu Asp
                100                 105                 110
Thr Cys Gly Leu Ser Tyr Arg Asn Thr Pro Glu Tyr His Glu Val Val
                115                 120                 125
Asp Lys Leu Leu Ala Val Thr Asp Leu Val Leu Leu Asp Ile Lys Glu
    130                 135                 140
Ile Asp Pro Glu Gln His Lys Phe Val Thr Arg Gln Pro Asn Lys Asn
145                 150                 155                 160
Ile Leu Glu Phe Ala Gln Tyr Leu Ser Asp Lys Gln Val Pro Val Trp
                165                 170                 175
Ile Arg His Val Leu Val Pro Gly Leu Thr Asp Phe Asp Glu His Leu
                180                 185                 190
Val Lys Leu Gly Glu Phe Val Lys Thr Leu Lys Asn Val Asp Lys Phe
    195                 200                 205
Glu Ile Leu Pro Tyr His Thr Met Gly Glu Phe Lys Trp Arg Glu Leu
210                 215                 220
Gly Ile Pro Tyr Pro Leu Glu Gly Val Lys Pro Pro Thr Ala Asp Arg
225                 230                 235                 240
Val Lys Asn Ala Lys Ala Leu Met His Thr Glu Thr Tyr Gln Glu Tyr
                245                 250                 255
Lys Asn Arg Ile Gly Val Lys Thr Leu Asp
                260                 265

<210> SEQ ID NO 85
<211> LENGTH: 1716
<212> TYPE: DNA
<213> ORGANISM: Bacillus subtilis

<400> SEQUENCE: 85
atgttgacaa agcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt taactggaaa accgggagtc     240
gtgttagtca catcaggacc gggtgcctct aacttggcaa caggcctgct gacagcgaac     300
actgaaggag accctgtcgt tgcgcttgct ggaaacgtga ccgtgcaga tcgtttaaaa      360
cggacacatc aatctttgga taatgcggcg ctattccagc cgattacaaa atacagtgta     420
gaagttcaag atgtaaaaaa tataccggaa gctgttacaa atgcatttag gatagcgtca     480
gcagggcagg ctggggccgc ttttgtgagc tttccgcaag atgttgtgaa tgaagtcaca     540
aatacgaaaa acgtgcgtgc tgttgcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc ttttgaaaaa ggttcagctt     720
ccatttgttg aaacatatca agctgccggt acccttttta gagatttaga ggatcaatat     780
tttgccgta tcggtttgtt ccgcaaccag cctggcgatt tactgctaga gcaggcagat     840
gttgttctga cgatcggcta tgacccgatt gaatatgatc cgaaattctg gaatatcaat     900
```

-continued

```
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgt tgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716
```

<210> SEQ ID NO 86
<211> LENGTH: 571
<212> TYPE: PRT
<213> ORGANISM: Bacillus subtilis

<400> SEQUENCE: 86

```
Met Leu Thr Lys Ala Thr Lys Glu Gln Lys Ser Leu Val Lys Asn Arg
1               5                   10                  15
Gly Ala Glu Leu Val Val Asp Cys Leu Val Glu Gln Gly Val Thr His
            20                  25                  30
Val Phe Gly Ile Pro Gly Ala Lys Ile Asp Ala Val Phe Asp Ala Leu
        35                  40                  45
Gln Asp Lys Gly Pro Glu Ile Ile Val Ala Arg His Glu Gln Asn Ala
    50                  55                  60
Ala Phe Met Ala Gln Ala Val Gly Arg Leu Thr Gly Lys Pro Gly Val
65                  70                  75                  80
Val Leu Val Thr Ser Gly Pro Gly Ala Ser Asn Leu Ala Thr Gly Leu
                85                  90                  95
Leu Thr Ala Asn Thr Glu Gly Asp Pro Val Val Ala Leu Ala Gly Asn
            100                 105                 110
Val Ile Arg Ala Asp Arg Leu Lys Arg Thr His Gln Ser Leu Asp Asn
        115                 120                 125
Ala Ala Leu Phe Gln Pro Ile Thr Lys Tyr Ser Val Glu Val Gln Asp
    130                 135                 140
Val Lys Asn Ile Pro Glu Ala Val Thr Asn Ala Phe Arg Ile Ala Ser
145                 150                 155                 160
Ala Gly Gln Ala Gly Ala Ala Phe Val Ser Phe Pro Gln Asp Val Val
                165                 170                 175
Asn Glu Val Thr Asn Thr Lys Asn Val Arg Ala Val Ala Ala Pro Lys
            180                 185                 190
Leu Gly Pro Ala Ala Asp Asp Ala Ile Ser Ala Ala Ile Ala Lys Ile
        195                 200                 205
Gln Thr Ala Lys Leu Pro Val Val Leu Val Gly Met Lys Gly Gly Arg
    210                 215                 220
```

```
Pro Glu Ala Ile Lys Ala Val Arg Lys Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Gly Asp Arg Thr
290                 295                 300

Ile Ile His Leu Asp Glu Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 87
<211> LENGTH: 1716
<212> TYPE: DNA
<213> ORGANISM: artificial sequence
<220> FEATURE:
<223> OTHER INFORMATION: codon optimized coding region for expression in
      Lactobacillus plantarum

<400> SEQUENCE: 87
atgttgacca aggctaccaa agaacaaaag agtttagtca aaaccgtgg tgctgaatta      60
```

```
gtcgtggatt gtttggttga acaaggtgtg acgcatgttt ttggtattcc aggagctaaa    120
attgatgccg tttttgatgc gttacaagat aagggtccag aaattattgt ggcacgtcat    180
gaacaaaatg cagcgtttat ggctcaagca gttggtcggt tgactggcaa accaggtgtg    240
gttttagtga cgtcaggtcc aggtgcgagt aatttagcga ctggcttgtt aacggcgaat    300
actgaaggtg atccagtcgt tgctttggca ggcaatgtca ttcgtgccga tcgtttaaag    360
cggacccatc agagtttgga taatgcagcc ttgtttcaac cgattacgaa atattccagtt   420 gaagtccaag atgtcaagaa tattccagaa gcggttacga atgcgtttcg tattgcatca    480
gctggccaag caggcgcagc gtttgtgagt tttccacaag atgtcgtgaa tgaagttact    540
aacaccaaga atgtccgtgc agtcgcagct ccaaagttag gtccagcagc tgacgatgcc    600
attagtgcag ctattgccaa aattcagact gcaaaattgc cggttgtgtt agttggcatg    660
aaaggtggtc gtccagaagc cattaaagcg gttcgtaagt tattgaaaaa ggttcaatta    720
ccatttgttg aaacgtatca agctgcaggt acgttaagtc gtgacttaga agatcaatat    780
tttggtcgga ttggtttgtt tcgtaatcaa ccaggtgatt tgttattaga acaagctgat    840
gtggttttaa ctattggcta tgatccgatt gaatatgatc caaagttttg gaatattaat    900
ggtgatcgta ccatcattca tttggatgaa atcattgctg atattgatca cgcttatcaa    960
ccggatttgg aattaattgg tgacattcca agtacgatta atcacattga acatgatgct    1020
gtgaaggttg agtttgcgga acgggaacag aaaattttat cagatttgaa gcaatatatg    1080
catgaaggtg aacaagtgcc agcagattgg aagtcagatc gggcccatcc attagaaatt    1140
gttaaagaat tacggaatgc agtggacgat catgtgaccg tgacttgtga tattggtagt    1200
catgctattt ggatgagtcg ttactttcgg tcatatgaac cgttaacttt aatgatttca    1260
aacggtatgc aaactttagg tgttgccttg ccatgggcca ttggtgcgtc attggtcaaa    1320
ccaggtgaaa aggtcgtgtc agtcagtgga gatggtggct tcttattcag tgctatggaa    1380
ttagaaaccg ctgtgcggtt gaaggcaccg attgtgcata ttgtgtggaa cgatagtact    1440
tatgatatgg tcgcatttca acagttgaag aaatataatc gtacctcagc agtggatttt    1500
ggtaatatcg atattgtcaa gtatgccgaa agttttggtg ccaccggttt gcgtgtcgaa    1560
tcaccagatc aattagctga tgtcttgcgt caaggtatga atgcggaagg cccagttatt    1620
attgatgtgc cagttgatta cagtgataac attaatttag ctagtgataa gttgccgaaa    1680
gaatttggtg aattaatgaa gacgaaagcg ttataa                              1716

<210> SEQ ID NO 88
<211> LENGTH: 1680
<212> TYPE: DNA
<213> ORGANISM: Klebsiella pneumoniae

<400> SEQUENCE: 88
atggacaaac agtatccggt acgccagtgg gcgcacggcg ccgatctcgt cgtcagtcag     60
ctggaagctc agggagtacg ccaggtgttc ggcatccccg gcgccaaaat cgacaaggtc    120
tttgattcac tgctggattc ctccattcgc attattccgg tacgccacga agccaacgcc    180
gcatttatgg ccgccgccgt cggacgcatt accggcaaag cgggcgtggc gctggtcacc    240
tccggtccgg gctgttccaa cctgatcacc ggcatggcca ccgcgaacag cgaaggcgac    300
ccggtggtgg ccctgggcgg cgcggtaaaa cgcggccgata agcgaagca ggtccaccag    360 agtatggata cggtggcgat gttcagcccg gtcaccaaat acgccatcga ggtgacggcg    420
ccggatgcgc tggcggaagt ggtctccaac gccttccgcg ccgccgagca gggccggccg    480
```

-continued

```
ggcagcgcgt tcgttagcct gccgcaggat gtggtcgatg gcccggtcag cggcaaagtg      540
ctgccggcca gcggggcccc gcagatgggc gccgcgccgg atgatgccat cgaccaggtg      600
gcgaagctta tcgcccaggc gaagaacccg atcttcctgc tcggcctgat ggccagccag      660
ccggaaaaca gcaaggcgct cgccgtttg ctggagacca gccatattcc agtcaccagc       720
acctatcagg ccgccggagc ggtgaatcag gataacttct ctcgcttcgc cggccgggtt      780
gggctgttta caaccaggc cggggaccgt ctgctgcagc tcgccgacct ggtgatctgc       840
atcggctaca gcccggtgga atacgaaccg gcgatgtgga acagcggcaa cgcgacgctg      900
gtgcacatcg acgtgctgcc cgcctatgaa gagcgcaact acaccccgga tgtcgagctg      960
gtgggcgata tcgccggcac tctcaacaag ctggcgcaaa atatcgatca tcggctggtg     1020
ctctccccgc aggcggcgga gatcctccgc gaccgccagc accagcgcga gctgctggac     1080
cgccgcggcg cgcagctcaa ccagtttgcc ctgcatcccc tgcgcatcgt tcgcgccatg     1140
caggatatcg tcaacagcga cgtcacgttg accgtggaca tgggcagctt ccatatctgg     1200
attgcccgct acctgtacac gttccgcgcc cgtcaggtga tgatctccaa cggccagcag     1260
accatgggcg tcgccctgcc ctgggctatc ggcgcctggc tggtcaatcc tgagcgcaaa     1320
gtggtctccg tctccggcga cggcggcttc ctgcagtcga gcatggagct ggagaccgcc     1380
gtccgcctga agccaacgt gctgcatctt atctgggtcg ataacggcta caacatggtc      1440
gctatccagg aagagaaaaa atatcagcgc ctgtccggcg tcgagtttgg gccgatggat     1500
tttaaagcct atgccgaatc cttcggcgcg aaagggtttg ccgtggaaag cgccgaggcg     1560
ctggagccga ccctgcgcgc ggcgatggac gtcgacggcc cggcggtagt ggccatcccg     1620
gtggattatc gcgataaccc gctgctgatg ggccagctgc atctgagtca gattctgtaa     1680
```

<210> SEQ ID NO 89
<211> LENGTH: 559
<212> TYPE: PRT
<213> ORGANISM: Klebsiella pneumoniae

<400> SEQUENCE: 89

```
Met Asp Lys Gln Tyr Pro Val Arg Gln Trp Ala His Gly Ala Asp Leu
1               5                  10                   15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160
```

Gly Ser Ala Phe Val Ser Leu Pro Gln Asp Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 90
<211> LENGTH: 1665
<212> TYPE: DNA

<213> ORGANISM: Lactococcus lactis

<400> SEQUENCE: 90

```
atgtctgaga acaatttggg gcgaacttg gttgtcgata gtttgattaa ccataaagtg      60
aagtatgtat ttgggattcc aggagcaaaa attgaccggg tttttgattt attagaaaat     120
gaagaaggcc ctcaaatggt cgtgactcgt catgagcaag agctgctttt catggctcaa     180
gctgtcggtc gtttaactgg cgaacctggt gtagtagttg ttacgagtgg gcctggtgta     240
tcaaaccttg cgactccgct tttgaccgcg acatcagaag gtgatgctat tttggctatc     300
ggtggacaag ttaaacgaag tgaccgtctt aaacgtgcgc accaatcaat ggataatgct     360
ggaatgatgc aatcagcaac aaaatattca gcagaagttc ttgaccctaa tacactttct     420
gaatcaattg ccaacgctta tcgtattgca aaatcaggac atccaggtgc aactttctta     480
tcaatccccc aagatgtaac ggatgccgaa gtatcaatca aagccattca accactttca     540
gaccctaaaa tggggaatgc ctctattgat gacattaatt atttagcaca agcaattaaa     600
aatgctgtat tgccagtaat tttggttgga gctggtgctt cagatgctaa agtcgcttca     660
tccttgcgta atctattgac tcatgttaat attcctgtcg ttgaaacatt ccaaggtgca     720
ggggttattt cacatgattt agaacatact ttttatggac gtatcggtct tttccgcaat     780
caaccaggcg atatgcttct gaaacgttct gaccttgtta ttgctgttgg ttatgaccca     840
attgaatatg aagctcgtaa ctggaatgca gaaattgata tcgaattat cgttattgat     900
aatgccattg ctgaaattga tacttactac caaccagagc gtgaattaat tggtgatatc     960
gcagcaacat tggataatct tttaccagct gttcgtggct acaaaattcc aaaaggaaca    1020
aaagattatc tcgatggcct tcatgaagtt gctgagcaac acgaatttga tactgaaaat    1080
actgaagaag gtagaatgca ccctcttgat ttggtcagca ctttccaaga atcgtcaag    1140
gatgatgaaa cagtaaccgt tgacgtaggt tcactctaca tttggatggc acgtcatttc    1200
aaatcatacg aaccacgtca tctcctcttc tcaaacggaa tgcaaacact cggagttgca    1260
cttccttggg caattacagc cgcattgttg cgcccaggta aaaagtttta ttcacactct    1320
ggtgatggag gcttcctttt cacagggcaa gaattggaaa cagctgtacg tttgaatctt    1380
ccaatcgttc aaattatctg gaatgacggc cattatgata tggttaaatt ccaagaagaa    1440
atgaaatatg gtcgttcagc agccgttgat tttggctatg ttgattacgt aaaatatgct    1500
gaagcaatga gagcaaaagg ttaccgtgca cacagcaaag aagaacttgc tgaaattctc    1560
aaatcaatcc cagatactac tggaccggtg gtaattgacg ttcctttgga ctattctgat    1620
aacattaaat tagcagaaaa attattgcct gaagagtttt attga                    1665
```

<210> SEQ ID NO 91
<211> LENGTH: 554
<212> TYPE: PRT
<213> ORGANISM: Lactococcus lactis

<400> SEQUENCE: 91

```
Met Ser Glu Lys Gln Phe Gly Ala Asn Leu Val Val Asp Ser Leu Ile
 1               5                  10                  15

Asn His Lys Val Lys Tyr Val Phe Gly Ile Pro Gly Ala Lys Ile Asp
             20                  25                  30

Arg Val Phe Asp Leu Leu Glu Asn Glu Glu Gly Pro Gln Met Val Val
         35                  40                  45

Thr Arg His Glu Gln Gly Ala Ala Phe Met Ala Gln Ala Val Gly Arg
     50                  55                  60
```

-continued

```
Leu Thr Gly Glu Pro Gly Val Val Val Thr Ser Gly Pro Gly Val
 65                  70                  75                  80

Ser Asn Leu Ala Thr Pro Leu Leu Thr Ala Thr Ser Glu Gly Asp Ala
                 85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Ala Lys Val Ala Ser Ser Leu Arg Asn
210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Arg Ile Gly
                245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
        275                 280                 285

Asn Ala Glu Ile Asp Ser Arg Ile Ile Val Ile Asp Asn Ala Ile Ala
290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
        355                 360                 365

Leu Asp Leu Val Ser Thr Phe Gln Glu Ile Val Lys Asp Asp Glu Thr
370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
            420                 425                 430

Gly Lys Lys Val Tyr Ser His Ser Gly Asp Gly Gly Phe Leu Phe Thr
        435                 440                 445

Gly Gln Glu Leu Glu Thr Ala Val Arg Leu Asn Leu Pro Ile Val Gln
450                 455                 460

Ile Ile Trp Asn Asp Gly His Tyr Asp Met Val Lys Phe Gln Glu Glu
465                 470                 475                 480
```

-continued

```
Met Lys Tyr Gly Arg Ser Ala Ala Val Asp Phe Gly Tyr Val Asp Tyr
            485                 490                 495

Val Lys Tyr Ala Glu Ala Met Arg Ala Lys Gly Tyr Arg Ala His Ser
        500                 505                 510

Lys Glu Glu Leu Ala Glu Ile Leu Lys Ser Ile Pro Asp Thr Thr Gly
    515                 520                 525

Pro Val Val Ile Asp Val Pro Leu Asp Tyr Ser Asp Asn Ile Lys Leu
530                 535                 540

Ala Glu Lys Leu Leu Pro Glu Glu Phe Tyr
545                 550

<210> SEQ ID NO 92
<211> LENGTH: 1665
<212> TYPE: DNA
<213> ORGANISM: Staphylococcus aureus
<220> FEATURE:
<221> NAME/KEY: CDS
<222> LOCATION: (1)..(1665)

<400> SEQUENCE: 92 atg act gat aaa aag tac act gca gcc gat atg gtt att gat act ttg        48
Met Thr Asp Lys Lys Tyr Thr Ala Ala Asp Met Val Ile Asp Thr Leu
1               5                   10                  15 aaa aat aat ggg gta gaa tat gtt ttt ggt att ccg ggt gca aag ata        96
Lys Asn Asn Gly Val Glu Tyr Val Phe Gly Ile Pro Gly Ala Lys Ile
            20                  25                  30 gac tat cta ttt aat gct tta att gat gat ggt cct gaa ctt att gtc       144
Asp Tyr Leu Phe Asn Ala Leu Ile Asp Asp Gly Pro Glu Leu Ile Val
        35                  40                  45 act cgt cat gaa caa aat gct gca atg atg gca caa ggt att gga aga       192
Thr Arg His Glu Gln Asn Ala Ala Met Met Ala Gln Gly Ile Gly Arg
    50                  55                  60 tta aca ggt aaa ccg ggt gta gta ctt gtt aca agt ggc cct ggt gta       240
Leu Thr Gly Lys Pro Gly Val Val Leu Val Thr Ser Gly Pro Gly Val
65                  70                  75                  80 agt aat tta acg act gga cta tta aca gct aca tct gaa ggg gat cct       288
Ser Asn Leu Thr Thr Gly Leu Leu Thr Ala Thr Ser Glu Gly Asp Pro
                85                  90                  95 gta tta gcg tta ggt ggc caa gtg aaa cgt aat gat tta tta cga tta       336
Val Leu Ala Leu Gly Gly Gln Val Lys Arg Asn Asp Leu Leu Arg Leu
            100                 105                 110 acg cat caa agt att gat aat gct gcg cta tta aaa tat tca tca aaa       384
Thr His Gln Ser Ile Asp Asn Ala Ala Leu Leu Lys Tyr Ser Ser Lys
        115                 120                 125 tac agt gaa gaa gta caa gat cct gaa tca tta tca gaa gtt atg aca       432
Tyr Ser Glu Glu Val Gln Asp Pro Glu Ser Leu Ser Glu Val Met Thr
    130                 135                 140 aat gca att cga att gct act tca gga aaa aat ggc gca agt ttt att       480
Asn Ala Ile Arg Ile Ala Thr Ser Gly Lys Asn Gly Ala Ser Phe Ile
145                 150                 155                 160 agt att ccg caa gac gtt att tct tca cca gtt gaa tct aaa gct ata       528
Ser Ile Pro Gln Asp Val Ile Ser Ser Pro Val Glu Ser Lys Ala Ile
                165                 170                 175 tca ctt tgc caa aaa cca aat tta gga gta ccg agt gaa caa gat att       576
Ser Leu Cys Gln Lys Pro Asn Leu Gly Val Pro Ser Glu Gln Asp Ile
            180                 185                 190 aat gat gtc att gaa gcg att aaa aat gca tca ttt cct gtt tta tta       624
Asn Asp Val Ile Glu Ala Ile Lys Asn Ala Ser Phe Pro Val Leu Leu
        195                 200                 205 gct ggt atg aga agt tca agt gca gaa gaa aca aat gcc att cgc aaa       672
```

| | | | | | | | | | | | | | |
|---|---|---|---|---|---|---|---|---|---|---|---|---|---|
| Ala | Gly | Met | Arg | Ser | Ser | Ala | Glu | Glu | Thr | Asn | Ala | Ile | Arg | Lys |
| | 210 | | | | 215 | | | | 220 | | | | | |

```
tta gtt gag cgc acg aat tta cca gtt gta gaa aca ttc caa ggt gca       720
Leu Val Glu Arg Thr Asn Leu Pro Val Val Glu Thr Phe Gln Gly Ala
225                 230                 235                 240 ggt gta att agt cgt gaa tta gaa aat cat ttc ttc ggt cgt gtg ggc       768
Gly Val Ile Ser Arg Glu Leu Glu Asn His Phe Phe Gly Arg Val Gly
            245                 250                 255 tta ttc cgc aat caa gtt ggt gat gaa tta tta cgt aaa agt gat tta       816
Leu Phe Arg Asn Gln Val Gly Asp Glu Leu Leu Arg Lys Ser Asp Leu
        260                 265                 270 gtt gtt aca atc ggt tat gat cca att gaa tac gaa gct agt aac tgg       864
Val Val Thr Ile Gly Tyr Asp Pro Ile Glu Tyr Glu Ala Ser Asn Trp
    275                 280                 285 aat aaa gaa tta gaa aca caa att atc aat att gac gaa gtt caa gct       912
Asn Lys Glu Leu Glu Thr Gln Ile Ile Asn Ile Asp Glu Val Gln Ala
290                 295                 300 gaa att act aat tat atg caa ccg aaa aaa gag ttg att ggt aat att       960
Glu Ile Thr Asn Tyr Met Gln Pro Lys Lys Glu Leu Ile Gly Asn Ile
305                 310                 315                 320 gct aaa acg att gaa atg att tct gaa aaa gtg gat gag cca ttt ata      1008
Ala Lys Thr Ile Glu Met Ile Ser Glu Lys Val Asp Glu Pro Phe Ile
            325                 330                 335 aat caa caa cat tta gac gaa tta gaa caa tta aga aca cat att gat      1056
Asn Gln Gln His Leu Asp Glu Leu Glu Gln Leu Arg Thr His Ile Asp
        340                 345                 350 gaa gaa act ggt att aaa gcg acg cat gaa gaa gga att cta cat cca      1104
Glu Glu Thr Gly Ile Lys Ala Thr His Glu Glu Gly Ile Leu His Pro
    355                 360                 365 gtg gaa att att gaa tct atg caa aag gta tta act gat gat act act      1152
Val Glu Ile Ile Glu Ser Met Gln Lys Val Leu Thr Asp Asp Thr Thr
370                 375                 380 gta aca gtt gat gtt gga agt cac tat att tgg atg gca cgt aat ttc      1200
Val Thr Val Asp Val Gly Ser His Tyr Ile Trp Met Ala Arg Asn Phe
385                 390                 395                 400 aga agt tac aat cca aga cat tta tta ttt agc aat ggt atg caa acg      1248
Arg Ser Tyr Asn Pro Arg His Leu Leu Phe Ser Asn Gly Met Gln Thr
            405                 410                 415 ctt ggt gta gca tta ccg tgg gca att tca gct gca ctt gtg cgc cct      1296
Leu Gly Val Ala Leu Pro Trp Ala Ile Ser Ala Ala Leu Val Arg Pro
        420                 425                 430 aat acg caa gtt gtg tcc gtt gct ggc gat ggt ggc ttt tta ttt tca      1344
Asn Thr Gln Val Val Ser Val Ala Gly Asp Gly Gly Phe Leu Phe Ser
    435                 440                 445 tca caa gat tta gaa acg gcc gta cgt aaa aat tta aat atc atc cag      1392
Ser Gln Asp Leu Glu Thr Ala Val Arg Lys Asn Leu Asn Ile Ile Gln
450                 455                 460 ctt att tgg aat gat gga aaa tat aac atg gtt gaa ttc caa gaa gaa      1440
Leu Ile Trp Asn Asp Gly Lys Tyr Asn Met Val Glu Phe Gln Glu Glu
465                 470                 475                 480 atg aaa tat aaa cgt tcg tca ggt gta gac ttc ggt cct gta gat ttt      1488
Met Lys Tyr Lys Arg Ser Ser Gly Val Asp Phe Gly Pro Val Asp Phe
            485                 490                 495 gta aaa tat gca gaa tca ttt ggc gcg aaa ggt tta cga gtt act aat      1536
Val Lys Tyr Ala Glu Ser Phe Gly Ala Lys Gly Leu Arg Val Thr Asn
        500                 505                 510 caa gaa gaa tta gaa gcg gca att aaa gag ggc tat gaa aca gat ggt      1584
Gln Glu Glu Leu Glu Ala Ala Ile Lys Glu Gly Tyr Glu Thr Asp Gly
    515                 520                 525
```

```
cca gta tta att gat ata cct gta aat tac aaa gat aat atc aaa ctt      1632
Pro Val Leu Ile Asp Ile Pro Val Asn Tyr Lys Asp Asn Ile Lys Leu
    530                 535                 540 tca aca aat atg tta cct gac gta ttt aac taa                          1665
Ser Thr Asn Met Leu Pro Asp Val Phe Asn
545                 550
```

<210> SEQ ID NO 93
<211> LENGTH: 554
<212> TYPE: PRT
<213> ORGANISM: Staphylococcus aureus

<400> SEQUENCE: 93

```
Met Thr Asp Lys Lys Tyr Thr Ala Ala Asp Met Val Ile Asp Thr Leu
1               5                   10                  15

Lys Asn Asn Gly Val Glu Tyr Val Phe Gly Ile Pro Gly Ala Lys Ile
                20                  25                  30

Asp Tyr Leu Phe Asn Ala Leu Ile Asp Asp Gly Pro Glu Leu Ile Val
            35                  40                  45

Thr Arg His Glu Gln Asn Ala Ala Met Met Ala Gln Gly Ile Gly Arg
        50                  55                  60

Leu Thr Gly Lys Pro Gly Val Val Leu Val Thr Ser Gly Pro Gly Val
65                  70                  75                  80

Ser Asn Leu Thr Thr Gly Leu Leu Thr Ala Thr Ser Glu Gly Asp Pro
                85                  90                  95

Val Leu Ala Leu Gly Gly Gln Val Lys Arg Asn Asp Leu Leu Arg Leu
            100                 105                 110

Thr His Gln Ser Ile Asp Asn Ala Ala Leu Leu Lys Tyr Ser Ser Lys
        115                 120                 125

Tyr Ser Glu Glu Val Gln Asp Pro Glu Ser Leu Ser Glu Val Met Thr
    130                 135                 140

Asn Ala Ile Arg Ile Ala Thr Ser Gly Lys Asn Gly Ala Ser Phe Ile
145                 150                 155                 160

Ser Ile Pro Gln Asp Val Ile Ser Ser Pro Val Glu Ser Lys Ala Ile
                165                 170                 175

Ser Leu Cys Gln Lys Pro Asn Leu Gly Val Pro Ser Glu Gln Asp Ile
            180                 185                 190

Asn Asp Val Ile Glu Ala Ile Lys Asn Ala Ser Phe Pro Val Leu Leu
        195                 200                 205

Ala Gly Met Arg Ser Ser Ala Glu Glu Thr Asn Ala Ile Arg Lys
    210                 215                 220

Leu Val Glu Arg Thr Asn Leu Pro Val Val Glu Thr Phe Gln Gly Ala
225                 230                 235                 240

Gly Val Ile Ser Arg Glu Leu Glu Asn His Phe Phe Gly Arg Val Gly
                245                 250                 255

Leu Phe Arg Asn Gln Val Gly Asp Glu Leu Leu Arg Lys Ser Asp Leu
            260                 265                 270

Val Val Thr Ile Gly Tyr Asp Pro Ile Glu Tyr Glu Ala Ser Asn Trp
        275                 280                 285

Asn Lys Glu Leu Glu Thr Gln Ile Ile Asn Ile Asp Glu Val Gln Ala
    290                 295                 300

Glu Ile Thr Asn Tyr Met Gln Pro Lys Lys Glu Leu Ile Gly Asn Ile
305                 310                 315                 320

Ala Lys Thr Ile Glu Met Ile Ser Glu Lys Val Asp Glu Pro Phe Ile
                325                 330                 335
```

```
Asn Gln Gln His Leu Asp Glu Leu Glu Gln Leu Arg Thr His Ile Asp
                340                 345                 350

Glu Glu Thr Gly Ile Lys Ala Thr His Glu Glu Gly Ile Leu His Pro
            355                 360                 365

Val Glu Ile Ile Glu Ser Met Gln Lys Val Leu Thr Asp Asp Thr Thr
370                 375                 380

Val Thr Val Asp Val Gly Ser His Tyr Ile Trp Met Ala Arg Asn Phe
385                 390                 395                 400

Arg Ser Tyr Asn Pro Arg His Leu Leu Phe Ser Asn Gly Met Gln Thr
                405                 410                 415

Leu Gly Val Ala Leu Pro Trp Ala Ile Ser Ala Ala Leu Val Arg Pro
            420                 425                 430

Asn Thr Gln Val Val Ser Val Ala Gly Asp Gly Gly Phe Leu Phe Ser
        435                 440                 445

Ser Gln Asp Leu Glu Thr Ala Val Arg Lys Asn Leu Asn Ile Ile Gln
    450                 455                 460

Leu Ile Trp Asn Asp Gly Lys Tyr Asn Met Val Glu Phe Gln Glu Glu
465                 470                 475                 480

Met Lys Tyr Lys Arg Ser Ser Gly Val Asp Phe Gly Pro Val Asp Phe
                485                 490                 495

Val Lys Tyr Ala Glu Ser Phe Gly Ala Lys Gly Leu Arg Val Thr Asn
            500                 505                 510

Gln Glu Glu Leu Glu Ala Ala Ile Lys Glu Gly Tyr Glu Thr Asp Gly
        515                 520                 525

Pro Val Leu Ile Asp Ile Pro Val Asn Tyr Lys Asp Asn Ile Lys Leu
    530                 535                 540

Ser Thr Asn Met Leu Pro Asp Val Phe Asn
545                 550

<210> SEQ ID NO 94
<211> LENGTH: 1698
<212> TYPE: DNA
<213> ORGANISM: Listeria monocytogenes
<220> FEATURE:
<221> NAME/KEY: CDS
<222> LOCATION: (1)..(1698)

<400> SEQUENCE: 94 atg gcg aaa cta gaa aaa gac caa gaa aaa gta ata aca caa ggg aaa        48
Met Ala Lys Leu Glu Lys Asp Gln Glu Lys Val Ile Thr Gln Gly Lys
1               5                   10                  15 tca gga gcg gat tta gtt gta gac agc tta att aat caa ggt gtt acg        96
Ser Gly Ala Asp Leu Val Val Asp Ser Leu Ile Asn Gln Gly Val Thr
                20                  25                  30 cat gta ttc ggg att ccg gga gcg aaa att gat aaa gtt ttt gat gtg       144
His Val Phe Gly Ile Pro Gly Ala Lys Ile Asp Lys Val Phe Asp Val
            35                  40                  45 atg gaa gaa cgt gga cca gaa tta att gtc agt cgt cat gaa caa aat       192
Met Glu Glu Arg Gly Pro Glu Leu Ile Val Ser Arg His Glu Gln Asn
        50                  55                  60 gcg gcg ttt atg gct gct gct atc ggt cgt cta acc ggg aaa cct ggt       240
Ala Ala Phe Met Ala Ala Ala Ile Gly Arg Leu Thr Gly Lys Pro Gly
65                  70                  75                  80 gtt gta ctt gta act agt gga cct ggc gca tcg aat ctt gca aca ggg       288
Val Val Leu Val Thr Ser Gly Pro Gly Ala Ser Asn Leu Ala Thr Gly
                85                  90                  95 ctt gta acc gca act gca gaa gga gat cca gtc gtt gcg att gct ggt       336
Leu Val Thr Ala Thr Ala Glu Gly Asp Pro Val Val Ala Ile Ala Gly
```

```
                100                 105                 110
aac gta aca agg caa gac cgc tta aaa aga acc cac caa tca atg gat      384
Asn Val Thr Arg Gln Asp Arg Leu Lys Arg Thr His Gln Ser Met Asp
            115                 120                 125 aat gca gca ctt ttc cgt ccg att aca aaa tac agc gaa gaa gta gtt      432
Asn Ala Ala Leu Phe Arg Pro Ile Thr Lys Tyr Ser Glu Glu Val Val
130                 135                 140 cac gcc gaa agt att cca gaa gca atc act aac gct ttt cgc tcg gca      480
His Ala Glu Ser Ile Pro Glu Ala Ile Thr Asn Ala Phe Arg Ser Ala
145                 150                 155                 160 aca gaa cca aac caa ggc gct gct ttt gtc agt ttg cca caa gat atc      528
Thr Glu Pro Asn Gln Gly Ala Ala Phe Val Ser Leu Pro Gln Asp Ile
                165                 170                 175 gtg aac gaa cca aac gta cca gta aaa gcg att cgc cca ctt gct aaa      576
Val Asn Glu Pro Asn Val Pro Val Lys Ala Ile Arg Pro Leu Ala Lys
            180                 185                 190 cca gaa aat ggt cct gct tcc aaa gaa caa gtt gca aaa ctt gtt aca      624
Pro Glu Asn Gly Pro Ala Ser Lys Glu Gln Val Ala Lys Leu Val Thr
        195                 200                 205 cgt ttg aaa aaa gcg aaa tta ccg gta ttg cta ttg ggt atg cga gca      672
Arg Leu Lys Lys Ala Lys Leu Pro Val Leu Leu Leu Gly Met Arg Ala
    210                 215                 220 tct agt cca gaa gta act ggt gca att cgt cgc tta ctc caa aaa aca      720
Ser Ser Pro Glu Val Thr Gly Ala Ile Arg Arg Leu Leu Gln Lys Thr
225                 230                 235                 240 agt atc cca gta gta gaa act ttc caa gca gct ggc gtc att tca cgc      768
Ser Ile Pro Val Val Glu Thr Phe Gln Ala Ala Gly Val Ile Ser Arg
                245                 250                 255 gac tta gaa gat aac ttc ttt gga cgt gtt ggt ctg ttc cgc aac caa      816
Asp Leu Glu Asp Asn Phe Phe Gly Arg Val Gly Leu Phe Arg Asn Gln
            260                 265                 270 cca ggg gat att ttg tta aat aaa gct gat tta gtt att aca gtg ggt      864
Pro Gly Asp Ile Leu Leu Asn Lys Ala Asp Leu Val Ile Thr Val Gly
        275                 280                 285 tat gat cca att gaa tac gat cca aaa gct tgg aat gcc tct ggt gat      912
Tyr Asp Pro Ile Glu Tyr Asp Pro Lys Ala Trp Asn Ala Ser Gly Asp
    290                 295                 300 aga acg att gtc cat tta gac gac att cgc gct gat att gat cat tat      960
Arg Thr Ile Val His Leu Asp Asp Ile Arg Ala Asp Ile Asp His Tyr
305                 310                 315                 320 tac caa cca gtg aca gag cta gtc gga aac atc gcg ctt act tta gac     1008
Tyr Gln Pro Val Thr Glu Leu Val Gly Asn Ile Ala Leu Thr Leu Asp
                325                 330                 335 cga gtg aat gcg aaa ttc agc ggt tta gaa tta gcg gaa aaa gaa ctt     1056
Arg Val Asn Ala Lys Phe Ser Gly Leu Glu Leu Ala Glu Lys Glu Leu
            340                 345                 350 gaa aca tta aaa gaa ctt cat gct caa tta gaa gag cga gat gtt ccg     1104
Glu Thr Leu Lys Glu Leu His Ala Gln Leu Glu Glu Arg Asp Val Pro
        355                 360                 365 cca gaa agt gat gaa act aac cga gta cat cca ttg tcg gtc att caa     1152
Pro Glu Ser Asp Glu Thr Asn Arg Val His Pro Leu Ser Val Ile Gln
    370                 375                 380 aca cta cgt tcg gca att gat gac aac gta act gtg aca gtc gac gtt     1200
Thr Leu Arg Ser Ala Ile Asp Asp Asn Val Thr Val Thr Val Asp Val
385                 390                 395                 400 ggt tca cat tat att tgg atg gca cgt cat ttc cgc tcc tat gaa cca     1248
Gly Ser His Tyr Ile Trp Met Ala Arg His Phe Arg Ser Tyr Glu Pro
                405                 410                 415 cgc cgt ctg ctt ttc agt aac ggt atg caa acg ctt ggt gtt gcg ctt     1296
```

```
Arg Arg Leu Leu Phe Ser Asn Gly Met Gln Thr Leu Gly Val Ala Leu
            420                 425                 430 cct tgg gga att gct gca aca ctt gta cat ccg ggt gaa aaa gtg gtt    1344
Pro Trp Gly Ile Ala Ala Thr Leu Val His Pro Gly Glu Lys Val Val
            435                 440                 445 tcg att tct ggt gac ggt ggt ttc tta ttt tcc gcg atg gaa tta gaa    1392
Ser Ile Ser Gly Asp Gly Gly Phe Leu Phe Ser Ala Met Glu Leu Glu
450                 455                 460 aca gct gtc cgc ttg cgt gcg cca ctt gta cac cta gta tgg aat gac    1440
Thr Ala Val Arg Leu Arg Ala Pro Leu Val His Leu Val Trp Asn Asp
465                 470                 475                 480 gga agc tat gac atg gtt gct ttc caa caa aaa atg aaa tac ggc aaa    1488
Gly Ser Tyr Asp Met Val Ala Phe Gln Gln Lys Met Lys Tyr Gly Lys
                485                 490                 495 gaa gca gct gtt cgt ttt ggc gat gtt gat atc gta aaa ttt gca gaa    1536
Glu Ala Ala Val Arg Phe Gly Asp Val Asp Ile Val Lys Phe Ala Glu
            500                 505                 510 agt ttc gga gca aaa ggt ctt cgc gta aca aat cca gca gaa ctt tct    1584
Ser Phe Gly Ala Lys Gly Leu Arg Val Thr Asn Pro Ala Glu Leu Ser
        515                 520                 525 gat gtg tta aaa gaa gcg ctt gaa aca gaa gga ccc gtc gtt gta gat    1632
Asp Val Leu Lys Glu Ala Leu Glu Thr Glu Gly Pro Val Val Val Asp
530                 535                 540 att cca att gat tac cgt gat aac atc aaa ctt ggc gaa act tta cta    1680
Ile Pro Ile Asp Tyr Arg Asp Asn Ile Lys Leu Gly Glu Thr Leu Leu
545                 550                 555                 560 cct gac caa ttt tat taa                                            1698
Pro Asp Gln Phe Tyr
                565

<210> SEQ ID NO 95
<211> LENGTH: 565
<212> TYPE: PRT
<213> ORGANISM: Listeria monocytogenes

<400> SEQUENCE: 95

Met Ala Lys Leu Glu Lys Asp Gln Glu Lys Val Ile Thr Gln Gly Lys
1               5                   10                  15

Ser Gly Ala Asp Leu Val Val Asp Ser Leu Ile Asn Gln Gly Val Thr
            20                  25                  30

His Val Phe Gly Ile Pro Gly Ala Lys Ile Asp Lys Val Phe Asp Val
        35                  40                  45

Met Glu Glu Arg Gly Pro Glu Leu Ile Val Ser Arg His Glu Gln Asn
    50                  55                  60

Ala Ala Phe Met Ala Ala Ile Gly Arg Leu Thr Gly Lys Pro Gly
65                  70                  75                  80

Val Val Leu Val Thr Ser Gly Pro Gly Ala Ser Asn Leu Ala Thr Gly
                85                  90                  95

Leu Val Thr Ala Thr Ala Glu Gly Asp Pro Val Val Ala Ile Ala Gly
            100                 105                 110

Asn Val Thr Arg Gln Asp Arg Leu Lys Arg Thr His Gln Ser Met Asp
        115                 120                 125

Asn Ala Ala Leu Phe Arg Pro Ile Thr Lys Tyr Ser Glu Glu Val Val
    130                 135                 140

His Ala Glu Ser Ile Pro Glu Ala Ile Thr Asn Ala Phe Arg Ser Ala
145                 150                 155                 160

Thr Glu Pro Asn Gln Gly Ala Ala Phe Val Ser Leu Pro Gln Asp Ile
                165                 170                 175
```

Val Asn Glu Pro Asn Val Pro Val Lys Ala Ile Arg Pro Leu Ala Lys
            180                 185                 190

Pro Glu Asn Gly Pro Ala Ser Lys Glu Gln Val Ala Lys Leu Val Thr
        195                 200                 205

Arg Leu Lys Lys Ala Lys Leu Pro Val Leu Leu Gly Met Arg Ala
    210                 215                 220

Ser Ser Pro Glu Val Thr Gly Ala Ile Arg Arg Leu Leu Gln Lys Thr
225                 230                 235                 240

Ser Ile Pro Val Val Glu Thr Phe Gln Ala Ala Gly Val Ile Ser Arg
                245                 250                 255

Asp Leu Glu Asp Asn Phe Phe Gly Arg Val Gly Leu Phe Arg Asn Gln
            260                 265                 270

Pro Gly Asp Ile Leu Leu Asn Lys Ala Asp Leu Val Ile Thr Val Gly
        275                 280                 285

Tyr Asp Pro Ile Glu Tyr Asp Pro Lys Ala Trp Asn Ala Ser Gly Asp
    290                 295                 300

Arg Thr Ile Val His Leu Asp Asp Ile Arg Ala Asp Ile Asp His Tyr
305                 310                 315                 320

Tyr Gln Pro Val Thr Glu Leu Val Gly Asn Ile Ala Leu Thr Leu Asp
                325                 330                 335

Arg Val Asn Ala Lys Phe Ser Gly Leu Glu Leu Ala Glu Lys Glu Leu
            340                 345                 350

Glu Thr Leu Lys Glu Leu His Ala Gln Leu Glu Glu Arg Asp Val Pro
        355                 360                 365

Pro Glu Ser Asp Glu Thr Asn Arg Val His Pro Leu Ser Val Ile Gln
    370                 375                 380

Thr Leu Arg Ser Ala Ile Asp Asp Asn Val Thr Val Thr Val Asp Val
385                 390                 395                 400

Gly Ser His Tyr Ile Trp Met Ala Arg His Phe Arg Ser Tyr Glu Pro
                405                 410                 415

Arg Arg Leu Leu Phe Ser Asn Gly Met Gln Thr Leu Gly Val Ala Leu
            420                 425                 430

Pro Trp Gly Ile Ala Ala Thr Leu Val His Pro Gly Glu Lys Val Val
        435                 440                 445

Ser Ile Ser Gly Asp Gly Gly Phe Leu Phe Ser Ala Met Glu Leu Glu
    450                 455                 460

Thr Ala Val Arg Leu Arg Ala Pro Leu Val His Leu Val Trp Asn Asp
465                 470                 475                 480

Gly Ser Tyr Asp Met Val Ala Phe Gln Gln Lys Met Lys Tyr Gly Lys
                485                 490                 495

Glu Ala Ala Val Arg Phe Gly Asp Val Asp Ile Val Lys Phe Ala Glu
            500                 505                 510

Ser Phe Gly Ala Lys Gly Leu Arg Val Thr Asn Pro Ala Glu Leu Ser
        515                 520                 525

Asp Val Leu Lys Glu Ala Leu Glu Thr Glu Gly Pro Val Val Val Asp
    530                 535                 540

Ile Pro Ile Asp Tyr Arg Asp Asn Ile Lys Leu Gly Glu Thr Leu Leu
545                 550                 555                 560

Pro Asp Gln Phe Tyr
                565

<210> SEQ ID NO 96
<211> LENGTH: 1680

```
<212> TYPE: DNA
<213> ORGANISM: Streptococcus mutans
<220> FEATURE:
<221> NAME/KEY: CDS
<222> LOCATION: (1)..(1680)

<400> SEQUENCE: 96
```

| | | | | | | | | | | | | | | | | |
|---|---|---|---|---|---|---|---|---|---|---|---|---|---|---|---|---|
| atg | acc | gaa | ata | aat | aag | gaa | ggc | tat | ggg | gct | gac | ctg | att | gta | gac | 48 |
| Met | Thr | Glu | Ile | Asn | Lys | Glu | Gly | Tyr | Gly | Ala | Asp | Leu | Ile | Val | Asp | |
| 1 | | | | 5 | | | | | 10 | | | | | 15 | | |
| agc | ctc | att | aat | cat | gat | gtc | aac | tat | gtt | ttt | gga | atc | cct | ggt | gca | 96 |
| Ser | Leu | Ile | Asn | His | Asp | Val | Asn | Tyr | Val | Phe | Gly | Ile | Pro | Gly | Ala | |
| | | | 20 | | | | | 25 | | | | | 30 | | | |
| aaa | att | gat | cgt | gtc | ttt | gat | acc | tta | gaa | gat | aag | ggg | cca | gaa | ctt | 144 |
| Lys | Ile | Asp | Arg | Val | Phe | Asp | Thr | Leu | Glu | Asp | Lys | Gly | Pro | Glu | Leu | |
| | | 35 | | | | | 40 | | | | | 45 | | | | |
| att | gta | gca | cgc | cat | gag | caa | aat | gct | gct | ttt | atg | gct | caa | gga | att | 192 |
| Ile | Val | Ala | Arg | His | Glu | Gln | Asn | Ala | Ala | Phe | Met | Ala | Gln | Gly | Ile | |
| | 50 | | | | | 55 | | | | | 60 | | | | | |
| ggc | cgt | att | act | ggt | gag | cct | ggt | gtt | gtg | att | aca | acc | agc | ggt | ccc | 240 |
| Gly | Arg | Ile | Thr | Gly | Glu | Pro | Gly | Val | Val | Ile | Thr | Thr | Ser | Gly | Pro | |
| 65 | | | | | 70 | | | | | 75 | | | | | 80 | |
| ggt | gtt | tcc | aat | ctg | gtg | act | ggt | ctt | gtt | act | gcg | aca | gct | gag | gga | 288 |
| Gly | Val | Ser | Asn | Leu | Val | Thr | Gly | Leu | Val | Thr | Ala | Thr | Ala | Glu | Gly | |
| | | | | 85 | | | | | 90 | | | | | 95 | | |
| gat | cct | gtc | ctt | gct | att | ggt | ggt | cag | gtt | aaa | cgt | gct | gat | ttg | ctc | 336 |
| Asp | Pro | Val | Leu | Ala | Ile | Gly | Gly | Gln | Val | Lys | Arg | Ala | Asp | Leu | Leu | |
| | | | 100 | | | | | 105 | | | | | 110 | | | |
| aaa | cgg | gct | cac | cag | tca | atg | aat | aat | gtt | gct | atg | ctc | gat | ccc | att | 384 |
| Lys | Arg | Ala | His | Gln | Ser | Met | Asn | Asn | Val | Ala | Met | Leu | Asp | Pro | Ile | |
| | | 115 | | | | | 120 | | | | | 125 | | | | |
| acc | aaa | tat | tca | gca | gaa | att | cag | gat | ccc | gca | aca | ctt | tca | gaa | aat | 432 |
| Thr | Lys | Tyr | Ser | Ala | Glu | Ile | Gln | Asp | Pro | Ala | Thr | Leu | Ser | Glu | Asn | |
| | 130 | | | | | 135 | | | | | 140 | | | | | |
| att | gct | aat | gcc | tat | cgt | ttg | gct | aaa | gca | gga | aag | ccg | gga | gct | agt | 480 |
| Ile | Ala | Asn | Ala | Tyr | Arg | Leu | Ala | Lys | Ala | Gly | Lys | Pro | Gly | Ala | Ser | |
| 145 | | | | | 150 | | | | | 155 | | | | | 160 | |
| ttc | tta | tct | att | cct | caa | gat | ata | act | gat | agt | cct | gtt | act | gtc | aag | 528 |
| Phe | Leu | Ser | Ile | Pro | Gln | Asp | Ile | Thr | Asp | Ser | Pro | Val | Thr | Val | Lys | |
| | | | | 165 | | | | | 170 | | | | | 175 | | |
| gcg | att | aag | ccc | ttg | aca | gat | cct | aaa | cta | ggt | tca | gcg | tca | gtt | gct | 576 |
| Ala | Ile | Lys | Pro | Leu | Thr | Asp | Pro | Lys | Leu | Gly | Ser | Ala | Ser | Val | Ala | |
| | | | 180 | | | | | 185 | | | | | 190 | | | |
| gat | att | aat | tat | ttg | gca | cag | gcc | ata | aaa | aat | gcg | gtc | ctt | cct | gtc | 624 |
| Asp | Ile | Asn | Tyr | Leu | Ala | Gln | Ala | Ile | Lys | Asn | Ala | Val | Leu | Pro | Val | |
| | | 195 | | | | | 200 | | | | | 205 | | | | |
| tta | ctt | tta | gga | aat | ggt | gcg | tca | acg | gct | gca | gtt | aca | gct | tct | att | 672 |
| Leu | Leu | Leu | Gly | Asn | Gly | Ala | Ser | Thr | Ala | Ala | Val | Thr | Ala | Ser | Ile | |
| | 210 | | | | | 215 | | | | | 220 | | | | | |
| cgc | cgt | ttg | tta | gga | gct | gtc | aag | ctg | cca | gtc | gtt | gaa | act | ttc | caa | 720 |
| Arg | Arg | Leu | Leu | Gly | Ala | Val | Lys | Leu | Pro | Val | Val | Glu | Thr | Phe | Gln | |
| 225 | | | | | 230 | | | | | 235 | | | | | 240 | |
| gga | gct | ggt | att | gtt | tca | aga | gat | tta | gaa | gag | gac | act | ttt | ttt | ggt | 768 |
| Gly | Ala | Gly | Ile | Val | Ser | Arg | Asp | Leu | Glu | Glu | Asp | Thr | Phe | Phe | Gly | |
| | | | | 245 | | | | | 250 | | | | | 255 | | |
| cgt | gtg | ggg | ctt | ttt | cgt | aat | cag | ccc | gga | gat | atg | ttg | ctg | aag | cgt | 816 |
| Arg | Val | Gly | Leu | Phe | Arg | Asn | Gln | Pro | Gly | Asp | Met | Leu | Leu | Lys | Arg | |
| | | | 260 | | | | | 265 | | | | | 270 | | | |
| tct | gac | tta | gtt | atc | gct | att | ggc | tat | gat | cct | att | gaa | tat | gaa | gcg | 864 |
| Ser | Asp | Leu | Val | Ile | Ala | Ile | Gly | Tyr | Asp | Pro | Ile | Glu | Tyr | Glu | Ala | |
| | | 275 | | | | | 280 | | | | | 285 | | | | |

```
cgc aat tgg aat gct gaa att tcg gct cgc att atc gtt att gat gtt      912
Arg Asn Trp Asn Ala Glu Ile Ser Ala Arg Ile Ile Val Ile Asp Val
    290                 295                 300 gct cca gct gaa att gat act tat ttc caa cct gaa cgt gaa tta att      960
Ala Pro Ala Glu Ile Asp Thr Tyr Phe Gln Pro Glu Arg Glu Leu Ile
305                 310                 315                 320 ggt gat ata gct gaa aca ctt gat tta ctc cta cct gct att agt ggc     1008
Gly Asp Ile Ala Glu Thr Leu Asp Leu Leu Leu Pro Ala Ile Ser Gly
            325                 330                 335 tac tca ctt cca aaa ggt tct ctt gac tat ctc aaa ggc ctt cgt gat     1056
Tyr Ser Leu Pro Lys Gly Ser Leu Asp Tyr Leu Lys Gly Leu Arg Asp
        340                 345                 350 aat gta gta gaa gat gtc aaa ttt gat aag aca gtc aaa tcc ggt ctg     1104
Asn Val Val Glu Asp Val Lys Phe Asp Lys Thr Val Lys Ser Gly Leu
    355                 360                 365 gtt cat ccg ctt gat gtg att gat gtc ctt caa aag caa acg act gat     1152
Val His Pro Leu Asp Val Ile Asp Val Leu Gln Lys Gln Thr Thr Asp
370                 375                 380 gat atg aca gta acg gtt gat gtt ggc agc cat tat att tgg atg gct     1200
Asp Met Thr Val Thr Val Asp Val Gly Ser His Tyr Ile Trp Met Ala
385                 390                 395                 400 cgt tat ttt aaa agc tat gaa gca cgg cac tta ctt ttc tca aat ggt     1248
Arg Tyr Phe Lys Ser Tyr Glu Ala Arg His Leu Leu Phe Ser Asn Gly
            405                 410                 415 atg caa acc tta ggt gtt gct ttg cct tgg gca att tcg gca gct ctt     1296
Met Gln Thr Leu Gly Val Ala Leu Pro Trp Ala Ile Ser Ala Ala Leu
        420                 425                 430 gta cgg cca aat gag aag att att tct att tca ggt gat ggt ggt ttc     1344
Val Arg Pro Asn Glu Lys Ile Ile Ser Ile Ser Gly Asp Gly Gly Phe
    435                 440                 445 ctc ttt tct ggc caa gaa ttg gaa aca gct gtt cgt tta cat tta cca     1392
Leu Phe Ser Gly Gln Glu Leu Glu Thr Ala Val Arg Leu His Leu Pro
450                 455                 460 att gtt cat atc att tgg aat gat ggt aaa tat aat atg gtt gaa ttc     1440
Ile Val His Ile Ile Trp Asn Asp Gly Lys Tyr Asn Met Val Glu Phe
465                 470                 475                 480 caa gaa gaa atg aaa tac ggc cgt tca gca ggt gtt gat ttt ggt cct     1488
Gln Glu Glu Met Lys Tyr Gly Arg Ser Ala Gly Val Asp Phe Gly Pro
            485                 490                 495 gtt gat ttt gtc aag tat gct gat agt ttc ggt gct aaa ggt tac cgt     1536
Val Asp Phe Val Lys Tyr Ala Asp Ser Phe Gly Ala Lys Gly Tyr Arg
        500                 505                 510 gct gat agt aaa gaa aag ttt gat caa gtt ctt caa aca gca ctc aag     1584
Ala Asp Ser Lys Glu Lys Phe Asp Gln Val Leu Gln Thr Ala Leu Lys
    515                 520                 525 gaa gct gca aat ggc cca gtt ctc att gat gtt cca atg gac tat aaa     1632
Glu Ala Ala Asn Gly Pro Val Leu Ile Asp Val Pro Met Asp Tyr Lys
530                 535                 540 gat aat gta aaa ttg ggt gaa act att ttg cct gat gaa ttc tac taa     1680
Asp Asn Val Lys Leu Gly Glu Thr Ile Leu Pro Asp Glu Phe Tyr
545                 550                 555

<210> SEQ ID NO 97
<211> LENGTH: 559
<212> TYPE: PRT
<213> ORGANISM: Streptococcus mutans

<400> SEQUENCE: 97

Met Thr Glu Ile Asn Lys Glu Gly Tyr Gly Ala Asp Leu Ile Val Asp
1               5                   10                  15
```

```
Ser Leu Ile Asn His Asp Val Asn Tyr Val Phe Gly Ile Pro Gly Ala
             20                  25                  30

Lys Ile Asp Arg Val Phe Asp Thr Leu Glu Asp Lys Gly Pro Glu Leu
         35                  40                  45

Ile Val Ala Arg His Glu Gln Asn Ala Ala Phe Met Ala Gln Gly Ile
 50                  55                  60

Gly Arg Ile Thr Gly Glu Pro Gly Val Val Ile Thr Thr Ser Gly Pro
 65                  70                  75                  80

Gly Val Ser Asn Leu Val Thr Gly Leu Val Thr Ala Thr Ala Glu Gly
             85                  90                  95

Asp Pro Val Leu Ala Ile Gly Gly Gln Val Lys Arg Ala Asp Leu Leu
            100                 105                 110

Lys Arg Ala His Gln Ser Met Asn Asn Val Ala Met Leu Asp Pro Ile
            115                 120                 125

Thr Lys Tyr Ser Ala Glu Ile Gln Asp Pro Ala Thr Leu Ser Glu Asn
130                 135                 140

Ile Ala Asn Ala Tyr Arg Leu Ala Lys Ala Gly Lys Pro Gly Ala Ser
145                 150                 155                 160

Phe Leu Ser Ile Pro Gln Asp Ile Thr Asp Ser Pro Val Thr Val Lys
                165                 170                 175

Ala Ile Lys Pro Leu Thr Asp Pro Lys Leu Gly Ser Ala Ser Val Ala
            180                 185                 190

Asp Ile Asn Tyr Leu Ala Gln Ala Ile Lys Asn Ala Val Leu Pro Val
            195                 200                 205

Leu Leu Leu Gly Asn Gly Ala Ser Thr Ala Ala Val Thr Ala Ser Ile
            210                 215                 220

Arg Arg Leu Leu Gly Ala Val Lys Leu Pro Val Val Glu Thr Phe Gln
225                 230                 235                 240

Gly Ala Gly Ile Val Ser Arg Asp Leu Glu Glu Asp Thr Phe Phe Gly
                245                 250                 255

Arg Val Gly Leu Phe Arg Asn Gln Pro Gly Asp Met Leu Leu Lys Arg
            260                 265                 270

Ser Asp Leu Val Ile Ala Ile Gly Tyr Asp Pro Ile Glu Tyr Glu Ala
            275                 280                 285

Arg Asn Trp Asn Ala Glu Ile Ser Ala Arg Ile Val Ile Asp Val
            290                 295                 300

Ala Pro Ala Glu Ile Asp Thr Tyr Phe Gln Pro Glu Arg Glu Leu Ile
305                 310                 315                 320

Gly Asp Ile Ala Glu Thr Leu Asp Leu Leu Pro Ala Ile Ser Gly
                325                 330                 335

Tyr Ser Leu Pro Lys Gly Ser Leu Asp Tyr Leu Lys Gly Leu Arg Asp
            340                 345                 350

Asn Val Val Glu Asp Val Lys Phe Asp Lys Thr Val Lys Ser Gly Leu
            355                 360                 365

Val His Pro Leu Asp Val Ile Asp Val Leu Gln Lys Gln Thr Thr Asp
            370                 375                 380

Asp Met Thr Val Thr Val Asp Val Gly Ser His Tyr Ile Trp Met Ala
385                 390                 395                 400

Arg Tyr Phe Lys Ser Tyr Glu Ala Arg His Leu Leu Phe Ser Asn Gly
                405                 410                 415

Met Gln Thr Leu Gly Val Ala Leu Pro Trp Ala Ile Ser Ala Ala Leu
            420                 425                 430
```

```
Val Arg Pro Asn Glu Lys Ile Ile Ser Ile Ser Gly Asp Gly Gly Phe
         435                 440                 445

Leu Phe Ser Gly Gln Glu Leu Glu Thr Ala Val Arg Leu His Leu Pro
    450                 455                 460

Ile Val His Ile Ile Trp Asn Asp Gly Lys Tyr Asn Met Val Glu Phe
465                 470                 475                 480

Gln Glu Glu Met Lys Tyr Gly Arg Ser Ala Gly Val Asp Phe Gly Pro
                485                 490                 495

Val Asp Phe Val Lys Tyr Ala Asp Ser Phe Gly Ala Lys Gly Tyr Arg
            500                 505                 510

Ala Asp Ser Lys Glu Lys Phe Asp Gln Val Leu Gln Thr Ala Leu Lys
            515                 520                 525

Glu Ala Ala Asn Gly Pro Val Leu Ile Asp Val Pro Met Asp Tyr Lys
        530                 535                 540

Asp Asn Val Lys Leu Gly Glu Thr Ile Leu Pro Asp Glu Phe Tyr
545                 550                 555

<210> SEQ ID NO 98
<211> LENGTH: 1683
<212> TYPE: DNA
<213> ORGANISM: Streptococcus thermophilus
<220> FEATURE:
<221> NAME/KEY: CDS
<222> LOCATION: (1)..(1683)

<400> SEQUENCE: 98 gtg ttc atg tca gaa gaa aag caa ttg tat ggt gca gat tta gtg gtt     48
Val Phe Met Ser Glu Glu Lys Gln Leu Tyr Gly Ala Asp Leu Val Val
1               5                   10                  15 gat agt ttg atc aac cat gat gtt gag tat gtc ttt ggg att cca ggc     96
Asp Ser Leu Ile Asn His Asp Val Glu Tyr Val Phe Gly Ile Pro Gly
                20                  25                  30 gca aaa atc gat agg gtt ttt gat acc ttg gaa gat aag gga cct gaa    144
Ala Lys Ile Asp Arg Val Phe Asp Thr Leu Glu Asp Lys Gly Pro Glu
            35                  40                  45 ttg att gtt gcc cgt cat gag caa aat gct gct ttt atg gct caa ggt    192
Leu Ile Val Ala Arg His Glu Gln Asn Ala Ala Phe Met Ala Gln Gly
        50                  55                  60 gtt gga cgt att act ggg aaa cca ggt gta gta ttg gta aca tct ggt    240
Val Gly Arg Ile Thr Gly Lys Pro Gly Val Val Leu Val Thr Ser Gly
65                  70                  75                  80 cca ggt gtc tcc aat ttg gct act ggt ttg gta aca gcg acg gat gaa    288
Pro Gly Val Ser Asn Leu Ala Thr Gly Leu Val Thr Ala Thr Asp Glu
                85                  90                  95 gga gac cct gtt ctt gct att ggt ggt cag gtt aag cgt gca gat ctc    336
Gly Asp Pro Val Leu Ala Ile Gly Gly Gln Val Lys Arg Ala Asp Leu
            100                 105                 110 ttg aaa cgt gcc cac caa tca atg aat aac gtt gct atg ctt gag cca    384
Leu Lys Arg Ala His Gln Ser Met Asn Asn Val Ala Met Leu Glu Pro
        115                 120                 125 att acc aaa tat gct gct gaa gta cat gat gct aac acc ctt tct gaa    432
Ile Thr Lys Tyr Ala Ala Glu Val His Asp Ala Asn Thr Leu Ser Glu
130                 135                 140 acg gtt gct aat gcc tat cgt cac gct aag tca ggg aaa cca ggt gca    480
Thr Val Ala Asn Ala Tyr Arg His Ala Lys Ser Gly Lys Pro Gly Ala
145                 150                 155                 160 agc ttc att tca att cct caa gac gtg acg gat gct ccg gtc agt gtt    528
Ser Phe Ile Ser Ile Pro Gln Asp Val Thr Asp Ala Pro Val Ser Val
                165                 170                 175
```

-continued

```
aag gct att aag cct atg aca gat cca aaa ctt ggt tca gca tct gtt      576
Lys Ala Ile Lys Pro Met Thr Asp Pro Lys Leu Gly Ser Ala Ser Val
            180                 185                 190 tct gat att aac tat cta gca caa gcc att aaa aat gca gtg ttg cca      624
Ser Asp Ile Asn Tyr Leu Ala Gln Ala Ile Lys Asn Ala Val Leu Pro
        195                 200                 205 gtc ttt ctt ttg ggg aat ggt gcc tca tca gaa gcc gta act tac tct      672
Val Phe Leu Leu Gly Asn Gly Ala Ser Ser Glu Ala Val Thr Tyr Ser
    210                 215                 220 att cgc caa att ttg aag cat gtt aaa ttg cca gtt gtt gaa act ttc      720
Ile Arg Gln Ile Leu Lys His Val Lys Leu Pro Val Val Glu Thr Phe
225                 230                 235                 240 caa ggt gcc ggt atc gtg tca cgt gac ctt gaa gaa gat act ttc ttt      768
Gln Gly Ala Gly Ile Val Ser Arg Asp Leu Glu Glu Asp Thr Phe Phe
            245                 250                 255 ggt cgt gta ggt ctt ttc cgt aac caa ccc gga gac atg ttg ctt aaa      816
Gly Arg Val Gly Leu Phe Arg Asn Gln Pro Gly Asp Met Leu Leu Lys
        260                 265                 270 aaa tcc gac tta gtt att gcc att ggt tat gat cca atc gaa tat gaa      864
Lys Ser Asp Leu Val Ile Ala Ile Gly Tyr Asp Pro Ile Glu Tyr Glu
    275                 280                 285 gca cgt aac tgg aat gct gaa att tca gca cgt atc atc gtt att gat      912
Ala Arg Asn Trp Asn Ala Glu Ile Ser Ala Arg Ile Ile Val Ile Asp
290                 295                 300 gtc gag ccg gcc gag gtg gac act tac ttc caa ccg gaa cgt gaa ttg      960
Val Glu Pro Ala Glu Val Asp Thr Tyr Phe Gln Pro Glu Arg Glu Leu
305                 310                 315                 320 att ggt aat gta gaa gcg agc tta gac ttg ctt ttg ccc gct att caa     1008
Ile Gly Asn Val Glu Ala Ser Leu Asp Leu Leu Leu Pro Ala Ile Gln
            325                 330                 335 ggt tat aaa ttg cct gaa ggt gcg gtt gaa tat ctt aaa ggt ttg aaa     1056
Gly Tyr Lys Leu Pro Glu Gly Ala Val Glu Tyr Leu Lys Gly Leu Lys
        340                 345                 350 aac aat gtt gtt gag gat gtt aag ttt gac cgt cag cct gat gaa ggt     1104
Asn Asn Val Val Glu Asp Val Lys Phe Asp Arg Gln Pro Asp Glu Gly
    355                 360                 365 acg gtg cat ccg cta gat ttc atc gaa aat ttg caa gaa cac aca gat     1152
Thr Val His Pro Leu Asp Phe Ile Glu Asn Leu Gln Glu His Thr Asp
370                 375                 380 gat gat atg act gtt acg ttt gat gtt ggt agt cac tat att tgg atg     1200
Asp Asp Met Thr Val Thr Phe Asp Val Gly Ser His Tyr Ile Trp Met
385                 390                 395                 400 gca cgt tat ctc aaa tcg tat gaa cca cgt cat ttg ctt ttc tca aat     1248
Ala Arg Tyr Leu Lys Ser Tyr Glu Pro Arg His Leu Leu Phe Ser Asn
            405                 410                 415 ggg atg caa acg ata ggt att gct att aca tgg gct atc tct gca gca     1296
Gly Met Gln Thr Ile Gly Ile Ala Ile Thr Trp Ala Ile Ser Ala Ala
        420                 425                 430 ttg gtt cgt cct aag aca aaa gtg att tct gta tct ggt gat ggt ggt     1344
Leu Val Arg Pro Lys Thr Lys Val Ile Ser Val Ser Gly Asp Gly Gly
    435                 440                 445 ttc ctc ttc tca gca caa gaa ttg gaa aca gca gtt cgt ttg aaa ttg     1392
Phe Leu Phe Ser Ala Gln Glu Leu Glu Thr Ala Val Arg Leu Lys Leu
450                 455                 460 cca att gtc cat att atc tgg aac gat ggt cat tac aat atg gtg gaa     1440
Pro Ile Val His Ile Ile Trp Asn Asp Gly His Tyr Asn Met Val Glu
465                 470                 475                 480 ttc cag gaa gaa atg aag tac ggt cgt tca tct ggg gtt gac ttt ggt     1488
Phe Gln Glu Glu Met Lys Tyr Gly Arg Ser Ser Gly Val Asp Phe Gly
            485                 490                 495
```

```
cct gta gat ttt gta aaa tat gct gag agc ttt gga gcc aaa ggt tat     1536
Pro Val Asp Phe Val Lys Tyr Ala Glu Ser Phe Gly Ala Lys Gly Tyr
            500                 505                 510 cgt gca aca agt aaa gca gcg ttt gct agc ttg ctt caa gag gct ttg     1584
Arg Ala Thr Ser Lys Ala Ala Phe Ala Ser Leu Leu Gln Glu Ala Leu
        515                 520                 525 act cag gct gta gat gga cca gtc ctt att gat gtt cca att gac tat     1632
Thr Gln Ala Val Asp Gly Pro Val Leu Ile Asp Val Pro Ile Asp Tyr
    530                 535                 540 aaa gat aac att aaa ctc ggc gaa act att ttg cca gat gaa ttt tac     1680
Lys Asp Asn Ile Lys Leu Gly Glu Thr Ile Leu Pro Asp Glu Phe Tyr
545                 550                 555                 560 taa                                                                 1683

<210> SEQ ID NO 99
<211> LENGTH: 560
<212> TYPE: PRT
<213> ORGANISM: Streptococcus thermophilus

<400> SEQUENCE: 99
```

Val Phe Met Ser Glu Glu Lys Gln Leu Tyr Gly Ala Asp Leu Val Val
1               5                   10                  15

Asp Ser Leu Ile Asn His Asp Val Glu Tyr Val Phe Gly Ile Pro Gly
            20                  25                  30

Ala Lys Ile Asp Arg Val Phe Asp Thr Leu Glu Asp Lys Gly Pro Glu
        35                  40                  45

Leu Ile Val Ala Arg His Glu Gln Asn Ala Ala Phe Met Ala Gln Gly
    50                  55                  60

Val Gly Arg Ile Thr Gly Lys Pro Gly Val Val Leu Val Thr Ser Gly
65                  70                  75                  80

Pro Gly Val Ser Asn Leu Ala Thr Gly Leu Val Thr Ala Thr Asp Glu
                85                  90                  95

Gly Asp Pro Val Leu Ala Ile Gly Gly Gln Val Lys Arg Ala Asp Leu
            100                 105                 110

Leu Lys Arg Ala His Gln Ser Met Asn Asn Val Ala Met Leu Glu Pro
        115                 120                 125

Ile Thr Lys Tyr Ala Ala Glu Val His Asp Ala Asn Thr Leu Ser Glu
    130                 135                 140

Thr Val Ala Asn Ala Tyr Arg His Ala Lys Ser Gly Lys Pro Gly Ala
145                 150                 155                 160

Ser Phe Ile Ser Ile Pro Gln Asp Val Thr Asp Ala Pro Val Ser Val
                165                 170                 175

Lys Ala Ile Lys Pro Met Thr Asp Pro Lys Leu Gly Ser Ala Ser Val
            180                 185                 190

Ser Asp Ile Asn Tyr Leu Ala Gln Ala Ile Lys Asn Ala Val Leu Pro
        195                 200                 205

Val Phe Leu Leu Gly Asn Gly Ala Ser Ser Glu Ala Val Thr Tyr Ser
    210                 215                 220

Ile Arg Gln Ile Leu Lys His Val Lys Leu Pro Val Val Glu Thr Phe
225                 230                 235                 240

Gln Gly Ala Gly Ile Val Ser Arg Asp Leu Glu Glu Asp Thr Phe Phe
                245                 250                 255

Gly Arg Val Gly Leu Phe Arg Asn Gln Pro Gly Asp Met Leu Leu Lys
            260                 265                 270

Lys Ser Asp Leu Val Ile Ala Ile Gly Tyr Asp Pro Ile Glu Tyr Glu

```
           275                 280                 285
Ala Arg Asn Trp Asn Ala Glu Ile Ser Ala Arg Ile Val Ile Asp
    290                 295                 300

Val Glu Pro Ala Glu Val Asp Thr Tyr Phe Gln Pro Glu Arg Glu Leu
305                 310                 315                 320

Ile Gly Asn Val Glu Ala Ser Leu Asp Leu Leu Pro Ala Ile Gln
                    325                 330                 335

Gly Tyr Lys Leu Pro Glu Gly Ala Val Glu Tyr Leu Lys Gly Leu Lys
                340                 345                 350

Asn Asn Val Val Glu Asp Val Lys Phe Asp Arg Gln Pro Asp Glu Gly
                    355                 360                 365

Thr Val His Pro Leu Asp Phe Ile Glu Asn Leu Gln Glu His Thr Asp
370                 375                 380

Asp Asp Met Thr Val Thr Phe Asp Val Gly Ser His Tyr Ile Trp Met
385                 390                 395                 400

Ala Arg Tyr Leu Lys Ser Tyr Glu Pro Arg His Leu Leu Phe Ser Asn
                    405                 410                 415

Gly Met Gln Thr Ile Gly Ile Ala Ile Thr Trp Ala Ile Ser Ala Ala
                    420                 425                 430

Leu Val Arg Pro Lys Thr Lys Val Ile Ser Val Ser Gly Asp Gly Gly
                435                 440                 445

Phe Leu Phe Ser Ala Gln Glu Leu Glu Thr Ala Val Arg Leu Lys Leu
450                 455                 460

Pro Ile Val His Ile Ile Trp Asn Asp Gly His Tyr Asn Met Val Glu
465                 470                 475                 480

Phe Gln Glu Glu Met Lys Tyr Gly Arg Ser Ser Gly Val Asp Phe Gly
                    485                 490                 495

Pro Val Asp Phe Val Lys Tyr Ala Glu Ser Phe Gly Ala Lys Gly Tyr
                500                 505                 510

Arg Ala Thr Ser Lys Ala Ala Phe Ala Ser Leu Leu Gln Glu Ala Leu
                515                 520                 525

Thr Gln Ala Val Asp Gly Pro Val Leu Ile Asp Val Pro Ile Asp Tyr
530                 535                 540

Lys Asp Asn Ile Lys Leu Gly Glu Thr Ile Leu Pro Asp Glu Phe Tyr
545                 550                 555                 560

<210> SEQ ID NO 100
<211> LENGTH: 1665
<212> TYPE: DNA
<213> ORGANISM: Vibrio angustum
<220> FEATURE:
<221> NAME/KEY: CDS
<222> LOCATION: (1)..(1665)

<400> SEQUENCE: 100 atg tcg gat aaa acc gtc tct ggt gct gaa ctg gtt gtt gaa act tta    48
Met Ser Asp Lys Thr Val Ser Gly Ala Glu Leu Val Val Glu Thr Leu
1               5                   10                  15 aat gca cat aac gtt cca cac att ttt ggt att cct gga gca aag gtg    96
Asn Ala His Asn Val Pro His Ile Phe Gly Ile Pro Gly Ala Lys Val
                20                  25                  30 gat gct gtt ttc gat gct gtt tgt gat aac gga cca gaa atc att att   144
Asp Ala Val Phe Asp Ala Val Cys Asp Asn Gly Pro Glu Ile Ile Ile
            35                  40                  45 tgt cat cat gaa caa aat gca gcg ttt atg gca gca gca act ggg cgt   192
Cys His His Glu Gln Asn Ala Ala Phe Met Ala Ala Ala Thr Gly Arg
        50                  55                  60
```

-continued

| | | | |
|---|---|---|---|
| tta acg ggt aaa gca ggc att tgt tta gca acc tct gga cca ggc gca<br>Leu Thr Gly Lys Ala Gly Ile Cys Leu Ala Thr Ser Gly Pro Gly Ala<br>65                    70                    75                    80 | 240 |

```
tta acg ggt aaa gca ggc att tgt tta gca acc tct gga cca ggc gca        240
Leu Thr Gly Lys Ala Gly Ile Cys Leu Ala Thr Ser Gly Pro Gly Ala
 65                  70                  75                  80 tca aac ctt gtc aca ggc gtt gca aca gcg aat agt gaa ggt gat cct        288
Ser Asn Leu Val Thr Gly Val Ala Thr Ala Asn Ser Glu Gly Asp Pro
                 85                  90                  95 gtg gtt gca ctt gca ggt gct gta cct ctt tct atg tat tct cac aat        336
Val Val Ala Leu Ala Gly Ala Val Pro Leu Ser Met Tyr Ser His Asn
            100                 105                 110 act cat caa tcc atg gat acc cgt tca ctg ttt act cct atc acc aag        384
Thr His Gln Ser Met Asp Thr Arg Ser Leu Phe Thr Pro Ile Thr Lys
        115                 120                 125 ttt tca gca gaa gtg atg gat agc agc tcg gta tct gat gtt gta cat        432
Phe Ser Ala Glu Val Met Asp Ser Ser Ser Val Ser Asp Val Val His
130                 135                 140 aaa gct ttt cgt att gca gag caa cct acc caa ggt gct agc ttt gtt        480
Lys Ala Phe Arg Ile Ala Glu Gln Pro Thr Gln Gly Ala Ser Phe Val
145                 150                 155                 160 agt cta ccg caa gat att cta act aac cgt att cct tac cag cca gta        528
Ser Leu Pro Gln Asp Ile Leu Thr Asn Arg Ile Pro Tyr Gln Pro Val
                165                 170                 175 caa cag cct aat cca att ttg ttc ggt ggt gca cac cca caa gct att        576
Gln Gln Pro Asn Pro Ile Leu Phe Gly Gly Ala His Pro Gln Ala Ile
            180                 185                 190 cgt cag gct gct gat cgc att aat gct gca aaa aat ccg gtg tta tta        624
Arg Gln Ala Ala Asp Arg Ile Asn Ala Ala Lys Asn Pro Val Leu Leu
        195                 200                 205 ctg ggc atg gat gca agc cag cct ttt gtt gct gat gct att cgc caa        672
Leu Gly Met Asp Ala Ser Gln Pro Phe Val Ala Asp Ala Ile Arg Gln
210                 215                 220 cta ctc aaa caa aca cca att gcc gtt gtg aat acg ttt gcc gca gct        720
Leu Leu Lys Gln Thr Pro Ile Ala Val Val Asn Thr Phe Ala Ala Ala
225                 230                 235                 240 ggg gtt att tct cat gat tta tac aac tgc ttt tta ggt cgt gtt ggc        768
Gly Val Ile Ser His Asp Leu Tyr Asn Cys Phe Leu Gly Arg Val Gly
                245                 250                 255 tta ttt aaa aat caa ccc ggt gat att gca tta aac agt gca gat tta        816
Leu Phe Lys Asn Gln Pro Gly Asp Ile Ala Leu Asn Ser Ala Asp Leu
            260                 265                 270 atc att acc att ggc tac agc cca att gaa tac gat ccg att ctt tgg        864
Ile Ile Thr Ile Gly Tyr Ser Pro Ile Glu Tyr Asp Pro Ile Leu Trp
        275                 280                 285 aat aaa gat gca aac aca cca att att cat att ggt tat caa caa gca        912
Asn Lys Asp Ala Asn Thr Pro Ile Ile His Ile Gly Tyr Gln Gln Ala
290                 295                 300 gat tta gaa att agc tat aac cct gtt tgt gaa gtt gtg ggt gac tta        960
Asp Leu Glu Ile Ser Tyr Asn Pro Val Cys Glu Val Val Gly Asp Leu
305                 310                 315                 320 gcg gtg tct gtc acg tct att gct tct gaa tta gat aag cga gaa tca       1008
Ala Val Ser Val Thr Ser Ile Ala Ser Glu Leu Asp Lys Arg Glu Ser
                325                 330                 335 tta gaa aat aac caa caa atc caa tta tta cgc cac gat tta caa cat       1056
Leu Glu Asn Asn Gln Gln Ile Gln Leu Leu Arg His Asp Leu Gln His
            340                 345                 350 att atg cag atg ggg gta aat aaa acc tca aca aac ggc gtt cac ccg       1104
Ile Met Gln Met Gly Val Asn Lys Thr Ser Thr Asn Gly Val His Pro
        355                 360                 365 ctt cgt ttt gtt cat gag tta cgt cgc ttt gtt agt gac gac acc act       1152
Leu Arg Phe Val His Glu Leu Arg Arg Phe Val Ser Asp Asp Thr Thr
```

```
                370              375              380
gta tgt tgt gat gta ggc tct att tat att tgg atg gca cgt tac ttc    1200
Val Cys Cys Asp Val Gly Ser Ile Tyr Ile Trp Met Ala Arg Tyr Phe
385              390              395              400 cac agc ttt gaa cct cgt cgt tta ttg ttc agc aat ggc caa caa aca    1248
His Ser Phe Glu Pro Arg Arg Leu Leu Phe Ser Asn Gly Gln Gln Thr
                405              410              415 ttg ggc gta gct tta cct tgg gca att gca gct tcc ctt ctt cac cct    1296
Leu Gly Val Ala Leu Pro Trp Ala Ile Ala Ala Ser Leu Leu His Pro
            420              425              430 aat gaa aaa gta att tcc atg tct ggt gat ggt ggc ttc cta ttc tca    1344
Asn Glu Lys Val Ile Ser Met Ser Gly Asp Gly Gly Phe Leu Phe Ser
        435              440              445 tca atg gaa tta gcc acg gcc gtt cgc cat aaa tgt aat atc gtt cac    1392
Ser Met Glu Leu Ala Thr Ala Val Arg His Lys Cys Asn Ile Val His
    450              455              460 ttt gtt tgg aca gat cac agt tat gac atg gtt aag atc caa cag ctt    1440
Phe Val Trp Thr Asp His Ser Tyr Asp Met Val Lys Ile Gln Gln Leu
465              470              475              480 aaa aag tat ggt cga gag agt gcc gtc agc ttt ata ggt cct gat att    1488
Lys Lys Tyr Gly Arg Glu Ser Ala Val Ser Phe Ile Gly Pro Asp Ile
                485              490              495 gtt aag tac gca gaa agc ttc ggc gca cat ggt tta gcg atc aat act    1536
Val Lys Tyr Ala Glu Ser Phe Gly Ala His Gly Leu Ala Ile Asn Thr
            500              505              510 gcc gat gat att gag cct gtt atg cga aaa gct atg agc tta agt ggc    1584
Ala Asp Asp Ile Glu Pro Val Met Arg Lys Ala Met Ser Leu Ser Gly
        515              520              525 cca gta ttg gtc aac gtc aat gtt gat tat agc gat aac agt cgc cta    1632
Pro Val Leu Val Asn Val Asn Val Asp Tyr Ser Asp Asn Ser Arg Leu
    530              535              540 ctt gat caa ctt cat cca tgc caa caa gat taa                        1665
Leu Asp Gln Leu His Pro Cys Gln Gln Asp
545              550
```

<210> SEQ ID NO 101
<211> LENGTH: 554
<212> TYPE: PRT
<213> ORGANISM: Vibrio angustum

<400> SEQUENCE: 101

```
Met Ser Asp Lys Thr Val Ser Gly Ala Glu Leu Val Glu Thr Leu
1               5                   10                  15

Asn Ala His Asn Val Pro His Ile Phe Gly Ile Pro Gly Ala Lys Val
                20                  25                  30

Asp Ala Val Phe Asp Ala Val Cys Asp Asn Gly Pro Glu Ile Ile Ile
            35                  40                  45

Cys His His Glu Gln Asn Ala Ala Phe Met Ala Ala Thr Gly Arg
    50                  55                  60

Leu Thr Gly Lys Ala Gly Ile Cys Leu Ala Thr Ser Gly Pro Gly Ala
65                  70                  75                  80

Ser Asn Leu Val Thr Gly Val Ala Thr Ala Asn Ser Glu Gly Asp Pro
                85                  90                  95

Val Val Ala Leu Ala Gly Ala Val Pro Leu Ser Met Tyr Ser His Asn
            100                 105                 110

Thr His Gln Ser Met Asp Thr Arg Ser Leu Phe Thr Pro Ile Thr Lys
        115                 120                 125

Phe Ser Ala Glu Val Met Asp Ser Ser Val Ser Asp Val Val His
```

```
            130                 135                 140
Lys Ala Phe Arg Ile Ala Glu Gln Pro Thr Gln Gly Ala Ser Phe Val
145                 150                 155                 160

Ser Leu Pro Gln Asp Ile Leu Thr Asn Arg Ile Pro Tyr Gln Pro Val
                165                 170                 175

Gln Gln Pro Asn Pro Ile Leu Phe Gly Gly Ala His Pro Gln Ala Ile
                180                 185                 190

Arg Gln Ala Ala Asp Arg Ile Asn Ala Ala Lys Asn Pro Val Leu Leu
                195                 200                 205

Leu Gly Met Asp Ala Ser Gln Pro Phe Val Ala Asp Ala Ile Arg Gln
                210                 215                 220

Leu Leu Lys Gln Thr Pro Ile Ala Val Val Asn Thr Phe Ala Ala Ala
225                 230                 235                 240

Gly Val Ile Ser His Asp Leu Tyr Asn Cys Phe Leu Gly Arg Val Gly
                245                 250                 255

Leu Phe Lys Asn Gln Pro Gly Asp Ile Ala Leu Asn Ser Ala Asp Leu
                260                 265                 270

Ile Ile Thr Ile Gly Tyr Ser Pro Ile Glu Tyr Asp Pro Ile Leu Trp
                275                 280                 285

Asn Lys Asp Ala Asn Thr Pro Ile Ile His Ile Gly Tyr Gln Gln Ala
                290                 295                 300

Asp Leu Glu Ile Ser Tyr Asn Pro Val Cys Glu Val Val Gly Asp Leu
305                 310                 315                 320

Ala Val Ser Val Thr Ser Ile Ala Ser Glu Leu Asp Lys Arg Glu Ser
                325                 330                 335

Leu Glu Asn Asn Gln Gln Ile Gln Leu Leu Arg His Asp Leu Gln His
                340                 345                 350

Ile Met Gln Met Gly Val Asn Lys Thr Ser Thr Asn Gly Val His Pro
                355                 360                 365

Leu Arg Phe Val His Glu Leu Arg Arg Phe Val Ser Asp Asp Thr Thr
                370                 375                 380

Val Cys Cys Asp Val Gly Ser Ile Tyr Ile Trp Met Ala Arg Tyr Phe
385                 390                 395                 400

His Ser Phe Glu Pro Arg Arg Leu Leu Phe Ser Asn Gly Gln Gln Thr
                405                 410                 415

Leu Gly Val Ala Leu Pro Trp Ala Ile Ala Ala Ser Leu Leu His Pro
                420                 425                 430

Asn Glu Lys Val Ile Ser Met Ser Gly Asp Gly Gly Phe Leu Phe Ser
                435                 440                 445

Ser Met Glu Leu Ala Thr Ala Val Arg His Lys Cys Asn Ile Val His
450                 455                 460

Phe Val Trp Thr Asp His Ser Tyr Asp Met Val Lys Ile Gln Gln Leu
465                 470                 475                 480

Lys Lys Tyr Gly Arg Glu Ser Ala Val Ser Phe Ile Gly Pro Asp Ile
                485                 490                 495

Val Lys Tyr Ala Glu Ser Phe Gly Ala His Gly Leu Ala Ile Asn Thr
                500                 505                 510

Ala Asp Asp Ile Glu Pro Val Met Arg Lys Ala Met Ser Leu Ser Gly
                515                 520                 525

Pro Val Leu Val Asn Val Asn Val Asp Tyr Ser Asp Asn Ser Arg Leu
530                 535                 540

Leu Asp Gln Leu His Pro Cys Gln Gln Asp
545                 550
```

<210> SEQ ID NO 102
<211> LENGTH: 1689
<212> TYPE: DNA
<213> ORGANISM: Bacillus cereus

<400> SEQUENCE: 102

```
ttgagtacag gtgtaaaagc aaacgacgtg aagacaaaaa caaaaggagc agatcttgtt     60
gttgattgtt taattaaaca aggtgttaca catgttttcg gtattccagg agcaaagatt    120
gactctgtat ttgatgtact gcaagaaaga ggaccagagt taattgtttg tcgtcatgaa    180
caaaatgcag catttatggc agctgctatt ggtagattaa caggaaaacc gggcgtatgt    240
cttgtaactt caggaccagg gacatcaaat ttagcgacag gtcttgttac tgcgaatgcg    300
gagagtgatc ccgttgttgc tttagctggt gcagttccgc gtacggatcg attaaaacgt    360
acacatcaat ctatggataa tgctgcacta ttcgaaccaa tcacaaaata tagcgtagaa    420
gtagagcatc ctgataatgt gccagaagca ttatcaaatg cattccgaag tgcgacttct    480
acaaatccag gagcaacttt agtaagtttg ccgcaagacg ttatgactgc ggaaacgact    540
gtagagtcta tcggtgcgct ttctaagcca cagcttggaa tcgctcccac acatgatatt    600
acatatgtag tagataaaat aaaagcagcg aaattaccag ttattttact cggtatgaga    660
gcgagcacaa atgaagtgac gaaagccgtt cgtaaattaa ttgcggatac agaacttcct    720
gtcgttgaaa catatcaagc ggctggtgcc atttcacgtg agttagaaga tcatttcttc    780
ggccgtgttg gactattccg taaccaacca ggtgatattt tactagaaga ggcagatctt    840
gttatttcta tcggttatga tccaattgag tatgatccaa agttctggaa taaacttgga    900
gacagaacga ttattcatct tgatgaccat caagcagata tagatcatga ttaccaacca    960
gagcgtgaat taattggtga tattgcctta acagtaaata gcatcgcaga aaagttaccg   1020
aaacttgtgt taagtacgaa atcagaagca gtgttagaac gattacgcgc gaaattatca   1080
gaacaagcag aagttccaaa tcgtccttca gaaggtgtta cacatccgct tcaagtgatt   1140
cgtacacttc gttctttaat tagtgacgac acaaccgtta catgtgacat cggttcccat   1200
tctatttgga tggcgagatg tttccgttct tatgaaccac gtagattatt atttagtaac   1260
ggtatgcaga cgttaggtgt tgcacttcct tgggcaattg ctgctacttt agtagaacca   1320
ggtaaaaaag tagtttccgt atcaggtgac ggtggtttct tattctcagc gatggagtta   1380
gaaacggcgg tacgtttaaa ttctccaatc gtccatcttg tttggagaga cggcacatat   1440
gatatggttg cattccaaca aatgatgaaa tacggcagaa catcagctac agagtttggt   1500
gatgttgatc ttgttaaata tgcggaaagt ttcggggcgt taggtcttcg tgttaacacg   1560
cctgatgaat tagaaggggt attgaaagaa gcactagcag cagacggccc tgtcattatt   1620
gatattccaa ttgactatcg tgacaacatt aaattaagcg aaaaattatt accaaaccaa   1680
ttaaactaa                                                           1689
```

<210> SEQ ID NO 103
<211> LENGTH: 562
<212> TYPE: PRT
<213> ORGANISM: Bacillus cereus

<400> SEQUENCE: 103

```
Met Ser Thr Gly Val Lys Ala Asn Asp Val Lys Thr Lys Thr Lys Gly
1               5                   10                  15

Ala Asp Leu Val Val Asp Cys Leu Ile Lys Gln Gly Val Thr His Val
```

```
            20                  25                  30
Phe Gly Ile Pro Gly Ala Lys Ile Asp Ser Val Phe Asp Val Leu Gln
            35                  40                  45

Glu Arg Gly Pro Glu Leu Ile Val Cys Arg His Glu Gln Asn Ala Ala
 50                  55                  60

Phe Met Ala Ala Ala Ile Gly Arg Leu Thr Gly Lys Pro Gly Val Cys
 65                  70                  75                  80

Leu Val Thr Ser Gly Pro Gly Thr Ser Asn Leu Ala Thr Gly Leu Val
                 85                  90                  95

Thr Ala Asn Ala Glu Ser Asp Pro Val Val Ala Leu Ala Gly Ala Val
                100                 105                 110

Pro Arg Thr Asp Arg Leu Lys Arg Thr His Gln Ser Met Asp Asn Ala
                115                 120                 125

Ala Leu Phe Glu Pro Ile Thr Lys Tyr Ser Val Glu Val Glu His Pro
            130                 135                 140

Asp Asn Val Pro Glu Ala Leu Ser Asn Ala Phe Arg Ser Ala Thr Ser
145                 150                 155                 160

Thr Asn Pro Gly Ala Thr Leu Val Ser Leu Pro Gln Asp Val Met Thr
                165                 170                 175

Ala Glu Thr Thr Val Glu Ser Ile Gly Ala Leu Ser Lys Pro Gln Leu
            180                 185                 190

Gly Ile Ala Pro Thr His Asp Ile Thr Tyr Val Val Asp Lys Ile Lys
            195                 200                 205

Ala Ala Lys Leu Pro Val Ile Leu Leu Gly Met Arg Ala Ser Thr Asn
            210                 215                 220

Glu Val Thr Lys Ala Val Arg Lys Leu Ile Ala Asp Thr Glu Leu Pro
225                 230                 235                 240

Val Val Glu Thr Tyr Gln Ala Ala Gly Ala Ile Ser Arg Glu Leu Glu
                245                 250                 255

Asp His Phe Phe Gly Arg Val Gly Leu Phe Arg Asn Gln Pro Gly Asp
            260                 265                 270

Ile Leu Leu Glu Glu Ala Asp Leu Val Ile Ser Ile Gly Tyr Asp Pro
            275                 280                 285

Ile Glu Tyr Asp Pro Lys Phe Trp Asn Lys Leu Gly Asp Arg Thr Ile
            290                 295                 300

Ile His Leu Asp Asp His Gln Ala Asp Ile Asp His Ala Tyr Gln Pro
305                 310                 315                 320

Glu Arg Glu Leu Ile Gly Asp Ile Ala Leu Thr Val Asn Ser Ile Ala
                325                 330                 335

Glu Lys Leu Pro Lys Leu Val Leu Ser Thr Lys Ser Glu Ala Val Leu
                340                 345                 350

Glu Arg Leu Arg Ala Lys Leu Ser Glu Gln Ala Glu Val Pro Asn Arg
            355                 360                 365

Pro Ser Glu Gly Val Thr His Pro Leu Gln Val Ile Arg Thr Leu Arg
            370                 375                 380

Ser Leu Ile Ser Asp Asp Thr Thr Val Thr Cys Asp Ile Gly Ser His
385                 390                 395                 400

Ser Ile Trp Met Ala Arg Cys Phe Arg Ser Tyr Glu Pro Arg Arg Leu
                405                 410                 415

Leu Phe Ser Asn Gly Met Gln Thr Leu Gly Val Ala Leu Pro Trp Ala
                420                 425                 430

Ile Ala Ala Thr Leu Val Glu Pro Gly Lys Lys Val Val Ser Val Ser
            435                 440                 445
```

Gly Asp Gly Gly Phe Leu Phe Ser Ala Met Glu Leu Glu Thr Ala Val
        450                 455                 460

Arg Leu Asn Ser Pro Ile Val His Leu Val Trp Arg Asp Gly Thr Tyr
465                 470                 475                 480

Asp Met Val Ala Phe Gln Gln Met Met Lys Tyr Gly Arg Thr Ser Ala
                485                 490                 495

Thr Glu Phe Gly Asp Val Asp Leu Val Lys Tyr Ala Glu Ser Phe Gly
            500                 505                 510

Ala Leu Gly Leu Arg Val Asn Thr Pro Asp Glu Leu Glu Gly Val Leu
        515                 520                 525

Lys Glu Ala Leu Ala Ala Asp Gly Pro Val Ile Ile Asp Ile Pro Ile
    530                 535                 540

Asp Tyr Arg Asp Asn Ile Lys Leu Ser Glu Lys Leu Leu Pro Asn Gln
545                 550                 555                 560

Leu Asn

<210> SEQ ID NO 104
<211> LENGTH: 32
<212> TYPE: DNA
<213> ORGANISM: Artificial Sequence
<220> FEATURE:
<223> OTHER INFORMATION: Primer

<400> SEQUENCE: 104
atctctcgag attacatcag aaaagacaac aa                                    32

<210> SEQ ID NO 105
<211> LENGTH: 35
<212> TYPE: DNA
<213> ORGANISM: Artificial Sequence
<220> FEATURE:
<223> OTHER INFORMATION: Primer

<400> SEQUENCE: 105
cgatcccggg ttagtcatca ttttcatact gaatg                                 35

<210> SEQ ID NO 106
<211> LENGTH: 60
<212> TYPE: DNA
<213> ORGANISM: Artificial sequence
<220> FEATURE:
<223> OTHER INFORMATION: Primer

<400> SEQUENCE: 106
tcaaattatg gaggcgagaa acccgggatc gatggtacct aaatcggcat ttctagcatg     60

<210> SEQ ID NO 107
<211> LENGTH: 32
<212> TYPE: DNA
<213> ORGANISM: Artificial Sequence
<220> FEATURE:
<223> OTHER INFORMATION: Primer

<400> SEQUENCE: 107
atcctgtaca actttgtaat acctgagtct ac                                    32

<210> SEQ ID NO 108
<211> LENGTH: 52
<212> TYPE: DNA
<213> ORGANISM: Artificial sequence
<220> FEATURE:
<223> OTHER INFORMATION: Primer

```
<400> SEQUENCE: 108
atagcccggg atataggagg aatttttgta atgttgacca aggctaccaa ag          52

<210> SEQ ID NO 109
<211> LENGTH: 33
<212> TYPE: DNA
<213> ORGANISM: Artificial sequence
<220> FEATURE:
<223> OTHER INFORMATION: Primer

<400> SEQUENCE: 109
tttaggtacc ttataacgct ttcgtcttca tta                               33

<210> SEQ ID NO 110
<211> LENGTH: 24
<212> TYPE: DNA
<213> ORGANISM: Artificial sequence
<220> FEATURE:
<223> OTHER INFORMATION: Primer

<400> SEQUENCE: 110
ccaatgccta tctagctatg taag                                         24

<210> SEQ ID NO 111
<211> LENGTH: 20
<212> TYPE: DNA
<213> ORGANISM: Artificial sequence
<220> FEATURE:
<223> OTHER INFORMATION: Primer

<400> SEQUENCE: 111
agccttgttt caaccgatta                                              20

<210> SEQ ID NO 112
<211> LENGTH: 21
<212> TYPE: DNA
<213> ORGANISM: Artificial sequence
<220> FEATURE:
<223> OTHER INFORMATION: Primer

<400> SEQUENCE: 112
ttgttacttg attgcgactc g                                            21

<210> SEQ ID NO 113
<211> LENGTH: 21
<212> TYPE: DNA
<213> ORGANISM: Artificial sequence
<220> FEATURE:
<223> OTHER INFORMATION: Primer

<400> SEQUENCE: 113
gatccaaatc aaaagcaact g                                            21
```

US 9,080,179 B2

ENHANCED PYRUVATE TO 2,3-BUTANEDIOL CONVERSION IN LACTIC ACID BACTERIA

CROSS REFERENCE TO RELATED APPLICATIONS

This application is a continuation of U.S. application Ser. No. 12/569,136, filed Sep. 29, 2009, which is related to and claims the benefit of priority to U.S. Provisional Application No. 61/100,786, filed Sep. 29, 2008, each of which is herein incorporated by reference.

FIELD OF THE INVENTION

The invention relates to the field of industrial microbiology and the metabolism of lactic acid bacteria. More specifically, engineering lactic acid bacteria for a high flux from pyruvate to 2,3-butanediol allows increased production of 2,3-butanediol and compounds in pathways including 2,3-butanediol as an upstream substrate.

BACKGROUND OF THE INVENTION 2,3-butanediol, 2-butanone, and 2-butanol are important industrial chemicals. 2,3-butanediol may be used in the chemical synthesis of butene and butadiene, important industrial chemicals currently obtained from cracked petroleum, and esters of 2,3-butanediol may be used as plasticizers (Voloch et al. Fermentation Derived 2,3-Butanediol, in Comprehensive Biotechnology, Pergamon Press Ltd, England Vol 2, Section 3:933-947 (1986)). 2-Butanone, also referred to as methyl ethyl ketone (MEK), is a widely used solvent and is the most important commercially produced ketone, after acetone. It is used as a solvent for paints, resins, and adhesives, as well as a selective extractant, activator of oxidative reactions, and it can be chemically converted to 2-butanol by reacting with hydrogen in the presence of a catalyst (Nystrom, R. F. and Brown, W. G. (J. Am. Chem. Soc. (1947) 69:1198). Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Microorganisms may be engineered for expression of biosynthetic pathways for production of 2,3-butanediol, 2-butanone, and/or 2-butanol. US Patent Pub US20070292927A1 discloses the engineering of recombinant microorganisms for expression of a biosynthetic pathway having 2,3-butanediol and 2-butanone as intermediates and 2-butanol as the end product. The pathway initiates with cellular pyruvate. Thus production of 2,3-butanediol, 2-butanone, and 2-butanol is limited by the availability of pyruvate substrate flow from natural host pathways into this engineered biosynthetic pathway.

In lactic acid bacteria, a limited amount of 2,3-butanediol may be produced naturally, but the major pyruvate metabolic pathway is conversion to lactate through activity of lactate dehydrogenase (LDH). Metabolic engineering to redirect pyruvate from lactate to other products in lactic acid bacteria has had unpredictable results. Production of alanine in LDH-deficient *Lactococcus lactis* expressing alanine dehydrogenase was shown by Hols et al. (Nature Biotech. 17:588-592 (1999). However, production of ethanol in LDH-deficient *Lactobacillus plantarum* expressing pyruvate decarboxylase was very limited, with carbon flow not significantly improved toward ethanol and lactate still produced (Liu et al. (2006) J. Ind. Micro. Biotech. 33:1-7).

Where a lactic acid bacteria is the preferred host for the production of 2-butanol and 2-butanone, a need exists therefore for lactic acid bacteria to have a tightly regulated carbon flow from pyruvate to 2,3-butanediol. To date no bacteria has been engineered to produce this advantage and the art suggests that simply reducing the carbon flow from pyruvate to lactate via lactate dehydrogenase may not be sufficient. Applicants have solved the stated problem through the unexpected discovery that introduction of a heterologous polypeptide having butanediol dehydrogenase activity in combination with reduction in endogenous lactate dehydrogenase results in unpredictably high rates of conversion of pyruvate to down stream products and particularly 2,3-butanediol.

SUMMARY OF THE INVENTION

Provided herein are recombinant lactic acid bacterial cells comprising at least one gene encoding a heterologous polypeptide having butanediol dehydrogenase activity wherein the bacterial cell is substantially free of lactate dehydrogenase activity and wherein the cell produces 2,3-butanediol. In one embodiment, the bacterial cell comprises a disruption in at least one endogenous gene encoding a polypeptide having lactate dehydrogenase activity. In one embodiment, the cell is a member of a genus selected from the group consisting of *Lactococcus, Lactobacillus, Leuconostoc, Oenococcus, Pediococcus*, and *Streptococcus*.

In one embodiment, the cell comprises at least one genetic modification that reduces pyruvate formate lyase activity. In some embodiments, the genetic modification affects a gene encoding pyruvate formate lyase, a gene encoding pyruvate formate lyase activating enzyme, or both. In some embodiments, the gene encoding pyruvate formate lyase is selected from the group consisting of pfl, pflB1 and pfl B2 and the gene encoding formate C-acetyltransferase activating enzyme is selected from the group consisting of pflA, pflA1, and pflA2.

Also provided are embodiments wherein the cell produces a product selected from the group consisting of lactate, acetoin, ethanol, succinate, and formate. In some embodiments, 2,3-butanediol comprises at least about 49 Mol % of all products produced from pyruvate.

In some embodiments, the polypeptide having lactate dehydrogenase activity is encoded by a gene selected from the group consisting of ldhL, ldhD, ldhL1, and ldhL2.

In one embodiment, the lactic acid host cell is *Lactobacillus plantarum* and the polypeptide having lactate dehydrogenase activity has an amino acid sequence that has at least about 95% identity to a sequence selected from the group consisting of SEQ ID NO: 2, 4, and 6. In one embodiment, the lactic acid host cell is *Lactococcus lactis* and the polypeptide having lactate dehydrogenase activity has an amino acid sequence that has at least about 95% identity to the sequence as set forth in SEQ ID NO:20. In another embodiment, lactic acid host cell is *Leuconostoc mesenteroides* and the polypeptide having lactate dehydrogenase activity has an amino acid sequence that has at least about 95% identity to the sequence as set forth in SEQ ID NO:22. In another embodiment, the lactic acid host cell is *Streptococcus thermophilus* and the polypeptide having lactate dehydrogenase activity has an amino acid sequence that has at least about 95% identity to the sequence as set forth in SEQ ID NO:24. In another embodiment, the lactic acid host cell is *Pediococcus pentosaceus* and the polypeptide having lactate dehydrogenase activity has an amino acid sequence that has at least about 95% identity to a sequences selected from the group consisting of SEQ ID NO:26 and 28. In another embodiment, the lactic acid host cell is *Lactobacillus acidophilus* and the polypeptide having lactate dehydrogenase activity has an amino acid sequence that has at least about 95% identity to a sequence selected from the group consisting of SEQ ID NO:30, 32 and 34.

In one embodiment, the heterologous polypeptide having butanediol dehydrogenase activity has an amino acid sequence that has at least about 95% identity to a sequence selected from the group consisting of SEQ ID NO: 13, 64 and 66.

In one embodiment, the cell produces 2-butanone, and in one embodiment, the cell comprises a 2-butanone biosynthetic pathway. In one embodiment, the cell produces 2-butanol, and in one embodiment, the cell produces a 2-butanol biosynthetic pathway.

Also provided herein are methods for the production of 2-butanol comprising: providing a recombinant lactic acid bacterial cell comprising a 2-butanol biosynthetic pathway; and growing the bacterial cell of step (a) under conditions whereby 2-butanol is produced.

Also provided are methods for the production of 2-butanone comprising: providing a recombinant lactic acid bacterial cell comprising a 2-butanone biosynthetic pathway; and b) growing the bacterial cell of step (a) under conditions whereby 2-butanone is produced.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 1:
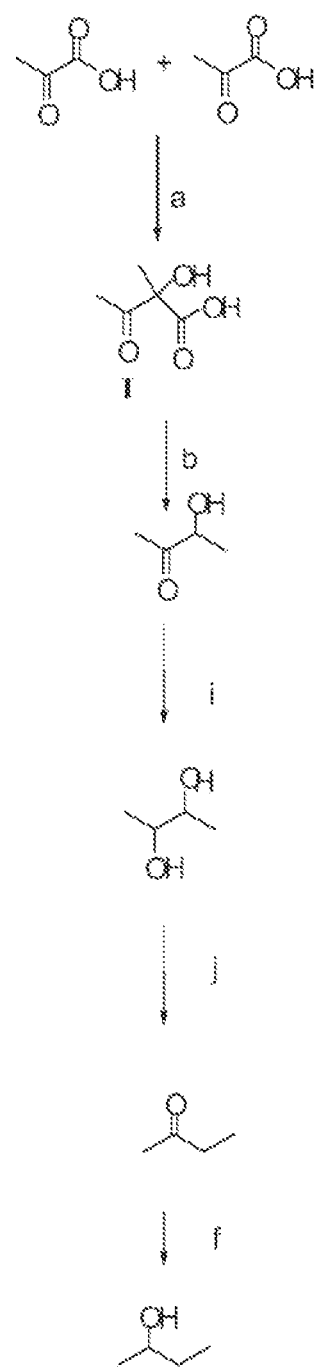
FIG. 1 shows a biosynthetic pathway for biosynthesis of 2,3-butanediol, 2-butanone, and 2-butanol.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID NOs of lactate dehydrogenase coding regions and proteins

| Organism and gene name | SEQ ID NO: nucleic acid | SEQ ID NO: amino acid |
|---|---|---|
| *Lactobacillus plantarum* ldhD | 1 | 2 |
| *Lactobacillus plantarum* ldhL1 | 3 | 4 |
| *Lactobacillus plantarum* ldhL2 | 5 | 6 |
| *Lactococcus lactis* ldhL | 19 | 20 |
| *Leuconostoc mesenteroides* ldhD | 21 | 22 |
| *Streptococcus thermophilus* ldhL | 23 | 24 |
| *Pediococcus pentosaceus* ldhD | 25 | 26 |
| *Pediococcus pentosaceus* ldhL | 27 | 28 |
| *Lactobacillus acidophilus* ldhL1 | 29 | 30 |
| *Lactobacillus acidophilus* ldhL2 | 31 | 32 |
| *Lactobacillus acidophilus* ldhD | 33 | 34 |

TABLE 2

SEQ ID NOs of butanediol dehydrogenase coding regions and proteins

| Description | SEQ ID NO: nucleic acid | SEQ ID NO: amino acid |
|---|---|---|
| budC, butanediol dehydrogenase from *Klebsiella pneumoniae* IAM1063 | 12 | 13 |
| butanediol dehydrogenase from *Bacillus cereus* | 63 | 64 |
| butB, butanediol dehydrogenase from *Lactococcus lactis* | 65 | 66 |

TABLE 3

SEQ ID NOs of pyruvate formate lyase and pyruvate formate lyase activating enzyme coding regions and proteins

| Organism and gene name | SEQ ID NO: nucleic acid | SEQ ID NO: amino acid |
|---|---|---|
| PflB1 from *Lactobacillus plantarum* | 69 | 70 |
| PflB2 from *Lactobacillus plantarum* | 71 | 72 |
| PflA1 from *Lactobacillus plantarum* | 73 | 74 |
| PflA2 from *Lactobacillus plantarum* | 75 | 76 |
| Pfl from *Lactococcus lactis* | 77 | 78 |
| PflA from *Lactococcus lactis* | 79 | 80 |
| Pfl from *Streptococcus thermophilus* | 81 | 82 |
| PflA from *Streptococcus thermophilus* | 83 | 84 |

TABLE 4

SEQ ID NOs of expression coding regions and proteins

| Description | SEQ ID NO: nucleic acid | SEQ ID NO: amino acid |
|---|---|---|
| *Achromobacter xylosoxidans* secondary alcohol dehydrogenase sadB | 9 | 10 |
| *Roseburia inulinivorans* butanediol dehydratase rdhtA | 15 | 16 |
| *Roseburia inulinivorans* butanediol dehydratase reactivase rdhtB | 17 | 18 |
| ALS from *Bacillus subtilis* | 85 | 86 |
| ALS from *Bacillus subtilis* coding region optimized for *Lactobacillus plantarum* | 87 | 86* |
| ALS from *Klebsiella pneumoniae* (budB) | 88 | 89 |
| ALS from *Lactococcus lactis* | 90 | 91 |
| ALS from *Staphylococcus aureus* | 92 | 93 |
| ALS from *Listeria monocytogenes* | 94 | 95 |
| ALS from *Streptococcus mutans* | 96 | 97 |
| ALS from *Streptococcus thermophilus* | 98 | 99 |

TABLE 4-continued

SEQ ID NOs of expression coding regions and proteins

| Description | SEQ ID NO: nucleic acid | SEQ ID NO: amino acid |
|---|---|---|
| ALS from *Vibrio angustum* | 100 | 101 |
| ALS from *Bacillus cereus* | 102 | 103 |

*same protein sequence encoded by native and optimized sequence

SEQ ID NO:7 is the nucleotide sequence of the coding region for orotidine-5'-phosphate decarboxylase from *L. plantarum*.

SEQ ID NO:8 is the nucleotide sequence of the *L. plantarum* ldhL1 promoter.

SEQ ID NO:11 is the nucleotide sequence of the *S. cerevisiae* FBA promoter.

SEQ ID NO:14 is the nucleotide sequence of the *S. cerevisiae* GPM1 promoter.

SEQ ID NOs:35-38 are plasmids pFP996, pFP996PldhL1, pFP996PldhL1-budC-sadB, and pFP996PldhL1-budC, respectively.

SEQ ID NOs:39-50, 52-62, and 104-113 are PCR, sequencing or cloning primers.

SEQ ID NO:51 is the nucleotide sequence of a ribosome binding site.

SEQ ID NO:67 is the sequence of a synthetic fragment containing coding regions for *Roseburia inulinivorans* $B_{12}$-independent diol dehydratase and reactivase.

DETAILED DESCRIPTION OF THE INVENTION

The present invention relates to recombinant lactic acid bacterial (LAB) cells that are genetically modified to have improved conversion of pyruvate, and in particular endogenous pyruvate, to 2,3-butanediol. The LAB cells express a heterologous butanediol dehydratase and are substantially free of lactate dehydrogenase activity. In addition, the present invention relates to methods of producing 2,3-butanediol, 2-butanone, or 2-butanol using the present genetically modified LAB cells. Production of these compounds in lactic acid bacteria will reduce the need for petrochemicals for their production as industrial chemicals for applications as solvents and/or extractants, and these compounds may replace fossil fuels either directly or as intermediates for further chemical synthesis of fossil fuel replacements.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "2-butanol biosynthetic pathway" refers to an enzyme pathway to produce 2-butanol from pyruvate.

The term "2-butanone biosynthetic pathway" refers to an enzyme pathway to produce 2-butanone from pyruvate The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (DNA: SEQ ID NO: 12, protein: SEQ ID NO: 13). (R)-specific butanediol dehydrogenases are known as EC 1.1.1.4 and are available, for example, from *Bacillus cereus* (DNA: SEQ ID NO:63, protein: SEQ ID NO:64), and *Lactococcus lactis* (DNA: SEQ ID NO:65, protein: SEQ ID NO:66).

The term "lactate dehydrogenase" refers to a polypeptide (or polypeptides) having an enzyme activity that catalyzes the conversion of pyruvate to lactate. Lactate dehydrogenases are known as EC 1.1.1.27 (L-lactate dehydrogenase) or EC 1.1.1.28 (D-lactate dehydrogenase) and are further described herein.

The term "substantially free" when used in reference to the presence or absence of lactate dehydrogenase enzyme activity means that the level of the enzyme is substantially less than that of the same enzyme in the wild-type host, where less than 50% of the wild-type level is preferred and less than about 90% of the wild-type level is most preferred. The reduced level of enzyme activity may be attributable to genetic modification genes encoding this enzyme such that expression levels of the enzyme are reduced.

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "additional electron sink" refers to an electron sink or production of an electron sink that is not included in the biosynthetic pathway for the desired product.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Also a foreign gene can comprise native genes inserted into a non-native organism, or chimeric genes. A "transgene" is a gene that has been introduced into the genome by a transformation procedure.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2$^{nd}$* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: N J (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*. 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci.* 8:189-191(1992), Thompson, J. D., Higgins, D. G., and Gibson T. J. (1994) *Nuc. Acid Res.* 22: 4673 4680) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mish.); and 5.) the FASTA program incorporating the Smith-Waterman algorithm (W. R. Pearson, *Comput. Methods Genome Res., [Proc. Int. Symp.]* (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

High Flux of Pyruvate to 2,3-Butanediol in Lactic Acid Bacteria

The present invention discloses that a high proportion of pyruvate may be converted to 2,3-butanediol in lactic acid bacterial cells when the cells are genetically modified to be substantially free of lactate dehydrogenase activity and genetically modified to express heterologous polypeptides having butanediol dehydrogenase activity.

Figure 4:
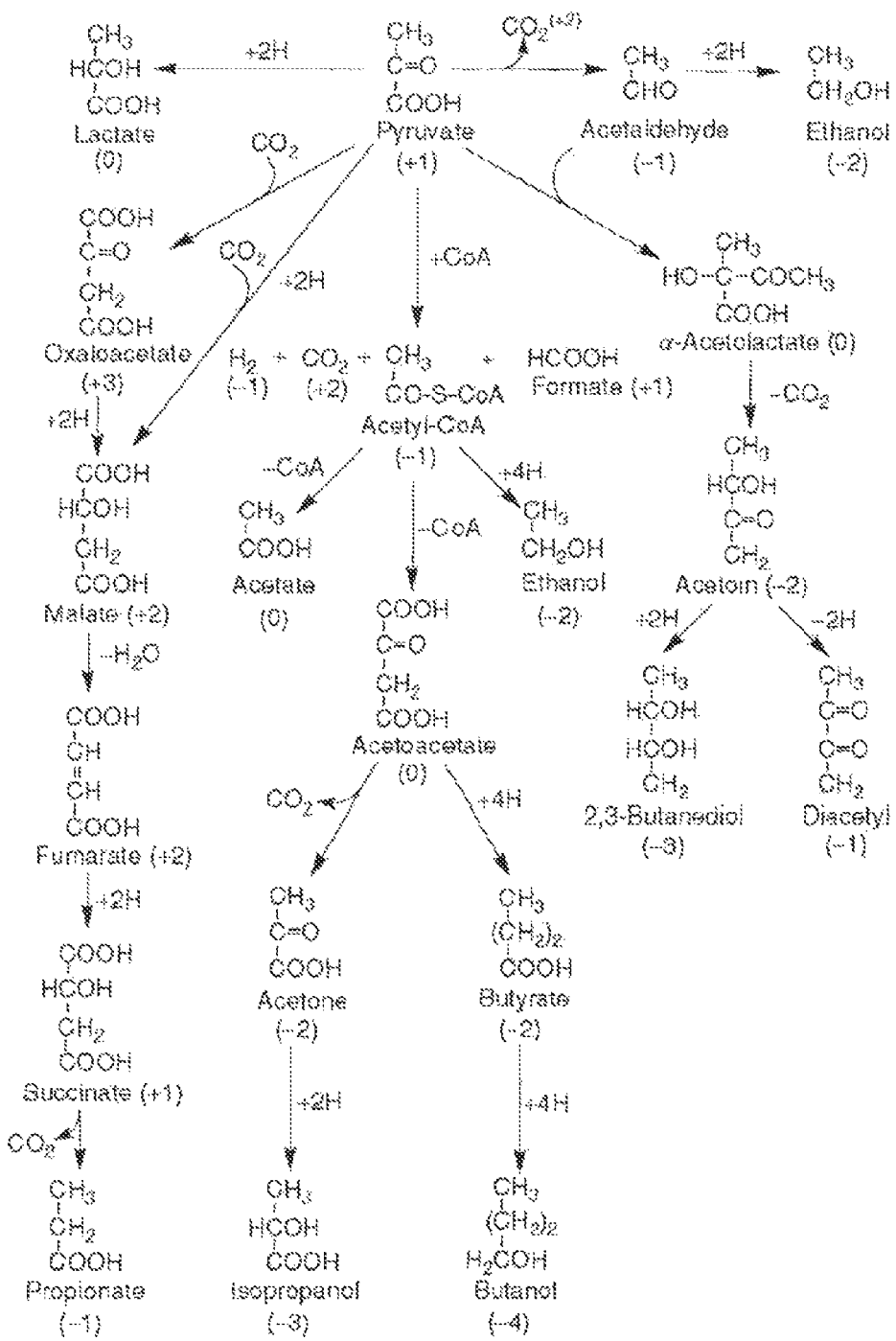
FIG. 4 illustrates common lactate fermentation pathways in lactic acid bacteria.

Lactic acid bacteria are well characterized and have been used commercially for many years for the production of a wide variety of products. A number of fermentation pathways exist in nature for the metabolism of sugars though pyruvate (see FIG. 4), however lactic acid bacteria have systems that favor the conversion of pyruvate to lactic acid via lactic acid dehydrogenase. It is an object of the present invention to maximize carbon flow from pyruvate to 2,3-butanediol for the production of 2-butanol and 2-butanone (FIGS. 4, and 1).

Surprisingly, as described herein, it was found that the pathway modifications of the present invention resulted in a lactic acid host cell that, instead of producing mainly lactate with a small amount of acetoin as in cells without these genetic modifications, the modified cells produced 2,3-butanediol, ethanol, succinate, formate, lactate, and acetoin products. The amount of 2,3-butanediol produced is at least about 49 Mol % of the total of these 6 products At least about 0.4 gram of 2,3-butanediol may be produced per gram of glucose consumed.

2,3-butanediol is made from pyruvate through steps of pyruvate conversion to acetolactate, acetolactate conversion to acetoin, and acetoin conversion to 2,3-butanediol. This biosynthetic pathway is the first three steps (a, b, and i) of the pathway shown in FIG. 1, which is described further below. Activities performing the first and second conversions may be provided by endogenous host enzymes as exemplified herein, or may be provided by expression of heterologous enzymes as described further below.

Production of 2,3-butanediol may be achieved in cells that are lactic acid bacteria (LAB), due to the redirection of carbon flow from lactic acid production. LAB which may be host cells in the present disclosure include, but are not limited to, *Lactococcus, Lactobacillus, Leuconostoc, Oenococcus, Pediococcus*, and *Streptococcus*.

In addition, it was determined that it is not necessary to provide an additional electron sink to balance redox equivalents to achieve the described flux from pyruvate to 2,3-butanediol. As lactate is the major end product for *Lactobacillus plantarum*, the NAD-dependent lactate dehydrogenases are major contributors to balancing redox equivalents. In the absence of the lactate dehydrogenases, it was expected that an additional electron sink would be needed to help balance redox. However, Applicants found that the co-production of ethanol and succinate by native enzymes was sufficient to balance redox equivalents to obtain the flux described herein, such that an additional electron sink was not needed.

Reduced Lactate Dehydrogenase Activity

Endogenous lactate dehydrogenase activity in lactic acid bacteria (LAB) converts pyruvate to lactate. LAB may have one or more genes, typically one, two or three genes, encoding lactate dehydrogenase. For example, *Lactobacillus plantarum* has three genes encoding lactate dehydrogenase which are named ldhL2 (protein SEQ ID NO:6, coding region SEQ ID NO:5), ldhD (protein SEQ ID NO:2, coding region SEQ ID NO:1), and ldhL1 (protein SEQ ID NO:4, coding region SEQ ID NO:3). *Lactococcus lactis* has one gene encoding lactate dehydrogenase which is named ldhL (protein SEQ ID NO:20, coding region SEQ ID NO:19), and *Pediococcus pentosaceus* has two genes named ldhD (protein SEQ ID NO:26, coding region SEQ ID NO:25) and ldhL (protein SEQ ID NO:28, coding region SEQ ID NO:27).

In the present LAB strains, lactate dehydrogenase activity is reduced so that the cells are substantially free of lactate dehydrogenase activity. Genetic modification is made in at least one gene encoding lactate dehydrogenase to reduce activity. When more than one lactate dehydrogenase gene is active under the growth conditions to be used, each of these active genes may be modified to reduce expression and thereby reduce or eliminate lactate dehydrogenase activity. For example, in *L. plantarum* ldhL1 and ldhD genes are modified. It is not necessary to modify the third gene, ldhL2, for growth in typical conditions as this gene appears to be inactive in these conditions. Typically, expression of one or more genes encoding lactate dehydrogenase is disrupted to reduce expressed enzyme activity. Examples of LAB lactate dehydrogenase genes that may be targeted for disruption are represented by the coding regions of SEQ ID NOs:1, 3, 5, 19, 21, 23, 25, 27, 29, 31, and 33 listed in Table 1. Other target genes, such as those encoding lactate dehydrogenase proteins having at least about 80-85%, 85%-90%, 90%-95%, or at least about 98% sequence identity to the lactate dehydrogenases of SEQ ID NOs:2, 4, 6, 20, 22 24, 26, 28, 30, 32, and 34 listed in Table 1 may be identified in the literature and using bioinformatics approaches, as is well known to one of ordinary skill in the art, since lactate dehydrogenases are well known. Typically BLAST (described above) searching of publicly available databases with known lactate dehydrogenase amino acid sequences, such as those provided herein, is used to identify lactate dehydrogenases, and their encoding sequences, that may be targets for disruption to reduce lactate dehydrogenase activity. Identities are based on the Clustal W method of alignment using the default parameters of GAP PENALTY=10, GAP LENGTH PENALTY=0.1, and Gonnet 250 series of protein weight matrix.

Additionally, the sequences described herein or those recited in the art may be used to identify other homologs in nature in other LAB strains. For example each of the lactate dehydrogenase encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the lactate dehydrogenase encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described lactate dehydrogenase encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In the present LAB strains, at least one modification is engineered that results in cells substantially free of lactate dehydrogenase activity. This may be accomplished by eliminating expression of at least one endogenous gene encoding lactate dehydrogenase. Any genetic modification method known by one skilled in the art for reducing the expression of a protein may be used to alter lactate dehydrogenase expression. Methods include, but are not limited to, deletion of the entire or a portion of the lactate dehydrogenase encoding gene, inserting a DNA fragment into the lactate dehydrogenase encoding gene (in either the promoter or coding region) so that the encoded protein cannot be expressed, introducing a mutation into the lactate dehydrogenase coding region which adds a stop codon or frame shift such that a functional protein is not expressed, and introducing one or more mutations into the lactate dehydrogenase coding region to alter amino acids so that a non-functional protein is expressed. In addition lactate dehydrogenase expression may be blocked by expression of an antisense RNA or an interfering RNA, and constructs may be introduced that result in cosuppression. All of these methods may be readily practiced by one skilled in the art making use of the known lactate dehydrogenase encoding sequences such as those of SEQ ID NOs: 1, 3, 5, 19, 21, 23, 25, 27, 29, 31, and 33.

For some methods genomic DNA sequences that surround a lactate dehydrogenase encoding sequence are useful, such as for homologous recombination-based methods. These sequences may be available from genome sequencing projects such as for *Lactobacillus plantarum*, which is available through the National Center for Biotechnology Information (NCBI) database, with Genbank™ identification gi|28376974|ref|NC_004567.1|[28376974]. Adjacent genomic DNA sequences may also be obtained by sequencing outward from a lactate dehydrogenase coding sequence using primers within the coding sequence, as well known to one skilled in the art.

A particularly suitable method for creating a genetically modified LAB strain substantially free of lactate dehydrogenase activity, as exemplified herein in Example 1, is using homologous recombination mediated by lactate dehydrogenase coding region flanking DNA sequences to delete the entire gene. The flanking sequences are cloned adjacent to each other so that a double crossover event using these flanking sequences deletes the lactate dehydrogenase coding region.

Expression of Heterologous Butanediol Dehydrogenase Activity

Lactic acid bacteria may naturally have a low amount of 2,3-butanediol synthesis, which may vary depending on the growth conditions. In the present invention, expression of heterologous butanediol dehydrogenase activity provides a pathway to 2,3-butanediol synthesis that successfully competes with other pathways that use pyruvate as an initial substrate, in the absence of lactate dehydrogenase activity. Heterologous butanediol dehydrogenase activity is expressed in a LAB cell that is substantially free of lactate dehydrogenase activity as described above.

Butanediol dehydrogenase enzymes are well-known and are described in the definitions above. The skilled person will appreciate that polypeptides having butanediol dehydrogenase activity isolated from a variety of sources will be useful in the present invention independent of sequence homology. Some examples of suitable butanediol dehydrogenase enzymes include, but are not limited to, those from *Klebsiella pneumoniae* (DNA: SEQ ID NO:12, protein: SEQ ID NO:13), *Bacillus cereus* (DNA: SEQ ID NO:63, protein: SEQ ID NO:64), and *Lactococcus lactis* (DNA: SEQ ID NO:65, protein: SEQ ID NO:66).

Because butanediol dehydrogenases are well known, and because of the prevalence of genomic sequencing, suitable butanediol dehydrogenases may be readily identified by one skilled in the art on the basis of sequence similarity using bioinformatics approaches. Typically BLAST (described above) searching of publicly available databases with known butanediol dehydrogenase amino acid sequences, such as those provided herein, is used to identify butanediol dehydrogenases, and their encoding sequences, that may be used in the present strains.

Examples of genes encoding butanediol dehydrogenase, which may be used to provide heterologous expression of butanediol dehydrogenase activity in the present LAB, have SEQ ID NOs: 12, 63, and 64 and are listed in Table 2. Additional butanediol dehydrogenase encoding genes that may be used for heterologous expression in LAB may be identified in the literature and in bioinformatics databases well known to the skilled person. Encoding sequences for butanediol dehydrogenase proteins having amino acid sequence identities of at least about 70-75%, 75%-80%, 80-85%, 85%-90%, 90%-95%, or 98% sequence identity to any of the butanediol dehydrogenase proteins of SEQ ID NOs:13, 64 and 66 listed in Table 2 may be expressed in the present strains. Identities are based on the Clustal W method of alignment using the default parameters of GAP PENALTY=10, GAP LENGTH PENALTY=0.1, and Gonnet 250 series of protein weight matrix.

Additionally, the sequences encoding butanediol dehydrogenases described herein or those recited in the art may be used to identify other homologs in nature. For example each of the butanediol dehydrogenase encoding nucleic acid fragments described herein may be used to isolate genes encoding homologous proteins. Isolation of homologous genes using sequence-dependent protocols is well known in the art, as described above for lactate dehydrogenase encoding nucleic acid fragments.

Expression of heterologous butanediol dehydrogenase is achieved by transforming suitable host cells with a sequence encoding a butanediol dehydrogenase protein. Typically the coding sequence is part of a chimeric gene used for transformation, which includes a promoter operably linked to the coding sequence as well as a ribosome binding site and a termination control region. A chimeric gene is heterologous even if it includes the coding sequence for a butanediol dehydrogenase from the host cell for transformation, if the coding sequence is combined with regulatory sequences that are not native to the natural gene encoding butanediol dehydrogenase.

Codons may be optimized for expression based on codon usage in the selected host, as is known to one skilled in the art. Vectors useful for the transformation of a variety of host cells are common and described in the literature. Typically the vector contains a selectable marker and sequences allowing autonomous replication or chromosomal integration in the desired host. In addition, suitable vectors may comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

Initiation control regions or promoters, which are useful to drive expression of a butanediol dehydrogenase coding region in LAB are familiar to those skilled in the art. Some examples include the amy, apr, and npr promoters; nisA promoter (useful for expression Gram-positive bacteria (Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). In addition, the ldhL1 and fabZ1 promoters of *L plantarum* are useful for expression of chimeric genes in LAB. The fabZ1 promoter directs transcription of an operon with the first gene, fabZ1, encoding (3R)-hydroxymyristoyl-[acyl carrier protein] dehydratase.

Termination control regions may also be derived from various genes, typically from genes native to the preferred hosts. Optionally, a termination site may be unnecessary, however, it is most preferred if included.

Vectors useful in LAB include vectors having two origins of replication and two selectable markers which allow for replication and selection in both *Escherichia coli* and LAB. An example is pFP996, the sequence of which is provided as SEQ ID NO:35, which is useful in *L. plantarum* and other LAB. Many plasmids and vectors used in the transformation of *Bacillus subtilis* and *Streptococcus* may be used generally for LAB. Non-limiting examples of suitable vectors include pAMβ1 and derivatives thereof (Renault et al., *Gene* 183: 175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. *Appl. Environ. Microbiol.* 2005 March; 71(3): 1223-1230).

Vectors may be introduced into a host cell using methods known in the art, such as electroporation (Cruz-Rodz et al. *Molecular Genetics and Genomics* 224:1252-154 (1990), Bringel, et al. *Appl. Microbiol. Biotechnol.* 33: 664-670 (1990), Alegre et al., *FEMS Microbiology letters* 241:73-77 (2004)), and conjugation (Shrago et al., *Appl. Environ. Microbiol.* 52:574-576 (1986)). A chimeric butanediol dehydrogenase gene can also be integrated into the chromosome of LAB using integration vectors (Hols et al., *Appl. Environ. Microbiol.* 60:1401-1403 (1990), Jang et al., *Micro. Lett.* 24:191-195 (2003)).

Reducing Pyruvate Formate Lyase Activity

In addition to the modifications described above with respect to lactate dehydrogenase and butanediol dehydrogenase in the present cells, optionally these cells may further have at least one modification that reduces endogenous pyruvate formate lyase activity. Pyruvate formate lyase activity converts pyruvate to formate. Activity of pyruvate formate lyase in the cell may be reduced or eliminated. Preferably the activity is eliminated.

For expression of pyruvate formate lyase activity a gene encoding pyruvate formate lyase (pfl) and a gene encoding pyruvate formate lyase activating enzyme are required. To reduce pyruvate formate lyase activity a modification may be made in either or both of these genes. There may be one or more genes encoding each of pyruvate formate lyase and pyruvate formate lyase activating enzyme in a particular strain of LAB. For example, *Lactobacillus plantarum* WCFS1 contains two pfl genes (pflB1: coding region SEQ ID NO:69, protein SEQ ID NO:70; and pflB2: coding region SEQ ID NO:71, protein SEQ ID NO:72) and two pfl activating enzyme genes (pflA1: coding region SEQ ID NO:73, protein SEQ ID NO:74; and pflA2: coding region SEQ ID NO:75, protein SEQ ID NO:76), *Lactobacillus plantarum* PN0512 only contains one pfl gene (pflB2) and one pfl activating enzyme gene (pflA2). In one embodiment, expression is reduced for all pfl encoding genes that are active in a production host cell under the desired production conditions and/or for all pfl activating enzyme encoding genes that are active in a production host cell under the desired production conditions.

Examples of pfl genes that may be modified to reduce pyruvate formate lyase activity are represented by the coding regions of SEQ ID NOs: 39, 41, 47, and 51. Other target genes for modification include those encoding pyruvate formate lyase proteins having SEQ ID NOs:40, 42, 48, and 52 and those encoding a protein having at least about 80-85%, 85%-90%, 90%-95%, or at least about 96%, 97%, 98%, or 99% sequence identity to one of these proteins, which may be identified in the literature and using bioinformatics approaches, as is well known to the skilled person as described above for lactate dehydrogenase proteins. Additionally, the sequences described herein or those recited in the art may be used to identify other homologs in nature as described above.

Examples of pfl activating enzyme genes that may be modified to reduce pyruvate formate lyase activity are represented by the coding regions of SEQ ID NOs:73, 75, 79, and 83. Other target genes for modification include those encoding pyruvate formate lyase activating enzyme proteins having SEQ ID NOs:74, 76, 80, 84 and those encoding a protein having at least about 80-85%, 85%-90%, 90%-95%, or at least about 96%, 97%, 98%, or 99% sequence identity to one of these proteins, which may be identified in the literature and using bioinformatics approaches, as is well known to the skilled person as described above for lactate dehydrogenase proteins. Additionally, the sequences described herein or those recited in the art may be used to identify other homologs in nature as described above.

Any genetic modification method known by one skilled in the art for reducing the expression of a protein may be used to alter pyruvate formate lyase activity. Methods to reduce or eliminate expression of the pyruvate formate lyase and/or pyruvate formate lyase activating enzyme genes include, but are not limited to, deletion of the entire or a portion of the gene, inserting a DNA fragment into the gene (in either the promoter or coding region) so that the encoded protein cannot be expressed or has reduced expression, introducing a mutation into the coding region which adds a stop codon or frame shift such that a functional protein is not expressed, and introducing one or more mutations into the coding region to alter amino acids so that a non-functional or reduced-functional protein is expressed. In addition expression from the target gene may be partially or substantially blocked by expression of an antisense RNA or an interfering RNA, and constructs may be introduced that result in cosuppression.

Product Biosynthesis in LAB Engineered for High Flux of Pyruvate to 2,3-Butanediol 2,3-butanediol and any product that has 2,3-butanediol as a pathway intermediate may be produced with greater effectiveness (such as greater rate, titer, yield, and/or efficiency thereof) in a LAB cell disclosed herein having high flux of pyruvate to 2,3-butanediol. Such products include, but are not limited to, 2,3-butanediol, 2-butanone, and 2-butanol.

A biosynthetic pathway for synthesis of 2,3-butanediol, 2-butanone and 2-butanol is disclosed in US Patent Pub No. US20070292927A1, which is herein incorporated by reference. A diagram of the disclosed 2,3-butanediol, 2-butanone and 2-butanol biosynthetic pathway is provided in FIG. 1 therein. 2,3-butanediol is the product of the first three steps, which are listed below. 2-Butanone is the product made when the last depicted step of converting 2-butanone to 2-butanol is omitted. Production of 2-butanone or 2-butanol in a strain disclosed herein benefits from increased production of 2,3-butanediol. As described in US Patent Pub No. US20070292927A1, steps in the biosynthetic pathway include conversion of:

pyruvate to acetolactate (see FIG. 1, step a therein) as catalyzed for example by acetolactate synthase (ALS) known by the EC number 2.2.1.69;
acetolactate to acetoin (see FIG. 1, step b therein) as catalyzed for example by acetolactate decarboxylase;
acetoin to 2,3-butanediol (see FIG. 2, step i therein) as catalyzed for example by butanediol dehydrogenase;
2,3-butanediol to 2-butanone (see FIG. 2, step j therein) as catalyzed for example by diol dehydratase or glycerol dehydratase; and
2-butanone to 2-butanol (see FIG. 2, step f therein) as catalyzed for example by butanol dehydrogenase.

Genes that may be used to engineer expression of these enzymes are described in US Patent Pub No. 20070292927A1. Alternatively endogenous enzymes in LAB may perform some pathway steps, such as acetolactate synthase and acetolactate decarboxylase. The use in this pathway of the butanediol dehydratase from *Roseburia inulinivorans*, RdhtA, (protein SEQ ID NO:16, coding region SEQ ID NO:15) is disclosed in US Patent Pub No. US 20090155870A1. This enzyme is used in conjunction with the butanediol dehydratase reactivase from *Roseburia inulinivorans*, RdhtB, (protein SEQ ID NO:18, coding region SEQ ID NO:17). This butanediol dehydratase is desired in many hosts because it does not require coenzyme $B_{12}$.

Some representative ALS enzymes that may be used include those encoded by alsS of *Bacillus* and budB of *Klebsiella* (Gollop et al., *J. Bacteriol.* 172(6):3444-3449 (1990); Holtzclaw et al., *J. Bacteriol.* 121(3):917-922 (1975)). ALS from *Bacillus subtilis* (DNA: SEQ ID NO:85; protein: SEQ ID NO:86), from *Klebsiella pneumoniae* (DNA: SEQ ID NO:88; protein: SEQ ID NO:89), and from *Lactococcus lactis* (DNA: SEQ ID NO:90; protein: SEQ ID NO:91) are provided herein. Additional Als coding regions and encoded proteins that may be used include those from *Staphylococcus aureus* (DNA: SEQ ID NO:92; protein: SEQ ID NO:93), *Listeria monocytogenes* (DNA: SEQ ID NO:94; protein: SEQ ID NO:95), *Streptococcus mutans* (DNA: SEQ ID NO:96; protein: SEQ ID NO:97), *Streptococcus thermophilus* (DNA: SEQ ID NO:98; protein: SEQ ID NO:99), *Vibrio angustum* (DNA: SEQ ID NO:100; protein: SEQ ID NO:101), and *Bacillus cereus* (DNA: SEQ ID NO:102; protein: SEQ ID NO:103). Any Als gene that encodes an acetolactate synthase having at least about 80-85%, 85%-90%, 90%-95%, or at least about 96%, 97%, or 98% sequence identity to any one of those with SEQ ID NOs:86, 89, 91, 93, 95, 97, 99, 101, or 103 that converts pyruvate to acetolactate may be used. Identities are based on the Clustal W method of alignment using the default parameters of GAP PENALTY=10, GAP LENGTH PENALTY=0.1, and Gonnet 250 series of protein weight matrix.

Additionally, U.S. patent application Ser. No. 12/477,942 provides a phylogenetic tree depicting acetolactate synthases that are the 100 closest neighbors of the *B. subtilis* AlsS sequence, any of which may be used. Additional Als sequences that may be used in the present strains may be identified in the literature and in bioinformatics databases as is well known to the skilled person. Identification of coding and/or protein sequences using bioinformatics is typically through BLAST (described above) searching of publicly available databases with known Als encoding sequences or encoded amino acid sequences, such as those provided herein. Identities are based on the Clustal W method of alignment as specified above. Additionally, the sequences listed herein or those recited in the art may be used to identify other homologs in nature as described above.

Useful for the last step of converting 2-butanone to 2-butanol is a new butanol dehydrogenase isolated from an environmental isolate of a bacterium identified as *Achromobacter xylosoxidans* that is disclosed in U.S. patent application Ser. No. 12/430,356 (DNA: SEQ ID NO:9, protein SEQ ID NO:10).

Chimeric genes that include the coding regions for enzymes of the pathway, or desired portion of the pathway, may be constructed and used in vectors as described above for butanediol dehydrogenase, and as disclosed in US 20070292927A1, to engineer 2,3-butanediol, 2-butanone or 2-butanol producing cells.

Growth for Production

Recombinant LAB cells disclosed herein may be used for fermentation production of 2,3-butanediol, 2-butanol or 2-butanone. The recombinant cells are grown in fermentation media which contains suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

Although it is contemplated that all of the above mentioned carbon substrates and mixtures thereof are suitable in the present invention, preferred carbon substrates are glucose, fructose, and sucrose, or mixtures of monosaccharides including C5 sugars such as xylose and arabinose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Pub No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of the enzymatic pathway necessary for 2,3-butanediol, 2-butanol or 2-butanone production. Typically cells are grown at a temperature in the range of about 25° C. to about 40° C. in an appropriate medium. Suitable growth media are common commercially prepared media such as Bacto *Lactobacilli* MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

2,3-butanediol, 2-butanol or 2-butanone may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

2,3-butanediol, 2-butanol or 2-butanone may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of 2,3-butanediol, 2-butanol or 2-butanone may be practiced using either batch, fed-batch or continuous processes and that any known mode of fermentation would be suitable. Additionally, it is contemplated that cells may be immobilized on a substrate as whole cell catalysts and subjected to fermentation conditions for 2,3-butanediol, 2-butanol or 2-butanone production.

Methods for 2,3-Butanediol, 2-Butanol or 2-Butanone Isolation from the Fermentation Medium Bioproduced 2,3-butanediol, 2-butanol or 2-butanone may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol 2,3-butanediol, 2-butanol or 2-butanone may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec' means second(s), "μl" means microliter(s), "ml" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "rpm" means revolutions per minute, "w/v" means weight/volume, "OD" means optical density, and "OD600" means optical density measured at a wavelength of 600 nm.

General Methods:

Standard recombinant DNA and molecular cloning techniques used in the Examples are well known in the art and are described by Sambrook, J., Fritsch, E. F. and Maniatis, T., Molecular Cloning: A Laboratory Manual, Cold Spring Harbor Laboratory Press, Cold Spring Harbor, N.Y., 1989, by T. J. Silhavy, M. L. Bennan, and L. W. Enquist, Experiments with Gene Fusions, Cold Spring Harbor Laboratory, Cold Spring Harbor, N.Y., 1984, and by Ausubel, F. M. et al., Current Protocols in Molecular Biology, Greene Publishing Assoc. and Wiley-Interscience, N.Y., 1987. Additional methods used in the Examples are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992).

Example 1

Construction of the *Lactobacillus Plantarum* PN0512 ΔldhDΔldhL1 Strain PNP0001

The purpose of this example is to describe the construction of a *Lactobacillus plantarum* PN0512 strain that is deleted for the two genes that encode the major lactate dehydrogenases. The major end product of fermentation in *Lactobacillus plantarum* is lactic acid. Pyruvate is converted to lactate by the action of two lactate dehydrogenases encoded by the ldhD and ldhL1 genes. A double deletion of ldhD and ldhL1 was made in *Lactobacillus plantarum* PN0512 (ATCC strain #PTA-7727).

Gene knockouts were constructed using a process based on a two-step homologous recombination procedure to yield unmarked gene deletions (Ferain et al., 1994, *J. Bact.* 176: 596). The procedure utilized a shuttle vector, pFP996 (SEQ ID NO:35). pFP996 is a shuttle vector for gram-positive bacteria. It can replicate in both *E. coli* and gram-positive bacteria. It contains the origins of replication from pBR322 (nucleotides #2628 to 5323) and pE194 (nucleotides #43 to 2627). pE194 is a small plasmid isolated originally from a gram positive bacterium, *Staphylococcus aureus* (Horinouchi and Weisblum J. Bacteriol. (1982) 150(2):804-814). In pFP996, the multiple cloning sites (nucleotides #1 to 50) contain restriction sites for EcoRI, BglII, XhoI, SmaI, ClaI, KpnI, and HindIII. There are two antibiotic resistance markers; one is for resistance to ampicillin and the other for resistance to erythromycin. For selection purposes, ampicillin was used for transformation in *E. coli* and erythromycin was used for selection in *L. plantarum*.

Two segments of DNA, each containing 900 to 1200 bp of sequence either upstream or downstream of the intended deletion, were cloned into the plasmid to provide the regions of homology for the two genetic cross-overs. Cells were grown for an extended number of generations (30-50) to allow for the cross-over events to occur. The initial cross-over (single cross-over) integrated the plasmid into the chromosome by homologous recombination through one of the two homology regions on the plasmid. The second cross-over (double cross-over) event yielded either the wild-type sequence or the intended gene deletion. A cross-over between the sequences that led to the initial integration event would yield the wild-type sequence, while a cross-over between the other regions of homology would yield the desired deletion. The second cross-over event was screened for by antibiotic sensitivity. Single and double cross-over events were analyzed by PCR and DNA sequencing.

All restriction enzymes, DNA modifying enzymes and Phusion High-Fidelity PCR Master Mix were purchased from NEB Inc. (Ipswich, Mass.). PCR SuperMix and Platinum PCR SuperMix High Fidelity were purchased from Invitrogen Corp (Carlsbad, Calif.). DNA fragments were gel purified using Zymoclean™ Gel DNA Recovery Kit (Zymo Research Corp, Orange, Calif.) or Qiaquick PCR Purification Kit (Qiagen Inc., Valencia, Calif.). Plasmid DNA was prepared with QIAprep Spin Miniprep Kit (Qiagen Inc., Valencia, Calif.). Oligoucleotides were synthesized by Sigma-Genosys (Woodlands, Tex.) or Invitrogen Corp (Carlsbad, Calif.). *L. plantarum* PN0512 genomic DNA was prepared with MasterPure DNA Purification Kit (Epicentre, Madison, Wis.).

*Lactobacillus plantarum* PN0512 was transformed by the following procedure: 5 ml of *Lactobacilli* MRS medium (Accumedia, Neogen Corporation, Lansing, Mich.) containing 1% glycine (Sigma-Aldrich, St. Louis, Mo.) was inoculated with PN0512 cells and grown overnight at 30° C. 100 ml MRS medium with 1% glycine was inoculated with overnight culture to an OD600 of 0.1 and grown to an OD600 of 0.7 at 30° C. Cells were harvested at 3700×g for 8 min at 4° C., washed with 100 ml cold 1 mM $MgCl_2$ (Sigma-Aldrich, St. Louis, Mo.), centrifuged at 3700×g for 8 min at 4° C., washed with 100 ml cold 30% PEG-1000 (Sigma-Aldrich, St. Louis, Mo.), recentrifuged at 3700×g for 20 min at 4° C., then resuspended in 1 ml cold 30% PEG-1000. 60 µl cells were mixed with ~100 ng plasmid DNA in a cold 1 mm gap gap electroporation cuvette and electroporated in a BioRad Gene Pulser (Hercules, Calif.) at 1.7 kV, 25 µF, and 400Ω. Cells were resuspended in 1 ml MRS medium containing 500 mM sucrose (Sigma-Aldrich, St. Louis, Mo.) and 100 mM $MgCl_2$, incubated at 30° C. for 2 hrs, plated on MRS medium plates containing 1 or 2 µg/ml of erythromycin (Sigma-Aldrich, St. Louis, Mo.), then placed in an anaerobic box containing a Pack-Anaero sachet (Mitsubishi Gas Chemical Co., Tokyo, Japan) and incubated at 30° C.

ΔldhD

The knockout cassette to delete the ldhD gene was created by amplifying from PN0512 genomic DNA an upstream flanking region with primers Top D F1 (SEQ ID NO:39) containing an EcoRI site and Top D R1 (SEQ ID NO:40). The downstream homology region including part of the coding sequence of ldhD was amplified with primers Bot D F2 (SEQ ID NO:41) and Bot D R2 (SEQ ID NO:42) containing an XhoI site. The two homology regions were joined by PCR SOE as follows. The 0.9 kbp upstream and downstream PCR products were gel-purified. The PCR products were mixed in equal amounts in a PCR reaction and re-amplified with primers Top D F1 and Bot D R2. The final 1.8 kbp PCR product was gel-purified and TOPO cloned into pCR4BluntII-TOPO (Invitrogen) to create vector pCRBluntII::ldhD. To create the integration vector carrying the internal deletion of the ldhD gene, pFP996 was digested with EcoRI and XhoI and the 5311-bp fragment gel-purified. Vector pCRBluntII::ldhD was digested with EcoRI and XhoI and the 1.8 kbp fragment gel-purified. The ldhD knockout cassette and vector were ligated using T4 DNA ligase, resulting in vector pFP996::ldhD ko.

Electrocompetent *Lactobacillus plantarum* PN0512 cells were prepared, transformed with pFP996::ldhD ko, and plated on MRS containing 1 µg/ml of erythromycin. To obtain the single-crossover event (sco), transformants were passaged for approximately 50 generations in MRS medium at 37° C. After growth, aliquots were plated for single colonies on MRS containing 1 µg/ml of erythromycin. The erythromycin-resistant colonies were screened by PCR amplification with primers ldhD Seq F1 (SEQ ID NO:43) and D check R (SEQ ID NO:44) to distinguish between wild-type and clones carrying the sco event. To obtain clones with a double crossover, the sco strains were passaged for approximately 30 generations in MRS medium with 20 mM D, L-lactate (Sigma, St. Louis, Mo.) at 37° C. and then plated for single colonies on MRS with lactate. Colonies were picked and patched onto MRS with lactate and MRS with lactate containing 1 µg/ml of erythromycin to find colonies sensitive to erythromycin. Sensitive colonies were screened by PCR amplification using primer D check R (SEQ ID NO:44) and D check F3 (SEQ ID NO:45). Wild-type colonies gave a 3.2 kbp product and deletion clones, called PN0512ΔldhD, gave a 2.3 kbp PCR product.

ΔldhDΔldhL1

A deletion of the ldhL1 gene was made in the PN0512ΔldhD strain background in order to make a double ΔldhL1ΔldhD deletion strain. The knockout cassette to delete the ldhL1 gene was amplified from PN0512 genomic DNA. The ldhL1 left homologous arm was amplified using primers oBP31 (SEQ ID NO:46) containing a BglII restriction site and oBP32 (SEQ ID NO:47) containing an XhoI restriction site. The ldhL1 right homologous arm was amplified using primers oBP33 (SEQ ID NO:48) containing an XhoI restriction site and oBP34 (SEQ ID NO:49) containing an XmaI restriction site. The ldhL1 left homologous arm was cloned into the BglII/XhoI sites and the ldhL1 right homologous arm was cloned into the XhoI/XmaI sites of pFP996pyrFΔerm, a derivative of pFP996. pFP996pyrFΔerm contains the pyrF sequence (SEQ ID NO:7) encoding orotidine-5'-phosphate decarboxylase from Lactobacillus plantarum PN0512 in place of the erythromycin coding region in pFP996. The plasmid-borne pyrF gene, in conjunction with the chemical 5-fluoroorotic acid in a ΔpyrF strain, can be used as an effective counter-selection method in order to isolate the second homologous crossover. The XmaI fragment containing the ldhL1 homologous arms was isolated following XmaI digestion and cloned into the XmaI restriction site of pFP996, yielding a 900 bp left homologous region and a 1200 bp right homologous region resulting in vector pFP996-ldhL1-arms.

PN0512ΔldhD was transformed with pFP996-ldhL1-arms and grown at 30° C. in Lactobacilli MRS medium with lactate (20 mM) and erythromycin (1 µg/ml) for approximately 10 generations. Transformants were then grown under non-selective conditions at 37° C. for about 50 generations by serial inoculations in MRS+lactate before cultures were plated on MRS containing lactate and erythromycin (1 µg/ml). Isolates were screened by colony PCR for a single crossover using chromosomal specific primer oBP49 (SEQ ID NO:53) and plasmid specific primer oBP42 (SEQ ID NO:54). Single crossover integrants were grown at 37° C. for approximately 40 generations by serial inoculations under non-selective conditions in MRS with lactate before cultures were plated on MRS medium with lactate. Isolates were patched to MRS with lactate plates, grown at 37° C., and then patched onto MRS plates with lactate and erythromycin (1 µg/ml). Erythromycin sensitive isolates were screened by colony PCR for the presence of a wild-type or deletion second crossover using chromosomal specific primers oBP49 (SEQ ID NO:53) and oBP56 (SEQ ID NO:55). A wild-type sequence yielded a 3505 bp product and a deletion sequence yielded a 2545 bp product. The deletions were confirmed by sequencing the PCR product and absence of plasmid was tested by colony PCR with primers oBP42 (SEQ ID NO:54) and oBP57 (SEQ ID NO:58).

The Lactobacillus plantarum PN0512 double ldhDldhL1 deletion strain was designated PNP0001. The ΔldhD deletion included 83 bp upstream of where the ldhD start codon was through amino acid 279 of 332. The ΔldhL1 deletion included the fMet through the final amino acid.

Example 2

Product Analysis of a Lactobacillus Plantarum Strain Deleted for the Two Lactate Dehydrogenases, LdhD and LdhL1

The purpose of this example is to demonstrate the products produced by the Lactobacillus plantarum PN0512 double ldhDldhL1 deletion strain compared to the wild-type strain.

Strains PN0512 (wild-type) and PNP0001 (ΔldhDΔldhL1) were grown in rich medium, Lactobacilli MRS medium (Accumedia, Neogen Corporation, Lansing, Mich.), at 30° C. without shaking under anaerobic conditions in an anaerobic chamber (Coy Laboratories Inc., Grass Lake, Mich.). Both cultures were grown to a similar OD600 about 8.5. PNP0001 grew at a rate that was approximately 2.5 times slower than the wild-type PN0512. In order to reach a similar OD600, strain PN0512 was grown for 16 hours and strain PNP0001 was grown for 41 hours. Cultures were centrifuged at 3700×g for 10 minutes at 4° C. and culture supernatants were filtered through a 0.2 µm filter (Pall Life Sciences, Ann Arbor, Mich.). The filtered supernatants were analyzed by HPLC with column Shodex SUGAR SH1011 (Showa Denko K.K., Kawasaki, Japan) and refractive index detection for levels of glucose, citrate, acetate, lactate, acetoin, ethanol, succinate, and formate.

Figure 2:
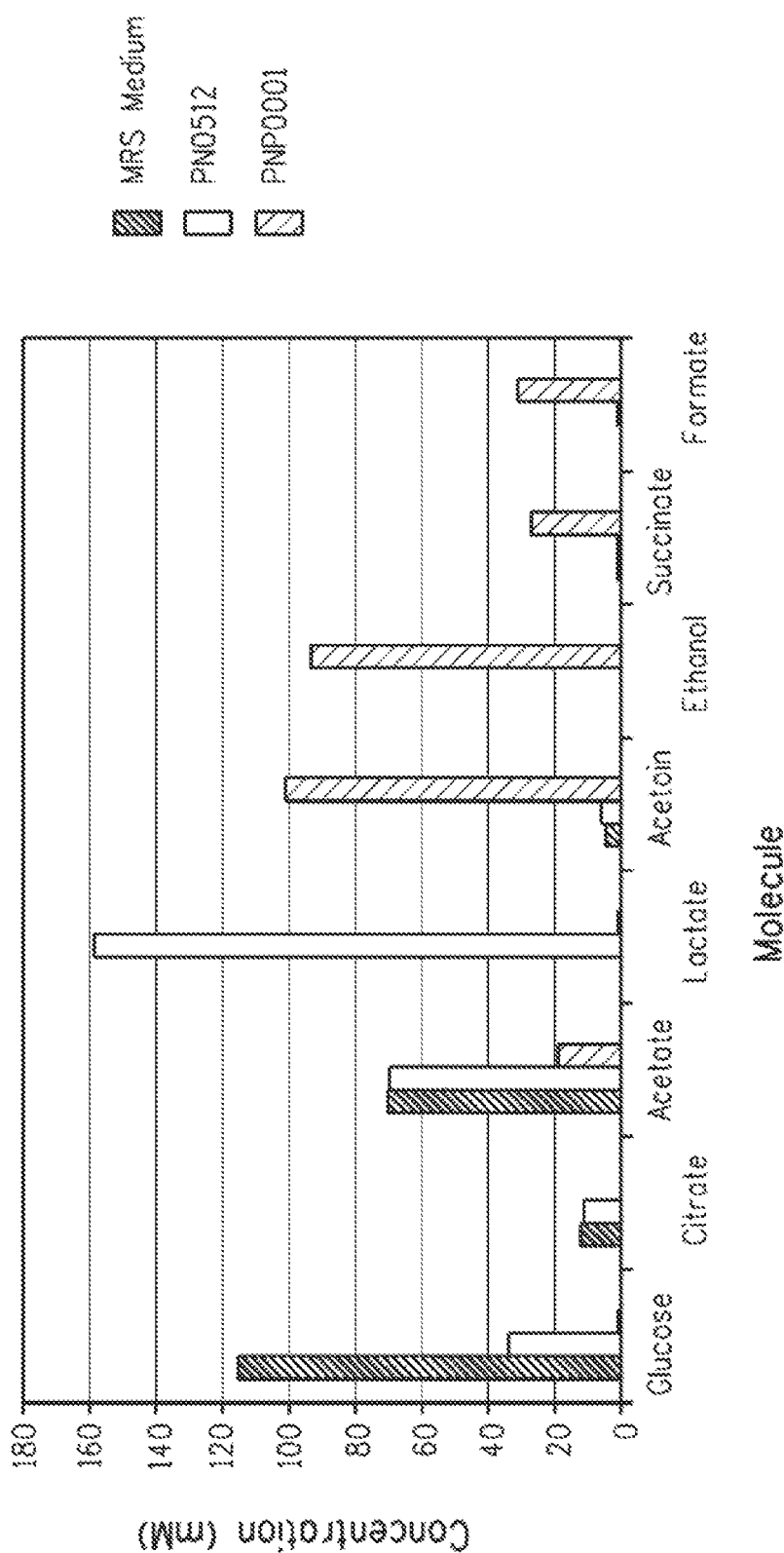
FIG. 2 shows a graph of products made in *L. plantarum* strains PN0512 (control) and PNP0001 (ldhDldhL1 deletion strain).

Results in FIG. 2 show the consumption of the medium constituents and the products that were formed. 71% of the 114 mM glucose was consumed in the PN0512 culture and 158 mM lactic acid was produced. Significant amounts of other products were not detected. 99% of the glucose, as well as 100% of the 12 mM citrate and 76% of the 70 mM acetate was consumed in the PNP0001 culture. PNP0001 produced only 1 mM lactate. Instead, the main products were acetoin (102 mM) and ethanol (93 mM), along with succinate (28 mM) and formate (31 mM). These data demonstrated that the ΔldhD and ΔldhL1 deletions effectively eliminated major production of lactic acid and led to a mixed fermentation product profile.

Example 3

Construction of Plasmids for the Production of Meso-2,3-Butanediol

The purpose of this example is to describe the construction of a plasmid for expression of a heterologous butanediol dehydrogenase. The ldhL1 promoter region (SEQ ID NO:8) from L. plantarum PN0512 was amplified with primers AA135 (SEQ ID O:61), containing EcoRI, SpeI, and AflII sites, and AA136 (SEQ ID NO:62), containing an XhoI site, from PN0512 genomic DNA using Phusion High-Fidelity PCR Master Mix. The resulting PCR fragment and pFP996 were ligated after digestion with EcoRI and XhoI to create vector pFP996PldhL1 (SEQ ID NO:36).

A secondary alcohol dehydrogenase encoded by the Achromobacter xylosoxidans sadB gene (coding region SEQ ID NO:9 and protein SEQ ID NO:10) was disclosed in U.S. patent application Ser. No. 12/430,356. The sadB coding region was amplified with primers oBP112 (SEQ ID NO:50), containing XhoI, NheI, and EcoRV sites along with a ribosome binding site (SEQ ID NO:51), and oBP113 (SEQ ID NO:52), containing a KpnI site, from vector pRS426::FBAbudC+GPM-sadB using Phusion High-Fidelity PCR Master Mix. pRS426 is a yeast shuttle vector (American Type Culture Collection, Rockville, Md.), which contains an *E. coli* replication origin (e.g., pMB1), a yeast 2µ origin of replication, and Ura3 marker for nutritional selection. pRS426::FBA-budC+GPM-sadB contains the FBA promoter (SEQ ID NO:11) from the *S. cerevisiae* fructose 1,6-bisphosphate aldolase gene operably linked to the budC coding region for butanediol dehydrogenase from *Klebsiella pneumonia* (coding region SEQ ID NO:12). In addition it has the yeast GPM1 promoter (SEQ ID NO:14) operably linked to the *Achromobacter xylosoxidans* sadB coding region (SEQ ID NO:9). The construction of pRS426::FBA-budC+GPM-sadB is described in Example 3 of U.S. patent application Ser. No. 12/477,942, which is herein incorporated by reference.

The sadB coding region PCR fragment and pFP996PldhL1 were ligated after digestion with XhoI and KpnI to create vector pFP996PldhL1-sadB. The *Klebsiella pneumoniae* budC coding region for butanediol dehydrogenase (SEQ ID NO:12) was amplified with primers oBP114 (SEQ ID NO:56), containing a NheI site and a ribosome binding site, and oBP115 (SEQ ID NO:57), containing an EcoRV site, from vector pRS426::FBA-budC+GPM-sadB using Phusion High-Fidelity PCR Master Mix. The resulting PCR fragment and pFP996PldhL1-sadB were ligated after digestion with NheI and EcoRV to create vector pFP996PldhL1-budC-sadB (SEQ ID NO:37). The sadB gene in vector pFP996PldhL1-budC-sadB was deleted to create vector pFP996PldhL1-budC (SEQ ID NO:38). Vector pFP996PldhL1-budC-sadB was digested with EcoRV and HindIII, the HindII site was filled in with T4 DNAP, and then the plasmid was re-ligated. Candidates were screened by colony PCR with primers oBP42 (SEQ ID NO:54) and oBP57 (SEQ ID NO:58) for plasmids that did not contain the sadB gene and then sequenced.

Example 4

Production of Meso-2,3-Butanediol Using a Recombinant *Lactobacillus Plantarum* Strain Grown in Rich Medium The purpose of this example is to demonstrate the production of meso-2,3-butanediol using a recombinant *Lactobacillus plantarum* strain containing an engineered pathway in rich medium. Specifically, a *Lactobacillus plantarum* strain deleted for the two endogenous lactate dehydrogenases, LdhD and LdhL1, and containing a plasmid, pFP996PldhL1-budC-sadB, expressing the *Klebsiella pneumoniae* budC coding region for butanediol dehydrogenase was grown in MRS medium. The first two enzymes for the butanediol pathway, acetolactate synthase and acetolactate decarboxylase, were provided by native expression from the chromosome. sadB encodes a butanol dehydrogenase that in the presence of 2-butanone would provide an electron sink that could be required to balance redox equivalents for 2,3-butanediol production.

Wild-type *Lactobacillus plantarum* strain PN0512 and strain PNP0001 were transformed with plasmid pFP996PldhL1-budC-sadB. Strains were transformed as in Example 1, except glycine was omitted from the medium for strain PNP0001. The resulting PNP0001/pFP996PldhL1-budC-sadB strain was designated PNP0002 and the PN0512/pFP996-budC-sadB strain designated BP134. Strains were grown in MRS medium with 0.5% 2-butanone. Strains containing plasmids were grown in medium also containing 2 µg/ml of erythromycin.

145 ml of medium was inoculated with strains PNP0001, PNP0001/pFP996PldhL1-budC-sadB (PNP0002), or PN0512/pFP996PldhL1-budC-sadB (BP134) from overnight cultures at a dilution of 1:145 in 175 ml sealed serum bottles. Cultures were grown at 30° C. for 24 hours without shaking. Strain BP134 reached an OD600 6.5, strain PNP0001 an OD600 8.1, and strain PNP0002 an OD600 6.2. The cultures were started at a higher inoculum so there was a shorter lag and fewer doublings to get to saturation, to reduce the difference in growth that was observed in Example 2. Samples of the cultures were centrifuged at 3700×g for 10 minutes at 4° C. and the supernatants filtered through a 0.2 µm filter (Pall Life Sciences, Ann Arbor, Mich.). The filtered supernatants were analyzed by HPLC with column Shodex SUGAR SH1011 (Showa Denko K.K., Kawasaki, Japan) and refractive index detection for levels of glucose, citrate, acetate, lactate, acetoin, meso-2,3-butanediol, ethanol, succinate, and formate.

Figure 3:
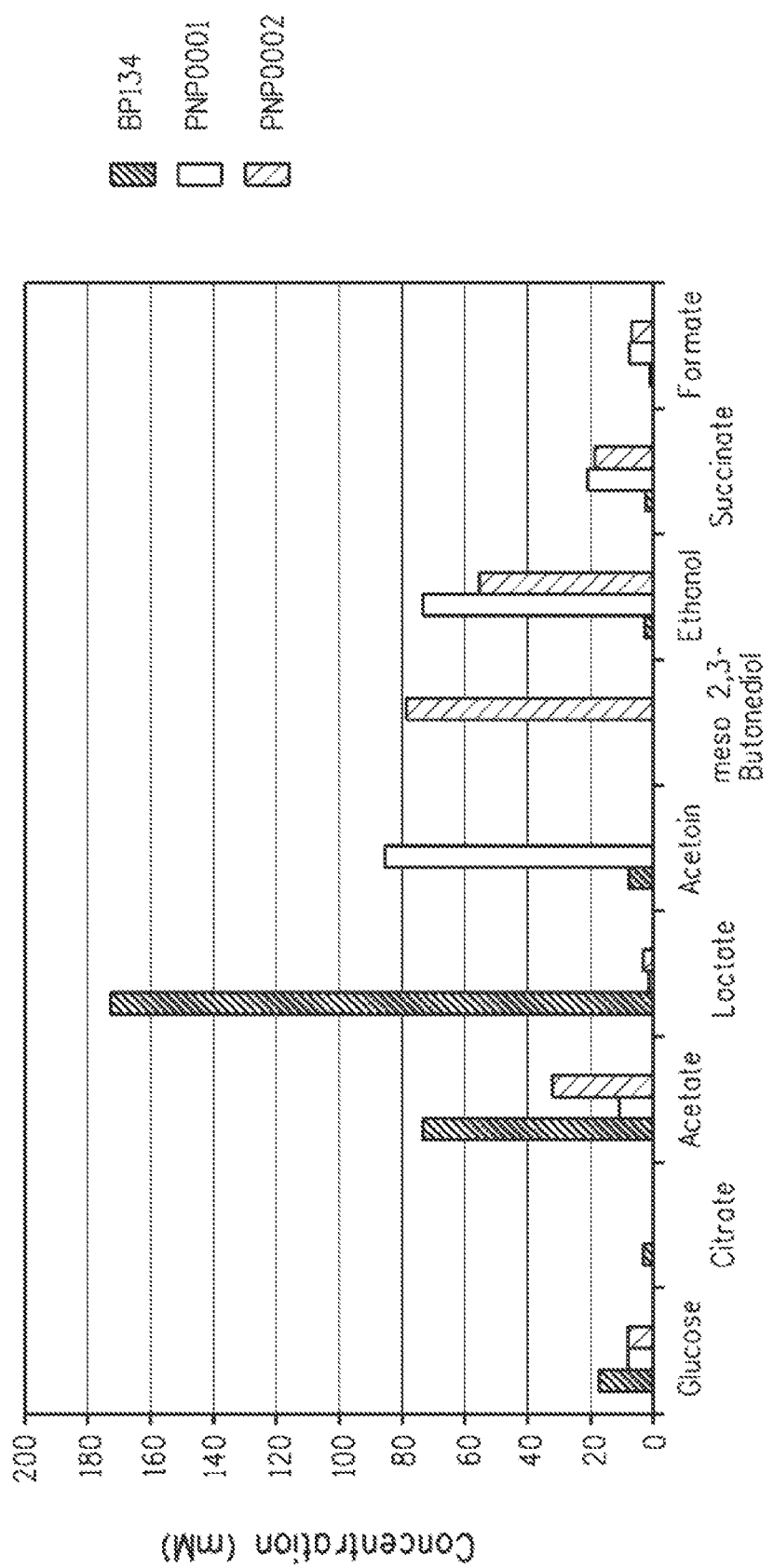
FIG. 3 shows a graph of products made in *L. plantarum* strains BP134 (control with budC and sadB genes), PNP0001 (ldh deletion), and PNP0002 (ldh deletion with budC and sadB genes) grown in rich medium.

Results in FIG. 3 show the consumption of the medium constituents and the products that were formed. Strain BP134 consumed 84% of the glucose, 64% of the citrate, and no acetate. This strain produced, similar to the wild-type strain without the plasmid, almost entirely lactic acid, 172 mM. Strain PNP0001 consumed 91% of the glucose, 100% of the citrate, and 82% of the acetate. As in example 2, the main products of strain PNP0001 were acetoin (86 mM) and ethanol (73 mM), along with succinate (21 mM) and formate (8 mM). Strain PNP0002 consumed 92% of the glucose, 100% of the citrate, and 53% of the acetate. In contrast to strain PNP0001, no acetoin was detected for strain PNP0002. Instead, the main product was meso-2,3-butanediol (78 mM), along with ethanol (54 mM), succinate (19 mM), and formate (7 mM). Meso-2,3-butanediol accounted for 49 Mol % of the measured products. These data showed that with the presence of the heterologous budC expressing plasmid in the double ldh deletion strain, acetoin was converted to meso-2,3-butanediol when cells were grown in rich medium. The titer of meso-2,3-butanediol was 7.0 g/L with a yield of 0.41 g/g of glucose consumed.

Example 5

Production of Meso-2,3-Butanediol Using a Recombinant *Lactobacillus Plantarum* Strain Containing Vector pFP996PldhL1-budC-sadB Grown in Synthetic Medium with Glucose or Sucrose The purpose of this example is to demonstrate the production of meso-2,3-butanediol using a recombinant *Lactobacillus plantarum* strain containing an engineered pathway in synthetic medium. Specifically, a *Lactobacillus plantarum* strain deleted for the two endogenous lactate dehydrogenases, LdhD and LdhL1, and containing a plasmid, pFP996PldhL1-budC-sadB, expressing the *Klebsiella pneumoniae* budC coding region for butanediol dehydrogenase was grown in synthetic medium with glucose or sucrose. The first two enzymes for the butanediol pathway, acetolactate synthase and acetolactate decarboxylase, were provided by native expression from the chromosome.

Strain PNP0001/pFP996PldhL1-budC-sadB (PNP0002) was grown in a synthetic medium with 20 mM glucose or sucrose and 2 µg/ml erythromycin. The synthetic medium consisted of: 10 mM ammonium sulfate, 100 mM MES pH6, 5 mM potassium phosphate pH 6, 1% S10 metal mix, 20 mM glucose or sucrose, 0.5% yeast extract, 0.01% casamino acids, and 10 mM ammonium citrate. 100% S10 metal mix consists of 200 mM $MgCl_2$, 70 mM $CaCl_2$, 5 mM $MnCl_2$, 100 µM $FeCl_3$, 100 µM $ZnCl_2$, 172 µM $CuSO_4$, 253 µM $CoCl_2$, 242 µM $NaMoO_4$, and 200 µM thiamine hydrochloride. All medium constituents were purchased from Sigma-Aldrich (St. Louis, Mo.). 25 ml of medium was inoculated with PNP0002 and grown at 30° C. overnight without shaking in an anaerobic box containing a Pack-Anaero sachet (Mitsubishi Gas Chemical Co., Tokyo, Japan) to an OD600 0.72 (glucose) or 0.88 (sucrose). Overnight cultures were centrifuged for 5 minutes at 5 k RPM and then resuspended in fresh medium at a final dilution of 1:10. 25 ml of culture was grown in an anaerobic box with a Pack-Anaero sachet at 30° C. without shaking for 28 hours to an OD600 3.18 (glucose) or 4.52 (sucrose). Samples were centrifuged and supernatants filtered through a 0.2 µm filter (Pall Life Sciences, Ann Arbor, Mich.). The filtered supernatants were analyzed by GC with column HP-Innowax Polyethylene Glycol (19091N-113, Agilent Technologies, Santa Clara, Calif.) and flame ionization detection for levels of meso-2,3-butanediol, acetoin, and ethanol. The results in Table 5 show that meso-2,3-butanediol accounted for greater than 50% of the two main products, meso-2,3-butanediol and ethanol, similar to results obtained with rich medium.

TABLE 5

Production of meso-2,3-butanediol, acetoin, and ethanol by PNP0001/pFP996PldhL1-budC-sadB grown in synthetic medium with glucose or sucrose.

| Culture | Concentration (mM) | | |
|---|---|---|---|
| | meso-2,3-butanediol | Acetoin | ethanol |
| Glucose | 12.9 | 2.4 | 10.9 |
| Sucrose | 25.5 | 3.1 | 10.0 |

These data demonstrated that a recombinant *Lactobacillus plantarum* strain deleted for the ldhD and ldhL1 genes and containing a plasmid expressing the heterologous gene budC produced meso-2,3-butanediol when cells were grown in synthetic medium with either glucose or sucrose as the fermentable sugar.

Production of 2,3-butanediol without 2-butanone in the medium indicated that the additional electron sink was not needed to provide redox balance for the flux described.

Example 6

Production of Meso-2,3-Butanediol Using a Recombinant *Lactobacillus Plantarum* Strain Containing Vector pFP996PldhL1-budC Grown in Synthetic Medium with Sucrose The purpose of this example is to demonstrate the production of meso-2,3-butanediol using a recombinant *Lactobacillus plantarum* strain containing an engineered pathway in synthetic medium. Specifically, a *Lactobacillus plantarum* strain deleted for the two endogenous lactate dehydrogenases, LdhD and LdhL1, and containing a plasmid, pFP996PldhL1-budC, expressing the *Klebsiella pneumoniae* budC coding region for butanediol dehydrogenase was grown in synthetic medium with sucrose. The first two enzymes for the butanediol pathway, acetolactate synthase and acetolactate decarboxylase, were provided by native expression from the chromosome. Since Example 5 showed that no additional redox balancing electron sink was needed, sadB expression was not included.

Strain PNP0001 was transformed, as in Example 1 except glycine was omitted, with plasmids pFP996PldhL1 and pFP996PldhL1-budC. Strains PNP0001/pFP996PldhL1 and PNP0001/pFP996PldhL1-budC were grown overnight in *Lactobacilli* MRS medium with 2 µg/ml erythromycin at 30° C. in an anaerobic chamber (Coy Laboratories Inc., Grass Lake, Mich.). Vials containing synthetic medium, which had been deoxygenated overnight in an anaerobic chamber, were inoculated with overnight culture to an OD600 of about 0.02 and sealed in the anaerobic chamber. The synthetic medium consisted of: 10 mM ammonium sulfate, 100 mM MES pH6, 5 mM potassium phosphate pH6, 1% S10 metal mix, 20 mM sucrose, 0.5% yeast extract, 0.01% casamino acids, 10 mM ammonium citrate, and 2 µg/ml erythromycin. Cultures were grown at 30° C. without shaking for 48 hours to an OD600 about 2.3. Samples of the cultures were centrifuged at 3700×g for 10 minutes at 4° C. and the supernatants filtered through a 0.2 µm filter (Pall Life Sciences, Ann Arbor, Mich.). The filtered supernatants were analyzed by GC with column HP-Innowax Polyethylene Glycol (19091N-113, Agilent Technologies, Santa Clara, Calif.) and flame ionization detection for levels of meso-2,3-butanediol, acetoin, and ethanol.

Results in Table 5 show the production of meso-2,3-butanediol, acetoin, and ethanol for strain PNP0001/pFP996PldhL1-budC grown in synthetic medium with sucrose. The amount of meso-2,3-butanediol produced by this strain is comparable to PNP0001 with vector pFP996PldhL1-budC-sadB (Example 5).

TABLE 5

Production of meso-2,3-butanediol, acetoin, and ethanol by PNP0001/pFP996PldhL1 and PNP0001/pFP996PldhL1-budC grown in synthetic medium with sucrose.

| Strain | Concentration (mM) | | |
|---|---|---|---|
| | meso-2,3-butanediol | acetoin | ethanol |
| PNP0001/pFP996PldhL1 | 0.5 | 26.2 | 24.9 |
| PNP0001/pFP996PldhL1-budC | 33.3 | 2.7 | 18.1 |

Example 7

Prophetic

Production of 2-Butanol by a Recombinant *L. plantarum* Strain Expressing $B_{12}$-Independent Diol Dehydratase A vector expressing butanediol dehydrogenase encoded by the *Klebsiella pneumoniae* budC gene, secondary alcohol dehydrogenase encoded by the *Achromobacter xylosoxidans* sadB gene, and coenzyme $B_{12}$-independent (S-adenosylmethionine-dependent) butanediol dehydratase and its associated reactivase encoded by the *Roseburia inulinivorans* rdhtA (DNA SEQ ID NO: 15; protein SEQ ID NO:16) and rdhtB (DNA SEQ ID NO: 17; protein SEQ ID NO:18) genes respectively, is constructed. The *Roseburia inulinivorans* coenzyme $B_{12}$-independent propanediol dehydratase and reactivase are disclosed in US Patent Pub No. US20090155870A1. Therein the sequences encoding rdhtA and rdhtB were synthesized as one DNA fragment (SEQ ID NO:67) by standard methods and cloned into an *E. coli* vector (by DNA2.0, Inc., Menlo Park, Calif.) resulting in pJ206::rdhtAB.

The *Roseburia inulinivorans* rdhtA and rdhtB coding regions are amplified with primers rdhtAB-up (SEQ ID NO:59) and rdhtAB-down (SEQ ID NO:60), each containing a BsrGI restriction site, from vector pJ206::rdhtAB. The resulting PCR fragment and pFP996PldhL1-budC-sadB are ligated after digestion with BsrGI and used to transform E. coli TOP10 cells. Plasmids that have the rdhtAB coding regions in the same orientation as budC and sadB are identified by PCR with primers rhdtAB-up (SEQ ID NO:59) and oBP42 (SEQ ID NO:54) and the resulting, correctly oriented clone is named pFP996PldhL1-budC-sadB-rdhtAB.

Strain PNP0001 is transformed with vector pFP996PldhL1-budC-sadB-rdhtAB as described in Example 1, except glycine is omitted from the medium. MRS medium containing 2 μg/ml erythromycin is inoculated with strain PNP0001/pFP996PldhL1-budC-sadB-rdhtAB and grown overnight at 30° C. in an anaerobic chamber. Vials containing MRS medium with 2 μg/ml erythromycin, which is deoxygenated overnight in an anaerobic chamber, are inoculated with overnight culture at a 1:100 dilution and sealed in the anaerobic chamber. Cultures are grown at 30° C. without shaking for 48 hours. The culture supernatant is tested and 2-butanol is detected by HPLC or GC.

Example 8

Construction of the *Lactobacillus Plantarum* PN0512 ΔldhDΔldhL1ΔpflB2A2::alsS(o) Strain The purpose of this example is to describe the construction of a *Lactobacillus plantarum* strain in the PN0512ΔldhDΔldhL1 strain background that is deleted for the genes pflB2, encoding formate C-acetyltransferase (pyruvate formate lyase), and pflA2, encoding the formate C-acetyltransferase activating enzyme, and thus does not contain formate C-acetyltransferase activity. Whereas *Lactobacillus plantarum* WCFS1 contains two genes encoding formate C-acetyltransferase and two genes encoding formate C-acetyltransferase activating enzyme, *Lactobacillus plantarum* PN0512 only contains one gene encoding formate C-acetyltransferase and one gene encoding formate C-acetyltransferase activating enzyme. A gene (alsS), codon optimized for expression in *Lactobacillus plantarum*, encoding the *Bacillus subtilis* acetolactate synthase enzyme was integrated in place of the deleted pflB2A2 genes.

The pflB2A2 gene knockout and alsS gene integration were constructed using the two-step homologous recombination procedure described above. The knockout deleted the C-terminal 351 amino acids (nucleotides 1204 through 2256 of the coding sequence) of pflB2 and the entire coding sequence of pflA2. The deleted sequence was replaced with a stop codon, in frame with the truncated pflB2, followed by a ribosome binding sequence and *Bacillus subtilis* alsS gene codon optimized for expression in *Lactobacillus plantarum*.

The knockout/integration vector was constructed in plasmid pFP996 as follows. The homologous arms to delete the pflB2A2 genes were amplified from PN0512 genomic DNA. The pflB2A2 left homologous arm was amplified using primers oBP309 (SEQ ID NO:104) containing an XhoI restriction site and oBP310 (SEQ ID NO:105) containing a stop codon (complement of TAA) and XmaI restriction site. The pflB2A2 right homologous arm was amplified using primers oBP271 (SEQ ID NO:106) containing a KpnI restriction site and oBP272 (SEQ ID NO:107) containing a BsrGI restriction site. The pflB2A2 left homologous arm was cloned into the XhoI/XmaI sites and the pflB2A2 right homologous arm was cloned into the KpnI/BsrGI sites of pFP996 to create pFP996-pflB2A2arms. The *Bacillus subtilis* alsS gene codon optimized for expression in *Lactobacillus plantarum* (SEQ ID NO:87; synthesized by Genscript Corp, Piscataway, N.J.) was amplified using primers oBP282 (SEQ ID NO:108) containing an XmaI restriction site and oBP283 (SEQ ID NO:109) containing a KpnI restriction site. The codon optimized alsS gene was cloned into the XmaI/KpnI sites of pFP996-pflB2A2arms to create pFP996-pflB2A2arms-als(o).

PN0512 ΔldhDΔldhL1 was transformed with pFP996-pflB2A2arms-als(o) as above, except competent cells were prepared in the absence of glycine, and transformants were selected on MRS plates containing 1 μg/ml erythromycin. A transformant was grown at 30° C. for about 35 generations by serial inoculations in MRS before cultures were plated on MRS containing erythromycin (1 μg/ml). Isolates were screened by colony PCR for a single crossover using chromosomal specific primer oAA227 (SEQ ID NO:110) and plasmid specific primer oBP42 (SEQ ID NO:54). A single crossover integrant was grown at 37oC for approximately 35 generations by serial inoculations in MRS before cultures were plated on MRS medium. Erythromycin sensitive isolates were screened by colony PCR for the presence of a wild-type or deletion/integration second crossover using als (o) specific primer oAA228 (SEQ ID NO:111) and chromosomal specific primer oBP280 (SEQ ID NO:112). The deletion/integration strain PN0512 ΔldhDΔldhL1ΔpflB2A2::als (o)$^+$, named BP556, was confirmed by sequencing the PCR product amplified with chromosomal specific primers oBP278 (SEQ ID NO:113) and oBP280 (SEQ ID NO:112).

Example 9

Production of Meso-2,3-Butanediol Using a Recombinant *Lactobacillus Plantarum* Strain Lacking Both Lactate Dehydrogenase Activity and Formate C-Acetyltransferase Activity Grown in Rich Medium The purpose of this example is to demonstrate the production of meso-2,3-butanediol using a recombinant *Lactobacillus plantarum* strain containing an engineered pathway in rich medium. Specifically, a *Lactobacillus plantarum* strain deleted for the two endogenous lactate dehydrogenases, LdhD and LdhL1, deleted for the formate C-acetyltransferase, pflB2, and containing a plasmid, pFP996PldhL1-budC, expressing the *Klebsiella pneumoniae* budC coding region for butanediol dehydrogenase was grown in MRS medium. The second enzyme for the butanediol pathway, acetolactate decarboxylase, was provided by native expression from the chromosome. The first enzyme for the butanediol pathway, acetolactate synthase, was provided by native expression from the chromosome and the heterologous *Bacillus subtilis* alsS gene integrated into the pflB2A2 locus.

Strain BP556 was transformed as in Example 1, except glycine was omitted, with plasmid pFP996PldhL1-budC. Strains PNP0001/pFP996PldhL1-budC and BP556/pFP996PldhL1-budC were grown overnight in *Lactobacilli* MRS medium with 2 μg/ml erythromycin at 30° C. Overnight cultures were used to inoculate 5 ml MRS medium with 2 μg/ml erythromycin in 15 ml screw cap tubes. Cultures were grown at 30° C. without shaking in an anaerobic box containing a Pack-Anaero sachet (Mitsubishi Gas Chemical Co., Tokyo, Japan) for 24 hours to an OD600 about 6.5. Samples of the cultures were centrifuged at 3700×g for 10 minutes at 4° C. and the supernatants filtered through a 0.2 μm filter (Pall Life Sciences, Ann Arbor, Mich.). The filtered supernatants were analyzed by HPLC with column Shodex SUGAR SH1011 (Showa Denko K.K., Kawasaki, Japan) and refractive index detection. Greater than 99% of the glucose was consumed in both cultures. The pflB2A2 deletion led to no detectable levels of formate for strain BP556/pFP996PldhL1-budC, whereas strain PNP0001/pFP996PldhL1-budC produced 20 mM formate. Production of meso-2,3-butanediol increased 12% for BP556/pFP996PldhL1-budC (92 mM) compared to PNP0001/pFP996PldhL1-budC (82 mM).

What is claimed is:

1. A recombinant lactic acid bacterial cell comprising at least one gene encoding a heterologous polypeptide having butanediol dehydrogenase activity wherein the bacterial cell is substantially free of lactate dehydrogenase activity and wherein the cell produces 2,3-butanediol, and wherein the cell comprises a 2-butanol or 2-butanone biosynthetic pathway.

2. The bacterial cell of claim 1 comprising a disruption in at least one endogenous gene encoding a polypeptide having lactate dehydrogenase activity.

3. The bacterial cell of claim 1 wherein the cell is a member of a genus selected from the group consisting of *Lactococcus, Lactobacillus, Leuconostoc, Oenococcus, Pediococcus*, and *Streptococcus*.

4. The bacterial cell of claim 1 further comprising at least one genetic modification that reduces pyruvate formate lyase activity.

5. The bacterial cell of claim 4 wherein the genetic modification affects a gene encoding pyruvate formate lyase, a gene encoding pyruvate formate lyase activating enzyme, or both.

6. The bacterial cell of claim 5 wherein the gene encoding pyruvate formate lyase is selected from the group consisting of pfl, pflB1 and pfl B2 and the gene encoding pyruvate formate lyase activating enzyme is selected from the group consisting of pflA, pflA1, and pflA2.

7. The bacterial cell of claim 2 wherein the polypeptide having lactate dehydrogenase activity is encoded by a gene selected from the group consisting of ldhL, ldhD, ldhL1, and ldhL2.

8. The bacterial cell of claim 7 wherein the lactic acid host cell is *Lactobacillus plantarum Lactococcus lactis, Leuconostoc mesenteroides, Streptococcus thermophilus, Pediococcus pentosaceus*, or *Lactobacillus acidophilus*.

9. The bacterial cell of claim 1 wherein the cell produces 2-butanone.

10. The bacterial cell of claim 1 wherein the cell produces 2-butanol.

11. The bacterial cell of claim 10 comprising a 2-butanol biosynthetic pathway, wherein the biosynthetic pathway comprises the following substrate to product conversions:
    a) pyruvate to acetolactate;
    b) acetolactate to acetoin;
    c) acetoin to 2,3-butanediol;
    d) 2,3-butanediol to 2-butanone; and
    e) 2-butanone to 2-butanol.

12. The bacterial cell of claim 9 comprising a 2-butanone biosynthetic pathway, wherein the biosynthetic pathway comprises the following substrate to product conversions:
    a) pyruvate to acetolactate;
    b) acetolactate to acetoin;
    c) acetoin to 2,3-butanediol; and
    d) 2,3-butanediol to 2-butanone.

13. A method for the production of 2-butanol comprising:
    a) providing the recombinant lactic acid bacterial cell of claim 1 comprising a 2-butanol biosynthetic pathway; and
    b) growing the bacterial cell of step (a) under conditions whereby 2-butanol is produced.

14. A method for the production of 2-butanone comprising:
    a) providing the recombinant lactic acid bacterial cell of claim 1 comprising a 2-butanone biosynthetic pathway; and
    b) growing the bacterial cell of step (a) under conditions whereby 2-butanone is produced.

15. The lactic acid bacterial cell of claim 1 comprising a 2-butanol biosynthetic pathway, wherein the heterologous polypeptide having butanediol dehydrogenase activity comprises an amino acid sequence with at least about 95% sequence identity to SEQ ID NO:13, SEQ ID NO:64, or SEQ ID NO:66.

16. The lactic acid bacterial cell of claim 15, wherein the heterologous polypeptide having butanediol dehydrogenase activity comprises the amino acid sequence of SEQ ID NO:13.

17. The lactic acid bacterial cell of claim 11, wherein the substrate to product conversion e) is catalyzed by a heterologous butanol dehydrogenase comprising an amino acid sequence with at least about 95% sequence identity to SEQ ID NO:10.

* * * * *